US012404227B2

(12) United States Patent
Copp et al.

(10) Patent No.: US 12,404,227 B2
(45) Date of Patent: Sep. 2, 2025

(54) METHODS OF MAKING BEMPEDOIC ACID AND COMPOSITIONS OF THE SAME

(71) Applicant: Esperion Therapeutics, Inc., Ann Arbor, MI (US)

(72) Inventors: Richard Copp, Pinckney, MI (US); Mohamed Abdelnasser, New City, NY (US); Christopher M. Cimarusti, Clementon, NJ (US); Jonathan Lane, Longmont, CO (US); Michael Barkman, Louisville, CO (US); Rasidul Amin, Cary, NC (US); Arthur John Cooper, Mentor, OH (US); Damodaragounder Gopal, Highland Heights, OH (US); Philipp Selig, Linz (AT)

(73) Assignee: Esperion Therapeutics, Inc., Ann Arbor, MI (US)

( * ) Notice: Subject to any disclaimer, the term of this patent is extended or adjusted under 35 U.S.C. 154(b) by 134 days.

(21) Appl. No.: 18/450,591

(22) Filed: Aug. 16, 2023

(65) Prior Publication Data

US 2024/0182396 A1   Jun. 6, 2024

Related U.S. Application Data

(63) Continuation of application No. 17/577,829, filed on Jan. 18, 2022, now Pat. No. 11,760,714, which is a continuation of application No. 17/150,321, filed on Jan. 15, 2021, now abandoned, which is a continuation of application No. PCT/US2020/038622, filed on Jun. 19, 2020.

(60) Provisional application No. 62/864,873, filed on Jun. 21, 2019.

(51) Int. Cl.
*C07C 51/04* (2006.01)
*C07C 59/285* (2006.01)

(52) U.S. Cl.
CPC ............ *C07C 51/04* (2013.01); *C07C 59/285* (2013.01); *C07B 2200/13* (2013.01)

(58) Field of Classification Search
CPC .... C07C 59/285; C07C 51/42; C07B 2200/13
USPC ........................................................ 514/574
See application file for complete search history.

(56) References Cited

U.S. PATENT DOCUMENTS

| | | |
|---|---|---|
| 3,152,148 A | 10/1964 | Easterly et al. |
| 3,441,605 A | 4/1969 | Blake |
| 3,773,946 A | 11/1973 | Creger |
| 3,930,024 A | 12/1975 | Creger |
| 4,281,200 A | 7/1981 | Snoble |
| 4,287,200 A | 9/1981 | Kawamatsu et al. |
| 4,584,321 A | 4/1986 | Manghisi et al. |
| 4,613,593 A | 9/1986 | Yamatsu et al. |
| 4,634,119 A | 1/1987 | Pesthy |
| 4,634,719 A | 1/1987 | Takaishi et al. |
| 4,639,344 A | 1/1987 | Ueno et al. |
| 4,689,344 A | 8/1987 | Bar-Tana |
| 4,711,896 A | 12/1987 | Bar-Tana et al. |
| 4,714,762 A | 12/1987 | Hoefle et al. |
| 4,896,344 A | 1/1990 | Grady et al. |
| 5,166,174 A | 11/1992 | Ueno et al. |
| 5,225,439 A | 7/1993 | Ueno et al. |
| 5,284,858 A | 2/1994 | Ueno et al. |
| 5,380,709 A | 1/1995 | Ueno et al. |
| 5,428,062 A | 6/1995 | Ueno et al. |
| 5,502,198 A | 3/1996 | Picard et al. |
| 5,504,073 A | 4/1996 | Homan |
| 5,570,569 A | 11/1996 | Masuda |
| 5,578,639 A | 11/1996 | Homan |
| 5,633,287 A | 5/1997 | Lee et al. |
| 5,648,387 A | 7/1997 | Bisgaier et al. |
| 5,750,569 A | 5/1998 | Bisgaier et al. |
| 5,756,344 A | 5/1998 | Onda et al. |
| 5,756,544 A | 5/1998 | Bisgaier et al. |
| 5,783,600 A | 7/1998 | Bisgaier et al. |
| 5,834,596 A | 11/1998 | Ageland et al. |
| 5,886,034 A | 3/1999 | Ueno et al. |
| 5,968,963 A | 10/1999 | Homan |
| 5,981,595 A | 11/1999 | Picard et al. |
| 6,004,925 A | 12/1999 | Dasseux et al. |
| 6,017,905 A | 1/2000 | Roark et al. |
| 6,037,323 A | 3/2000 | Dasseux et al. |
| 6,093,719 A | 7/2000 | Bocan |
| 6,093,744 A | 7/2000 | Lee et al. |

(Continued)

FOREIGN PATENT DOCUMENTS

| | | |
|---|---|---|
| CN | 107628975 A | 1/2018 |
| CN | 109721486 A | 5/2019 |

(Continued)

OTHER PUBLICATIONS

Ahuja, Chromatography & Separation Science (2003).
Azim et al. (2013) "HPLC Method Development and Validation: A Review," Int. Res. J. Pharm. 4(4)39-46.
Ballantyne et al. (2013) "Efficacy and Safety of a Novel Dual Modulator of Adenosine Triphosphate-Citrate Lyase and Adenosine Monophosphate-Activated Protein Kinase in Patients With Hypercholesterolemia Results of a Multicenter, Randomized, Double-Blind, Placebo-Controlled, Parallel-Group Trial" JACC 62(13) 1154-1162.
Ballantyne et al. (2016) "Effect of ETC-1002 on Serum Low-Density Lipoprotein Cholesterol in Hypercholesterolemic Patients Receiving Statin Therapy," Am. J. Cardio 117:1928-1933.

(Continued)

*Primary Examiner* — Ana Z Muresan
(74) *Attorney, Agent, or Firm* — Goodwin Procter LLP

(57) ABSTRACT

The invention provides methods of preparing 8-hydroxy-2,2,14,14-tetramethylpentadecanedioic acid and methods of making a pharmaceutical material comprising a purified amount of 8-hydroxy-2,2,14,14-tetramethylpentadecanedioic acid. Also provided are compositions and pharmaceutical materials including a purified amount of 8-hydroxy-2,2,14,14-tetramethylpentadecanedioic acid as well as methods of treating various diseases and conditions using the compositions and pharmaceutical materials.

20 Claims, 6 Drawing Sheets

(56) References Cited

U.S. PATENT DOCUMENTS

| | | |
|---|---|---|
| 6,124,309 A | 9/2000 | Bocan |
| 6,143,755 A | 11/2000 | Bocan |
| 6,362,236 B1 | 3/2002 | Aviram et al. |
| 6,410,802 B1 | 6/2002 | Dasseux et al. |
| 6,459,003 B1 | 10/2002 | Dasseux et al. |
| 6,506,799 B1 | 1/2003 | Dasseux |
| 6,646,170 B2 | 11/2003 | Dasseux et al. |
| 6,673,780 B2 | 1/2004 | Dasseux et al. |
| 6,699,910 B2 | 3/2004 | Dasseux et al. |
| 6,703,422 B2 | 3/2004 | Dasseux et al. |
| 6,713,507 B2 | 3/2004 | Dasseux et al. |
| 6,790,953 B2 | 9/2004 | Dasseux et al. |
| 6,831,105 B2 | 12/2004 | Dasseux |
| 6,909,014 B2 | 6/2005 | Dasseux et al. |
| 7,119,221 B2 | 10/2006 | Dasseux et al. |
| 7,192,940 B2 | 3/2007 | Dasseux et al. |
| 7,304,093 B2 | 12/2007 | Dasseux et al. |
| 7,335,689 B2 | 2/2008 | Dasseux et al. |
| 7,335,799 B2 | 2/2008 | Dasseux et al. |
| 7,405,226 B2 | 7/2008 | Dasseux et al. |
| 7,576,130 B2 | 8/2009 | Dasseux et al. |
| 7,705,177 B2 | 4/2010 | Oniciu et al. |
| 7,812,199 B2 | 10/2010 | Dasseux et al. |
| 7,838,554 B2 | 11/2010 | Dasseux et al. |
| 8,067,466 B2 | 11/2011 | Dasseux et al. |
| 8,084,498 B2 | 12/2011 | Dasseux et al. |
| 8,153,690 B2 | 4/2012 | Dasseux et al. |
| 8,309,604 B2 | 11/2012 | Dasseux et al. |
| 8,497,301 B2 | 7/2013 | Dasseux et al. |
| 8,623,915 B2 | 1/2014 | Dasseux et al. |
| 8,642,653 B2 | 2/2014 | Dasseux et al. |
| 9,000,041 B2 | 4/2015 | Dasseux et al. |
| 9,006,290 B2 | 4/2015 | Dasseux et al. |
| 9,452,964 B2 | 9/2016 | Dasseux et al. |
| 9,624,152 B2 | 4/2017 | Dasseux et al. |
| 9,855,240 B2 | 1/2018 | Zakrzewski |
| 10,028,926 B2 | 7/2018 | Bisgaier |
| 10,047,028 B2 | 8/2018 | Dasseux et al. |
| 10,118,881 B2 | 11/2018 | Dasseux et al. |
| 10,941,095 B2 | 3/2021 | Dasseux et al. |
| 2004/0214777 A1 | 10/2004 | McGrath |
| 2004/0214887 A1 | 10/2004 | Dasseux et al. |
| 2005/0043278 A1 | 2/2005 | Dasseux et al. |
| 2005/0119333 A1 | 6/2005 | Dasseux |
| 2005/0214887 A1 | 9/2005 | Emori et al. |
| 2007/0155704 A1 | 7/2007 | Dasseux et al. |
| 2007/0179120 A1 | 8/2007 | Dasseux et al. |
| 2008/0249166 A1 | 10/2008 | Dasseux et al. |
| 2009/0247489 A1 | 10/2009 | Dasseux et al. |
| 2012/0129930 A1 | 5/2012 | Dasseux et al. |
| 2012/0225908 A1 | 9/2012 | Dasseux et al. |
| 2015/0344388 A1 | 12/2015 | Dasseux et al. |
| 2015/0344389 A1 | 12/2015 | Dasseux et al. |
| 2016/0058751 A1 | 3/2016 | Vali et al. |
| 2018/0064671 A1 | 3/2018 | Newton et al. |
| 2018/0078518 A1 | 3/2018 | Newton et al. |
| 2018/0338922 A1 | 11/2018 | Abdelnasser et al. |
| 2019/0008779 A1 | 1/2019 | Oniciu et al. |
| 2019/0084908 A1 | 3/2019 | Dasseux et al. |

FOREIGN PATENT DOCUMENTS

| | | |
|---|---|---|
| EP | 0284108 A2 | 9/1988 |
| EP | 0824094 A1 | 2/1998 |
| EP | 1047421 A2 | 11/2000 |
| EP | 3666750 A1 | 6/2020 |
| FR | 1545224 A | 11/1968 |
| GB | 1196594 A | 7/1970 |
| GB | 1196595 A | 7/1970 |
| GB | 1196596 A | 7/1970 |
| GB | 1196597 A | 7/1970 |
| GB | 1196598 A | 7/1970 |
| WO | WO-1996/30328 A1 | 10/1996 |
| WO | WO-1998/30530 A1 | 7/1998 |
| WO | WO-1999/00116 A2 | 1/1999 |
| WO | WO-1999/26583 A2 | 6/1999 |
| WO | WO-2004/067489 A2 | 8/2004 |
| WO | WO-2017/023165 A1 | 2/2017 |
| WO | WO-2018/148417 A1 | 8/2018 |
| WO | WO-2018/218147 A1 | 11/2018 |
| WO | WO-2019/161307 A1 | 8/2019 |
| WO | WO-2020/141419 A2 | 7/2020 |
| WO | WO-2020/257573 A1 | 12/2020 |
| WO | WO-2021/110929 A1 | 6/2021 |
| WO | WO-2022/149161 A1 | 7/2022 |

OTHER PUBLICATIONS

Ballantyne et al. (2018) "Efficacy and safety of bempedoic acid added to ezetimibe in statin-tolerant patients with hypercholesterolemia: A randomized, placebo-controlled study," Atherosclerosis 277:195-203.

Bangalore et al. (2007) "Fixed-Dose Combinations Improve Medication Compliance: A Meta-Analysis" American Journal of Medicine 120:713-719.

Bari et al. (2007) "Impurity Profile: Significance in Active Pharmaceutical Ingredient," Eurasian Journal of Analytical Chemistry 2(1):32-53.

Bar-Tana, et al. (1989) "Synthesis and Hypolipidemic and Antidiabetogenic Activities of β,β,β', β'-Tetrasubstituted, Long-Chain Dioic Acids," J. Med. Chem. 32:2072-2084.

Bell (2013) "Combine and conquer: advantages and disadvantages of fixed-dose combination therapy" Diabetes, Obesity & Metabolism 15:291-300.

Bell et al. (2005) "alpha-Cycloalkyl-substituted omega-keto-dicarboxylic acids as lipid regulating agents" Bioorganic & Medicinal Chemistry 13:223-236.

Bilen et al. (2016) "Bempedoic Acid (ETC-1002): An Investigational Inhibitor of ATP Citrate Lyase," Curr. Atheroscler. Rep. 18:61 (7 pages).

Braatz et al., "Crystallization: Particle Size Control," Encyclopedia of Pharmaceutical Technol. 3d edition, vol. 1:858-71 at 858 (J. Swarbrick, ed., Informa Healthcare USA, Inc., 2007).

Byrne et al. (2016) "Tools and techniques for solvent selection: green solvent selection guides" Sustain Chem Process 4(7) (24 pages).

Chaikin et al. (1949) "Reduction of Aldehydes, Ketones and Acid Chlorides by Sodium Borohydride," J. Am. Chem. 71:122-125.

Chemical Engineering in the Pharmaceutical Industry: Drug Product Design, Development, and Modeling (2ed Mar. 29, 2019).

Clauss et al. (2009) "Ezetimibe treatment of pediatric patients with hypercholesterolemia," J Pediatr. 154(6):869-72.

Clayden et al., Organic Chemistry (2nd Ed 2012).

Elder et al. (2008) "Control and analysis of alkyl and benzyl halides and other related reactive organohalides as potential genotoxic impurities in active pharmaceutical ingredients (APIs)," J. Pharm. & Biomed Analysis 48:497-500.

Esperion Therapeutics Announces Positive Top-Line Phase 2b Results for ETC-1002, An Investigational Therapy for Patients with Hypercholesterolemia; available at https://www.esperion.com/news-releases/news-release-details/esperion-therapeutics-announces-positive-top-line-phase-2b (Publication date: Oct. 1, 2014).

Esperion Therapeutics Presents Full Results of Phase 2 Clinical Study Demonstrating that ETC-1002 Lowered LDL-C by an Average of 32 Percent and Was Well Tolerated in Patients with Hypercholesterolemia and History of Statin Intolerance; Nov. 18, 2013, available at https://www.esperion.com/news-releases/news-release-details/esperion-therapeutics-presents-full-results-phase-2-clinical-0.

Ezetimibe Tablets (Zetia) label (2012).

FDA Guidance For Industry: Drug Substance Chemistry, Manufacturing, and Controls Information, Aug. 6, 2010.

FDA Guidance For Industry: Manufacturing, Processing, or Holding Active Pharmaceutical Ingredients, Mar. 1998.

FDA Guidance for Industry: Q3A Impurities in New Drug Substances, Jun. 2008.

(56) References Cited

OTHER PUBLICATIONS

Fujiwara et al. (2005) "First-Principles and Direct Design Approaches for the Control of Pharmaceutical Crystallization," J. Process Control 15:493-504.

Gagne et al (2013) Efficacy and Safety of Ezetimibe Monotherapy in 6-10 Year Old Children with Heterozygous Familial or Nonfamilial Hypercholesterolemia; Journal of Clinical Lipidology 7(3):257-258.

Gribble, et al. (1996) "ATP-Citrate Lyase as a Target for the Hypolipidemic Intervention. Design and Synthesis of 2-Substituted Butanedioic Acids as Novel, Potent Inhibitors of the Enzyme," J. Med Chem. 39:3569-2584.

Gutierrez et al. (2014) "Efficacy and Safety of ETC-1002, a Novel Investigational Low-Density Lipoprotein-Cholesterol-Lowering Therapy for the Treatment of Patients With Hypercholesterolemia and Type 2 Diabetes Mellitus" Arteriosclerosis, Thrombosis & Vascular Biology 34:676-683.

Hamilton-Craig et al. (2010) "Combination Therapy of Statin and Ezetimibe for the Treatment of Familial Hypercholesterolemia," Vascular Health and Risk Management 6:1023-1037.

Hovingh et al. (2013) "Diagnosis and Treatment of Familial Hypercholesterolaemia," European Heart Journal 34:962-971.

ICH Harmonised Tripartite Guideline—Impurities in New Drug Substances Q3A(R2), Oct. 25, 2006.

ICH Harmonised Tripartite Guideline—Specifications: Test Procedures And Acceptance Criteria For New Drug Substances And New Drug Products: Chemical Substances Q6A, Step 4 version, Oct. 6, 1999.

ICH Harmonized Tripartite Guideline, Impurities in new drug substances Q3A(R2), (The International Council for Harmonization, Oct. 25, 2006).

Jacobs (1997) Ionic Species, in Understanding Organic Reaction Mechanisms 30-58 (Cambridge Univ. Press 1997).

Jones, Jr. (1997) The Chemistry of Alcohols Revisited and Extended: Glycols, Ethers, and Related Sulfur Compounds, in Organic Chemistry 817-876 (W. W. Norton & Company 1997).

Kastelein et al. (2013) "Efficacy and Safety of Ezetimibe Monotherapy in Children Six to Ten Years of Age With Heterozygous Familial or Non-Familial Hypercholesterolemia," JACC. 61(10) (10_Supplement) E1466.

Klencsár et al. (2017) "Development and validation of a novel quantification approach for gradient elution reversed phase high-performance liquid chromatography coupled to tandem ICP-mass spectrometry (RP-HPLC-ICP-MS/MS) and its application to diclofenac and its related compounds," Anal. Chim. Acta 974:43-53.

Klug (1993) The Influence of Impurities and Solvents on Crystallization, in Handbook of Industrial Crystallization 65-87 (A.S. Myerson ed., 1993).

Kumar et al. (2013) "Recent Analytical Method Developed by RP-HPLC," Global Journal of Pharmacology 7(3)232-240.

Lipka (2003) "Ezetimibe: a first-in-class, novel cholesterol absorption inhibitor," Cardiovascular Drug Reviews 21(4):293-312.

Lorimer (2011) "Oral Dosage Formulation Development"; available at https://www.almacgroup.com/wp-content/uploads/2015/02/Almac-Article_Achieving-faster-formulation-of-solid-oral-dosage-forms-for-FIH-supplies_Contract-Pharma_May-2011.pdf.

Masuda et al.(2009) "Ezetimibe improves postprandial hyperlipidaemia in patients with type IIb hyperlipidaemia" European Journal of Clinical Investigation 39:689698.

Mauro et al. (2003) "Ezetimibe for Management of Hypercholesterolemia," The Annuals of Pharmacotherapy 37:839-848.

Morris et al. (2003) "Ezetimibe for Hypercholesterolemia," American Family Physician 2 pages https://www.aafp.org/pubs/afp/issues/2003/1015/p1595.html.

Moynihan et al. (2017) "Impurity Occurrence and Removal in Crystalline Products from Process Reactions" Organic Process Research and Development 21(5):689-704.

Mueller et al. (2004) "Long Hydrocarbon Chain Keton Diols and Diacids that Favorably Alter Lipid Disorders in Vivo," J. Med. Chem. 47:6082-6099.

NCT01751984 (2012) "A Placebo-Controlled, Randomized, Double-Blind, Parallel Group, Multicenter Study to Evaluate the Efficacy and Safety of ETC-1002 in Subjects With Hypercholesterolemia and a History of Statin Intolerance".

NCT01941836 (2013) "A Randomized, Double-Blind, Parallel Group, Multicenter Study to Evaluate the Efficacy and Safety of ETC-1002, Ezetimibe, and the Combination in Hypercholesterolemic Patients With or Without Statin Intolerance".

NCT02666664 (2020) Evaluation of Long-Term Safety and Tolerability of ETC-1002 in High-Risk Patients with Hyperlipidemia and Higyh CV Risk (CLEAR Harmony).

NCT03067441 (2021) "Assessment of the Long-Term Safety and Efficacy of Bempedoic Acid (CLEAR Harmony OLE)".

Nikolic et al (2014) "ETC-1002: A Future Option for Lipid Disorders?" Astherosclerosis 237:705-710.

Oniciu et al., (2006) "Influence of Various Central Moieties on the Hypolipidemic Properties of Long Hydrocarbon Chain Diols and Diacids," American Chemical Society 49(1) (15 pages).

Patel et al. (2003) "Ezetimibe (Zetia): A New Type of Lipid-Lowering Agent," 16(3) Baylor University Medical Center Proceedings 16(3):354-358.

Phan et al (2012) "Ezetimibe therapy: mechanism of action and clinical update," Vascular Health & Risk Management 8:415-427.

Pinkosky et al., (2013) "AMP-activated protein kinase and ATP-citrate lyase are two distinct molecular targets for ETC-1002, a novel small molecule regulator of lipid and carbohydrate metabolism," J. Lipid Res. 54:134-151.

Pollex et al. (2008) "Emerging antidyslipidemic drugs," Expert Opinion Emerging Drugs 13(2):363-81.

Price (2018) "What Could Possibly Go Wrong in API Development," Pharmaceutical Outsourcing—The Journal of Pharmaceutical & Biopharm. 7 pages.

Robinson (2013) "Management of Familial Hypercholesterolemia: A Review of the Recommendations from the National Lipid Association Expert Panel on Familial Hypercholesterolemia," Journal of Managed Care Pharmacy 19(2):139-149.

Rose-Kahn (1985) "Inhibition of Lipid Synthesis by ββ'-Tetramethyl-substituted, C14-C22, α, ω-Dicarboxylic Acids in Cultured Rat Hepatocytes," The Journal of Biological Chemistry 260(14):8411-8415.

Rowe, et al., Handbook of Pharmaceutical Excipients, 6th Ed. (2009).

Steven A. Hardinger (1995) "A Simple Demonstration of the Effect of Impurities on Melting Point" J of Chemical Education 72:250.

T. Laird, Development and Scale-up of Processes for the Manufacture of New Pharmaceuticals, in Comprehensive Medicinal Chemistry 321-359 (Corwin Hansch et al. eds., 1990).

Tandon et al. (2003) "p-Toluenesulfonylmethyl Isocyanide: A Versatile Synthon in Organic Chemistry," Sulfur Reports 24(3):307-385.

Teramoto et al. (2013) "Familial Hypercholesterolemia," Journal of Atherosclerosis and Thrombosis 21(1):6-10.

Thompson et al. (2016) "Treatment with ETC-1002 alone and in combination with ezetimibe lowers LDL cholesterol in hypercholesterolemic patients with or without statin intolerance," Journal of Clinical Lipid 10:556-567.

Toth et al. (2010), A., Tomassini, J. E., & Tershakovec, A. M. (2010). "Update on the efficacy and safety of combination ezetimibe plus statin therapy," Clinical Lipidology, 5(5), 655-684.

Van der Graaf et al. (2008) "Efficacy and safety of coadministration of ezetimibe and simvastatin in adolescents with heterozygous familial hypercholesterolemia," Journal of the American College of Cardiology 52(17):1421-1429.

Van Leusen (1985) "On the synthesis of 1,n-diketones using monosubstituted derivatives of tosylmethyl isocyanide," Recl. Trav. Chim. Pays-Bas 104:50-53.

Van Leusen et al. (2001) "Synthetic Uses of Tosylmethyl Isocyanide (TosMIC)" Organic Reactions 417-679.

Vishwanath et al. (2014) "Familial Hypercholesterolemia and Estimation of US Patients Eligible for Low-Density Lipoprotein Apheresis after Maximally Tolerated Lipid-Lowering Therapy," Journal of Clinical Lipidology 8:18-28.

Vytorin (ezetimibe/simvastatin) label, Feb. 2004.

(56) References Cited

OTHER PUBLICATIONS

Yang et al. (2004) "Kilogram-Scale Synthesis of Bis(6-hydroxy-5,5-dimethylhexyl)ether (ESP24232), a Novel Lipid Lowering Agent" The New Journal for Organic Synthesis 36(6):587-596.

AbMole Bioscience, ETC-1002 (Bempedoic acid), 2 pages, retrieved on Mar. 10, 2021 from <http://www.abmole.com/products/etc-1002.html>.

Ackerly, et al., 1995, "A novel approach to dual-acting thromboxane receptor antagonist/synthase inhibitors based on the link of 1.3-dioxane-thrombaxane receptor antagonists and -thromboxane synthase inhibitors", J. Med. Chem. 38:1608-1628.

Acton, et al., 1996, "Identification of scavenger receptor SR-B1 as high density lipoprotein receptor", Science. 271(5248):518-20.

Ahrens, et al., 1967, "A direct method for preparing pyridoxal and 4-pyridoxic acid (1)", J. Heterocyl. Chem. 4:625-26.

Alexander, K., et al., 1948, "4.4-Dichlorodibutyl ether and its derivatives from tetrahydrofuran", J. Am. Chem. Soc. 70:1839-42.

*ApexBio Technology—ETC-1002 (Bempedoic acid)*, 4 pages, retrieved on Jul. 13, 2021 from <https://www.apexbt.com/etc-1002.html>.

Ark Pharma Scientific Limited—ETC-1002 (Bempedoic acid), 2 pages, retrieved on Jul. 13, 2021 from <<http://www.arkpharmtech.com/product/32890.html>>.

*AstaTech Inc., Bempedoic acid*, 1 page, retrieved on Jul. 13, 2021 from <https://www.astatechinc.com/CPSResult.php?CRNO-86963>.

Badimon, et al., 1992, "Role of High density lipoproteins in the regression of atherosclerosis", Circulation 85 (Suppl);11186-94.

Bailey, et al. "Convenient general method for the preparation of primary alkyllithiums by lithium-iodine exchange," (1990) J. Org. Chem. vol. 55, No. 19, pp. 5404-5406.

Barrans, et al., 1996, "Pre-beta HDL; structure and metabolism", Biochim, Biophys. Acta. 1300(2):73-85.

Becker, et al., 1982, "Intramolecular photoaddition of terminal allenes to conjugated cyclohexenones", J. Org. Chem. 47:3297-3310.

Beilstein Report for Compound Beilstein Registry No. 1741087, based in part on Crisan et al. (1956), Ann. Chim, (Paris), 13(1): 436-459.

Beilstein Report for Compound Beilstein Registry No. 1778991, based in part on Pechmann (1904), Chem. Ber., 37: 3819.

Beilstein Report for Compound Beilstein Registry No. 1784568, based in part on English (1941), *J. Am. Chem. Soc.*, 63 (4): 941-943.

Beilstein Report for Compound Beilstein Registry No. 2961112, based in part on Lardelli et al. (1967), *Recl. Trav. Chim.*, 86: 481-503.

Beilstein Report for Compound Beilstein Registry No. 5836264, based in part on Weber et al. (1992), *J. Med. Chem.*, 35(21): 3755-3773.

Beilstein Report for Compound Beilstein Registry No. 7473723, based in part on Rieke et al. (1996), *J. Org. Chem.*, 61(8): 2726-2730.

Beilstein Report for Compound, Beilstein Registry No. 5815199 based in part on Weber et al. (1992), *J. Med. Chem.*, 35(21): 3755-3773.

Bernady, et al. "Prostaglandins and congeners. 20. Synthesis of prostaglandins via conjugate addition of lithium trans-1-alkenyltrialkylalanate reagents. A novel reagent for conjugate 1,4-additions," *J. Org. Chem.* (1979) vol. 44, No. 9, pp. 1438-1447.

Bhanot, et al. "Synthetic studies on Terpenoids. 5. Syntheses of γ- and δ-Lactones from β-(2,7-Dimethyl-1,2-dihdroxycycloheptyl)propionic Acid," *J. Org. Chem.* (1977) vol. 42, pp. 1623-1627.

Bicking, et al., "11, 12-Secoprostaglandins. 1. Acylhydroxyalkanoic acids and related compounds", J. Med. Chem., 1977, pp. 35-43, vol. 20.

*BioChemPartner—Bempedoic acid*, 2 pages, retrieved on Jul. 13, 2021 from <http://www.biochempartner.com/738606-46-7-BCP16083>.

Bisgaier, et al., 1997, "Attenuation of plasma low density lipoprotein cholesterol by select 3-hydroxy-3-methylglutaryl coenzyme A reductase inhibitors in mice of low density lipoprotein receptors", J. Lipid Res. 38 (12):2502-2515.

Bisgaier, et al., 1998, "A novel compound that elevates high density lipoprotein and activates the peroxisome proliferator activated receptor", J. Lipid Res. 39(1):17-30.

Blatt ed., 1943, "Gilbert Sulfonation and Related Reactions" pp. 135-142, 160-165; Org. Synth. Coll. vol. II, Wiley, NY and Org. Synth. Coll. vol. IV, 1963, Wiley NY 529-531.

Blatt, et al., "The reducing action of Grignard reagent and the synthesis of tertiary aliphatic carbinols", J. Org. Chem., 1932, pp. 1495-1499, vol. 54.

Bongini, et al., 1979 "A simple and practical method for tetrahydropyranylation of alcohols and phenols", Synthesis 618-620.

Brown, et al. "Selective reductions. 26. Lithuim triethylborohydride as an exceptionally powerful and selective reducing agent in organic synthesis. Exploration of the reactions with selected organic compounds containing representative functional groups," J. Org. Chem. (1980) vol. 45, No. 1, pp. 1-12.

Brown, H. C. et al. "Hydroboration. 67. Cyclic hydroboration of acyclic alpha, omega-dienes with 9-borabicyclo[3.3.1 ]nonane/borane-dimethyl sulfide," J. Org. Chem. (1984) vol. 49, No. 6, pp. 1072-1078.

Brown, H. C. et al. "Selective reductions. VII. Reaction of lithium trimethoxyaluminohydride with selected organic compounds containing representative functional groups," J. Am. Chem. Soc. (1965) vol. 87, No. 24, pp. 5614-5620.

Bruce, et al., 1998, "Plasma lipid transfer proteins, high-density lipoproteins, and reverse cholesterol transport", Annu Rev Nutr. 1998;18:297-330.

Byrn et al., 1995, "Pharmaceutical Solids: A Strategic Approach to Regulatory Considerations," Pharmaceutical Research, 12(7):945-854.

Caira (1998) "Crystalline Polymorphism of Organic Compounds," Topics in Current Chemistry 198:163-208.

Campagna, et al., 1994, "Cyclic Amidine Analogues of Taurine and Homotaurine; Synthesis and Effects on Rat Skeletal Muscle", Farmaco, Ed. Sci 49:653-658.

Carothers et al., 1924, "Platinum oxide as a catalyst in the reduction of organic compounds. V. The preparation of primary alcohols by the catalytic hydrogenation of aldehydes," *J. Am. Chem. Soc.* 46:1675-83.

Cerny, et al., 1969, "Properties of Sodium Bis-(2-Methoxyethoxy)-Aluminum Hydride", Collect Czech Chem Comm. 34:1025-33.

Chadwick, et al., 1979, "Reaction between N-Alkylpyroles and Alkyllithium Reagents" J. Chem Soc., Perkin Trans. 12845.

ChemScene LLC, Bempedoic acid, 2 pages, retrieved on Mar. 10, 2021 from <http://abachemscene.com/738606-46-7.html>.

Chen, et al., 1998, "Asymmetric total synthesis of phosphatidylinositol 3-phosphate and 4-phosphate derivatives", J. Org. Chem. 63:6511-22.

Comins, et al., 1981, "A one pot synthesis of unsymmetrical secondary alcohols from two grignard reagents", Tetrahedron Lett. 22:1085-88.

Communication pursuant to Rule 114(2) EPC, observations by a third party concerning the patentability of an invention in European Patent Application No. 18211435.5 (published as EP 3 666 750 A1) by Sandoz AG, sent to applicant Jul. 22, 2020.

Corbridge, 1985, "Phosphorus: An Outline of its Chemistry, Biochemistry and Technology", Studies in Inorganic Chemistry, 3rd ed, pp. 357-395.

Corey, et al., 1967, "A useful method for the conversion of alcohols into iodides", J. Org. Chem. 32:4160-4161.

Corey, et al., 1979, "Useful procedures for the oxidation of alcohols involving pyridinum dichromate in aprotic media", Tetrahedron Lett. 5:399-402.

Cramer et al. "Effects of a novel dual lipid synthesis inhibitor and its potential utility in treating dyslipidemia and metabolic syndrome" J. Lipid Res.; 2004; 1289-1301.

(56) References Cited

OTHER PUBLICATIONS

Dalton, J.C. et al. (1971) "Type I and Type II Photochemical Reactions of Some Five- and Six-Membered Cycloalkanones," J. Am. Chem. Soc., 93 (26):7213-21.
Danheiser, et al., 1991, "A Practical and Efficient Method for Synthesis of β-Lactones", J. Org. Chem. 58:1176-65.
Dansky HM, Fisher Ea, 1999, "High-density lipoprotein and plaque regression: the good cholesterol gets even better", Circulation 100(17): 1762-3.
*DC Chemicals—Bempedoic acid*, 2 pages, retrieved on Jul. 13, 2021 from <https://www.dcchemicals.com/product_show-Bempedoic_Acid_ETC_1002_ESP_55016_.html>.
De Sarlo, et al., 1971, "Isoxazolin-5-one", J. Chem Soc. 88-89.
Decossin, et al., 1997, "Subclasses of LpA-I in coronary artery disease: distribution and cholesterol efflux ability", Eur J Clin Invest. 27(4):299-307.
*Drug Bank Online, Bempedoic acid*, 9 pages, retrieved on Jul. 12, 2021 from <https://go.drugbank.com/drugs/DB11936>.
Eaton, et al., 1972, "Hydroxypropylation", J. Org. Chem. 37:1947-50.
Ehlinger, et al., 1980, "Silicon in Synthesis. 10. The (trimethylsiyl) allyl Anion: A. beta-Acyl anion equivalent for the conversion of aldehydes and ketones into gamma-lactone", J. Am. Chem. Soc. 102:5004-11.
Eisch, et al. 1978, "Synthesis of lactones via the titanium-catalyzed hydromagnesiation of alkenols", J. Organomet. Chem. 160:C8-C12.
*eNovation Chemicals LLC—Bempedoic acid*, 1 pages, retrieved on Jul. 13, 2021 from <https://www.enovationchem.com/ProductDetails.asp?cellC=+bgcolor%3D%27%23E8F8FF%27+&ProductID=KP-43530>.
*Excenen PharmaTech—ETC-1002 (Bempedoic acid)*, 2 pages, retrieved on Jul. 13, 2021 from <https://excenen.com/searchresultlist.php?id=EX-A1243>.
Fielding & Fielding, 1995, "Molecular physiology of reverse cholesterol transport", J. Lipid Res. 36(2):211-28.
Filippov et al. "ETC-1002 Regulates Immune Response, Leukocyte Homing and Adipose Tissue Inflammation via LKB1-Dependent Activation of Macrophage AMPK." J. Lipid Res.; 2013; 54; 2095-2108.
Finkelstein, H. Ber. 1910, Dtsch. Chem. Ges., 43, 1528-15232.
Fraser, et al., 1985, "Acidity measurements in THF. V. Heteroaromatic compounds containing 5-membered rings", Can J. Chem. 63:3505-09.
Garegg, et al., 1980, "Novel Reagent System for converting a Hydroxy-group into an Iodo-group in carbohydrates with inversion of Configuration", J.C.S. Perkin I 2866-2868.
Gearing, et al., 1993, "Interaction of the peroxisome-proliferator-activated receptor and retinoid X receptor", Proc. Natl. Acad. Sci. USA 90(4):14440-1444.
Gigg, et al., 1967, "The Preparation of Unsymmetrical Diglycerides", J. Chem. Soc., C. 431-434.
Gleiter, R. et al. "Synthesis and properties of 4,4,9,9-tetramethyl-1-oxa-cycloundecane-5,6,7,8-tetrone and 5,5,10,10-tetramethyl-1-oxa-cyclotridecane-6,7,8,9-tetrone," *Chemistry—A European Journal* (1996) vol. 2, No. 3, pp. 271-277.
Gleiter, R. et al., "Synthesis of 5,5,10,10-tetramethyl-1-oxacyclotridecane-6,7,8,9-tetrone—on the mechanism of the Rubotom reaction," Eur. J. Org. Chem. (1995) No. 9, pp. 1655-1661.
Green and Kehinde, 1975, "An established predispose cell line and its differentiation in culture II. Factors affecting the adipose conversion", Cell. 5(1):19-27.
Greene, T.W., 1999, "Protection for the Hydroxyl Group, Including 1,2-and 1,3-Diols", Protective Groups in Organic Synthesis.
*Hangzhou MolCore BioPharmatech Co., Ltd.—Bempedoic acid*, 7 pages, retrieved on Jul. 13, 2021 from <https://www.molcore.com/product/738606-46-7>.
Harris and Kletzien, 1994, "Localization of pioglitazone response element in the adipocyte fatty acid-binding protein gene", Mol Pharmacol. 45(3):439-45.

Hayden and Ma, 1992, "Molecular genetics of human lipoprotein lipase deficiency", Mol Cell Biochem. 113(2):171-6.
Heyman, et al., 1992, "9-cis retinoic acid is high affinity ligand for the retinoid X receptor", Cell 68(2):397-406.
Hidaka and Fidge, 1992, "Affinity purification of the hepatic high-density lipoprotein receptor identifies two acidic glycoproteins and enables further characterization of their binding properties", Biochem. J. 15(Pt1):161-7.
Hilfiker et al., 2006, "Relevance of Solid-state Properties for Pharmaceutical Products," Polymorphism: in the Pharmaceutical Industry, pp. 1-19.
Hirano, et al., 1997, "Genetic cholesteryl ester transfer deficiency is extremely frequent in the Omagari area of Japan. Marked hyperalphalipoproteinema caused by CETP gene mutation is not associated with longevity", Arterioscler. Thromb. Vasc.Biol. 17(6):1053-1059.
Hoyer, et al., 1986, "Catalysis by acidic clay of the protective tetrahydropyranylation of alcohols and phenols", Synthesis 655-57.
Hudlicky, M., 1996, "Reduction of aldehydes and their derivatives", Reductions in Organic Chemistry, 2nd ed. pp. 137-139.
Hudlicky, M., 1996, "Reduction of esters and lactones of carboxylic acids", Reduction in Organic Chemistry 2nd ed. pp. 212-217.
Hunyadi et al. (2018) "Crystalline form of 8-hydroxy-2,2, 14, 14-tetramethylpentadecanedioic acid," 18(7A):1-9 (No. IPCOM00025443D).
International Search Report and Written Opinion, International Application No. PCT/US2020/038622, mailed on Nov. 25, 2020 (25 pages).
International Search Report and Written Opinion, International Application No. PCT/US2020/038624, mailed Sep. 15, 2020 (16 pages).
International Search Report and Written Opinion, International Application No. PCT/US2020/038624, mailed on Sep. 15, 2020 (15 pages).
International Search Report, International Application No. PCT/US2003/041411, mailed Dec. 8, 2004 (12 pages).
Ishibashi, et al., 1993, "Hypercholesterolemia in low density lipoprotein receptor knockout mice and its reversal by adenovirus-mediated gene delivery", J. Clin. Invest. 92(2):883-93.
Ishibashi, et al., 1994, "Massive xanthomatosis and atherosclerosis in cholesterol-fed low density lipoprotein receptor-negative mice", J. Clin Invest. 93(5):1885-93.
Ishii et al., 1983, "Catalytic Regioselective Dehydrogenation of Unsymmetrical alpha Omega-Diols Using Ruthenium Complexes", Tetrahedron Lett. 26:2677-2680.
Ishii, et al., 1986, "Ruthenium Complex Catalyzed Regioselective Dehydrogenation of Unsymmetrical alpha Omega-Diols", J. Org. Chem. 51:2034.
Isseman and Green, 1990, "Activation of a member of the steroid hormone receptor superfamily by peroxisome proliferators", Nature 347(6294):645-650.
Ito, et al., 2000, "Regio-and diastereocontrol in carbonyl allylation by 1-halobut-2-enes with Tin(II) halides", J Org Chem. 65(2):494-8.
Iwai, et al., 1966, "Studies on acetylenic compounds. XLIV. Synthesis of 3-aminoisoxazoles and 3-hydroxyisoxazoles (3-Isoxazolones)", Chem. Pharm. Bull. 14:1277-88.
Jetter, R., "Long-chain alkanediols from Myricaria germanica leaf cuticular waxes," Phytochemistry, 55 (2), 2000, pp. 169-176.
Johnston, et al., 1988, "A new, mild heterogeneous catalyst for the tetrahydropyranylation of alcohols and phenols", Synthesis 393-4.
Kanai, et al., 1995, "Catalytic Asymmetric Conjugate Addition of Grignard Reagents Mediated by Copper (I)-Chiral Bidentate Phosphine Complex", Tetrahedron Lett. 36:4275-4278.
Katritzky, et al., 1993, "Generation and Reactions of sp2-Carbanionic Centers in the Vicinity of Heterocyclic Nitrogen Atoms", *Adv. Het. Chem.* 56:155-303.
Keller and Wahli, 1993, "Peroxisome proliferator-activated receptors—A link between endocrinology and Nurition?" TEM, 4:291-295.
Keller, et al., 1993, "Fatty acids and retinoids control lipid metabolism through activation of peroxisome proliferator-activated receptor-retinoid X receptor heterodimers", Proc. Natl. Acad. Sci. USA 90(6):2160-2164.

(56) References Cited

OTHER PUBLICATIONS

Kessar, et al., 1997, "Lewis acid complexation of tertiary amines and related compounds: A strategy for a α-deprotonation and stereocontrol", Chem. Rev. 97:721-37.

Kletzein, et al., 1991, "Enhancement of adipocyte differentiation by an insulin-sensitizing agent", Mol Pharmacol 41(2):393-398.

Kliewer, et al., 1992, "Convergence of 9-cis retinoic acid and peroxisome proliferator signaling pathways through heterodimer formation of their receptors", Nature 27;358(6389):771-4.

Kurata, et al., 1998, "A candidate high density lipoprotein (HDL) receptor, HB2, with possible multiple functions shows sequence homology with adhesion molecules", J. Atherosclerosis and Thrombosis 4(3):112-7.

Kurz, et al., 1985, "Anomalous selectivities in methyl transfers to water: An explanation using free energy surfaces which model the effects of non-equilibrium solvation", Isr. J. Chem. 26:339-48.

Kurz, et al.. "Evidence for rate-determining solvation change in methyl transfer to water. Solvent dependence of H2O/D2O kinetic isotope effects," J. Am. Chem. Soc. (1986) vol. 108, pp. 2960-2968.

Lagrost, et al., 1996, "Opposite effects of cholesteryl ester transfer protein and phospholipid transfer protein on the size distribution of plasma high density lipoproteins. Physiological relevance in alcoholic patients", J. Biol. Chem.271(32):19058-65.

Landshultz, et al., 1996, "Regulation of scavenger receptor, class B, type I, a high density lipoprotein receptor, in liver and steroidogenic tissues of the rat", J. Clin. Invest. 98(4):984-995.

Larock, 1989, Comprehensive Organic Transformations; Ch. 6, VCH: New York, pp. 446-448.

Lazarow and Fujiki, 1985, "Biogenesis of peroxisomes", Annu Rev Cell Biol. 1:489-530.

Levin, et al., 1992, "9-cis retinoic acid stereoisomer binds and activates the nuclear receptor RXR alpha", Nature 355(6358):359-61.

Ludwig, et al., 1989, "Rapid and efficient synthesis of nucleoside 5'-0-(1-thiotriphosphates), 5'-triphosphates and 2',3'-Cyclophosphorothioates using 2-Chloro-4H-1,3,2-benzodioxaphosphorin-4-one", J. Org. Chem. 54:631-35.

Maddaford, et al., 1993, "A general asymmetric synthesis of (-)-alpha-Dimethylretrodendrin and its diastereomers", J. Org. Chem 58:4132-38.

March, J., 1992, Advanced Organic Chemistry: Reactions, Mechanisms, and Structure 4th ed., pp. 248-272, 1196-98, 437-438, 920-929.

Masamune, et al. "Tylonolide hemiacetal, the aglycone of tylosin, and its partial synthesis," J. Am. Chem. Soc. (1976) vol. 98, No. 24, pp. 7874-7875.

McCune et al., "Effect of Mevinolin on Cholesterol Metabolism in Obese and Lean Zucker Rats," Biochemical Pharmacology (1987) vol. 36, pp. 875-879. (abstract only).

MedChemExpress LLC, Bempedoic acid, 3 pages, retrieved on Mar. 10, 2021 from <https://www.medchemexpress.com/ETC-1002.html>.

Menger, et al., 1981, "Synthetically useful oxidations at solid sodium permanganate surfaces", Tetrahedron Lett. 22:1655-56.

Miyashita, et al., 1977, "Pyridinium .rho.-Toluenesulfonate. A mild and efficient catalyst for the tetrahydropyranylation of alcohols", J. Org. Chem 42:3772-74.

Mizukami, et al., 2015, "Halogen Exchange Reaction of Aliphatic Fluorine Compounds with Organic Halides as Halogen Source," Organic Letters 17:5942-5945.

Moffet, et al., 1963, "2-(1-Pyrrolidyl)Propanol", Org. Synth. Collect 4:834-5.

Mulzer, 1995, Comprehensive Organic Functional Group Transformations Oxford 5 pp. 161.

Musechem, Bempedoic acid, 6 pages, retrieved on Mar. 10, 2021 from <https://www.musechem.com/product/1004743.html>.

Myers, et al., 1992, "Studies on the thermal generation and reactivity of a class of (.alpha., .pi.)-1,4-biradicals", J. Am. Chem. Soc. 114:9369-86.

Nagano H., et al., "Stereoselectivity in the formation and radical reduction of cyclic bromoacetals, key intermediates for the synthesis of delta-hydroxy-and epilson-hydroxy-alpha-methylcarboxylic acid esters", Tetrahedron Letters, 2003, pp. 6867-6870, vol. 44, No. 36.

Nan F, et al., "Dual Function Glutamate-Related Ligands: Discovery of a Novel, Potent Inhibitor of Glutamate Carboxypeptidase II Possessing mGluR3 Agonist Activity" Journal of Medicinal Chemistry 2000, 43:pp. 772-774.

Nemali, et al., 1988, "Comparison of constitutive and Inducible levels of expression of paroxisomal beta-oxidation and catalase genes in liver and extrahepatic tissues of rat", Cancer Res. 48(18):5316-24.

Nystrom, et al., 1947, "Reduction of Organic Compounds by Lithium Aluminum Hyride", J. Am. Chem. Soc. 69:1197-1199.

Nystrom, et al., 1949, "Lithium borohydride as a reducing agent", J. Am. Chem. 71:3245-47.

Nystrom, et al., 1949, "Lithium Borohydride as a Reducing Agent", J. Am. Chem. Soc. 71:3245-48.

Ogata, et al., 1969, "Kinetics of the Baeyer-Villiger reaction of benzaldehydes with perbenzoic acid in aquoorganic solvents", J. Org. Chem. 34:3985-91.

Okamoto, et al., 1985, "Synthesis of Alkyl Dihydrogenphosphate by the Reaction of Alcohols and Silyl Polyphosphate", Bull Chem. Soc. Jpn. 58:3393-3394.

Olah, et al., 1979, "Transformations with Chlorotrimethylsilane/Sodium Iodide, a Convenient In Situ Iodotrimethylsilane Reagent", J. Org. Chem 44:8, 1247-1251.

Olah, et al., 1984, "N-Formylmorpholine: A New and Effective Formylating Agent for the Preparation of Aldehydes and Dialkyl(1-Formylalkyl)phosphonates from Grignard or Organolithium Reagents", J. Org. Chem. 49:3856-3857.

Olah, et al., 1987, "Formylating Agents", Chem. Rev. 87:4, 671-686.

Oster, et al., 1983, "Generation and Reactions of the Dianion of 3-Hydroxy-5-methylisoxazole, a convenient β-keto Amide Synthon", J. Org. Chem 48:4307-4311.

Parra, et al., 1992, "A case-control study of lipoprotein particles in two populations at contrasting risk for coronary heart disease. The ECTIM Study", Arterioscler Thromb. 12:701-707.

Plato et al., 1969, "Differential Scanning Calorimetry as a General Method for Determining the Purity and Heat of Fusion of High-Purity Organic Chemicals. Application to 95 Compounds," Analytical Chemistry, 41(2):330-336.

Pop, et al., 1997, "Allylic and Phenolic Phosphate Esters of Dexanabinol", Org. Prep. And Proc. Int. 29:341-347.

Ramirez, et al. "Phosphorylation by means of cyclic enediol phosphates," Acc. Chem. Res. (1978) vol. 11, pp. 239.

Raunio, et al., 1957, "Addition of Propargyl Acetal to Cyclohexanone in the Presence of Sodamide", J. Org. Chem 22:570.

Reaven, 1993, "Role of Insulin resistance in human disease (syndrome X): an expanded definition", Annu Rev Med. 44:121-31.

Reddy and Lalwani, 1983, "Carcinogenesis by hepatic peroxisome proliferators: evaluation of the risk of hypolipidemic drugs and industrial plasticizers to humans", Crit Rev Toxicol. 12(1):1-58.

Rigotti, et al., 1996, "Regulation by adrenocorticotropic hormone of the in vivo expression of scavenger receptor class B type I (SR-BI), a high density lipoprotein receptor, in steroidogenic cells of the murine adrenal", J. Biol. Chem. 1996, vol. 271(52):33545-9.

Robins and Fasulo, 1997, "High density lipoproteins, but not other lipoproteins, provide a vehicle for sterol transport to bile", J Clin Invest. 98(3):380-4.

Sam, et al., 1972, "Crown Polyether Chemistry, Potassium Permanganate Oxidations in Benzene", J. Am. Chem. Soc. 94:4024.

Saulnier, et al., 1982, "Generation and Reactions of 3-Lithio-1-(phenylsulfonyl) Indole", J. Org. Chem 47:757.

Schaper, U.A. (1980) "Die gemischte Guerbet-Reaktion zwischen cyclischen und acyclischen Alkoholen," Fette, Seifen, Anstrichmittel, Industrieverlag von Hernhaussen kg, 82 (11): 454-456.

Selleck Chemicals, ETC-1002 (Bempedoic acid), 3 pages, retrieved on Mar. 10, 2021 from <https://www.selleckchem.com/products/etc-1002.html>.

(56) References Cited

OTHER PUBLICATIONS

Shirley, et al., 1995, "Metalation of pyrrole, 1-methylpyrrole, and 1-phenylpyrrole with n-Butyllithium", J. Org. Chem 20:225-31.

Sianesi, et al., 1971, "2.4-dihydro-1H-2.1-, 3.4-Dihydro-2H-1.2-und. 3.4-Dihydro-1H-2.3-benzothiazin-S.S-dioxid", Chem. Ber. 104:1880-91.

Silverman, The Organic Chemistry of Drug Design and Drug Interaction, 1992, pp. 15-22.

Skinner, et al., 1995, "Benzoylcyanamide from ethyl benzoylitioncarbomate", J. Am. Chem. Soc. 77:5440-42.

Smith, et al., 1957, "Nitrogen Compounds of the phosphoric and Phosphonic Acids, III, Preparation and Properties of Amides of Phenylphosphonic and Phenylphosphonothiolic Acids", J. Org. Chem. 22:265-267.

Song, et al., 1999, "Practical asymmetric synthesis of an endothelin receptor antagonist", J. Org. Chem. 64:9658-67.

Staels and Auwerx, 1998, "Regulation of apo A-I gene expression by fibrates", Atherosclerosis 137 Suppl:S19-23.

Stevens, et al., 1982, "Further studies on the utility of sodium hypochlorite in organic synthesis Selective oxidation of diols and direct conversion of aldehydes to esters," Tetrahedron Lett. 23:4647-4650.

Stowell, et al., 1995, "A new method for the phosphorylation of alcohols and phenols", Tetrahedron Lett. 36(11):1825-26.

Sundararaman, et al., 1978, "One step conversion of aldehydes to esters", Tetrahedron Lett. 19:1627-1628.

Sweeney, 1995, "Comprehensive Organic Functional Group Transformations", Oxford, vol. 2, pp. 104-109.

Taravel, et al., 1988, "Interglycosidic 13C-1H Coupling Constants", Tetrahedron Lett. 29:199-200.

Target Molecule Corp. (TargetMol), ETC1002 (Bempedoic acid), 3 pages, retrieved on Mar. 10, 2021 from <https://www.targetmol.com/compound/ETC1002>.

Thums et al., "Epoxidation—a Consequence of Cell Damage," Chemical Monthly, 128 (4), 1997, pp. 411-420.

Tontonoz, et al., 1994, "Adipocyte-specific transcription factor ARF6 is a heterodimeric complex of two nuclear hormone receptors, PPAR gamma and RXR alpha", Nucleic Acids Res. 22(5):5628-34.

*Toronto Research Chemicals—Bempedoic acid*, 5 pages, retrieved on Jul. 13, 2021 from <https://www.trc-canada.com/product-detail/?B119700>.

Uhlmann, et al., 1986, "Chemical 5'-phosphorylation of oligonucleotides valuable in automated DNA synthesis", Tetrahedron Lett. 27:1023-26.

Ulrich, et al., 1995, "Cultured hepatocytes as investigational models for hepatic toxicity: practical applications in drug discovery and development", Toxicol Lett. 82/83:107-15.

Urata, et al., 1991, "Transition metal complex catalyzed carbonylation of organic halides in the presence of molecular sieves instead of base," Tetrahedron Lett. 32:36, 4733-36.

Vamecq and Draye, 1989, "Pathophysiology of peroxisomal beta-oxidation", Essays Biochem 24:115-225.

Vippagunta, S et al., "Crystalline Solids," *Advanced Drug Delivery Reviews* (2001) vol. 48, pp. 2-26. (abstract only).

Vogtle, et al., 1987, "Doubly Clamped Cope Systems", J. Org. Chem. 52:5560-5564.

Williams, et al., 1988, "Bromine as an oxidant for direct conversion of aldehydes to esters", Tetrahedron Lett. 29:5087-90.

Wilson, et al., 1982, "A novel, nonoxidative method for the conversion of aldehydes to esters", J. Org. Chem. 47:1360-61.

Wroblewski and Ladue, 1995, "Lactic dehydrogenase activity in blood", Proc. Soc. Exp. Biol. Med. 90:210-213.

Xu, et al., 1989, "The retinoblastoma susceptibility gene product: a characteristic pattern in normal cells and abnormal expression in malignant cells", Onocogene 4: 807-812.

Yamamoto, "Asymmetric synthesis of 5-and 6-membered lactones from cyclic substrates bearing a C2-chiral auxiliary", J. Org. Chem., 1991, pp. 1112-1119, vol. 35, No. 21.

Yanagisawa, et al., 1994, "Allylbarium Reagents: Unprecedented regio- and stereoselective allylation reactions of carbonyl compounds", J. Am. Chem. Soc. 116:6130-6141.

Yu, et al., 1988, "A novel reagent for the synthesis of myo-inositol phosphates: N,N-diisopropyl dibenzyl phosphoramidite", Tetrahedron Lett. 29:979-82.

Yunker, et al., 1978, "Alpha-oxygenated fatty acids occurring as amides of 2-methylene beta-alanine in a marine sponge", Tetrahedron Lett. 47:4651-52.

METHODS OF MAKING BEMPEDOIC ACID AND COMPOSITIONS OF THE SAME

CROSS-REFERENCE

This application is a continuation of U.S. patent application Ser. No. 17/577,829, filed on Jan. 18, 2022, which is a continuation of U.S. patent application Ser. No. 17/150,321, filed on Jan. 15, 2021, which is a continuation of International Application No. PCT/US2020/038622, with an international filing date of Jun. 19, 2020, which international application claims the benefit of and priority to U.S. Patent Application No. 62/864,873, filed on Jun. 21, 2019, the entire contents of which are incorporated by reference herein.

BACKGROUND

The development of robust, cost-effective and efficient manufacturing methods for the production of pharmaceutically active compounds with desired yield and purity remains a significant challenge. Bempedoic acid (8-hydroxy-2,2,14,14-tetramethylpentadecanedioic acid) is a compound under development for the treatment of a wide variety of diseases including liver disorders and cardiovascular disease. Accordingly, a process for synthesizing bempedoic acid (8-hydroxy-2,2,14,14-tetramethylpentadecanedioic acid) is desired, whereby the product has purity and impurity profiles required by regulatory agencies for the production of a commercializable drug product.

SUMMARY

The inventors have discovered an efficient process for producing high purity bempedoic acid, as well as highly pure, stable forms of bempedoic acid suitable for use as an active pharmaceutical ingredient.

In one aspect, the invention provides methods of preparing a compound of formula (V):

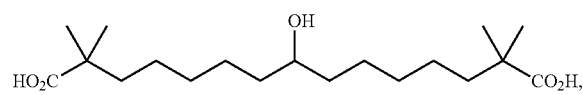

or a pharmaceutically acceptable salt thereof. The compound of formula (V), or a pharmaceutically acceptable salt thereof, can be of high purity. Accordingly, in certain embodiments, the invention provides methods of preparing a pharmaceutical material comprising a compound of formula (V), or a pharmaceutically acceptable salt thereof, where the pharmaceutical material includes the compound of formula (V), or a pharmaceutically acceptable salt thereof, in an amount greater than 99.0% by weight based on the total weight of the pharmaceutical material.

In various embodiments of the invention, the method generally comprises:
(a) contacting ethyl isobutyrate with a substituted 5-chloropentane in the presence of a first base to form a compound of formula (I):

wherein the substituted 5-chloropentane is selected from the group consisting of 1-bromo-5-chloropentane and 1-iodo-5-chloropentane;
(b) contacting the compound of formula (I) with a salt of formula [M]$^+$[X]$^-$ to form a compound of formula (II):

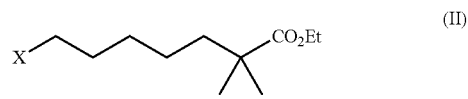

wherein [M]$^+$ is selected from the group consisting of Li$^+$, Na$^+$ and K$^+$, wherein [X]$^-$ is selected from the group consisting of Br$^-$ and I$^-$;
(c) contacting the compound of formula (II) with toluenesulfonylmethyl isocyanide in the presence of a second base to form a first intermediate, and contacting the first intermediate with an acid to form a compound of formula (IV):

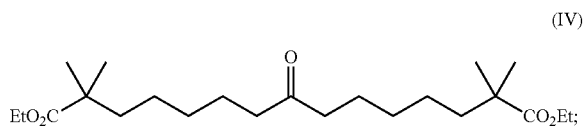 [SMILES: CCOC(=O)C(C)(C)CCCCCC(=O)CCCCCC(C)(C)C(=O)OCC]

and
(d) contacting the compound of formula (IV) with a reducing agent to form a second intermediate, and contacting the second intermediate with a hydrolyzing base to form a compound of formula (V), or a pharmaceutically acceptable salt thereof.

In certain embodiments of the invention, the method comprises:
(a) contacting 1-bromo-5-chloropentane with about 1 to about 1.21 molar equivalents of ethyl isobutyrate in the presence of lithium diisopropylamide at a temperature in the range of about −20° C. to about 0° C. to form a compound of formula (I):

(b) contacting the compound of formula (I) with about 1.1 molar equivalents of sodium iodide in 2-butanone at a temperature in the range of about 78° C. to about 82° C. to form a compound of formula (IIa):

(c) contacting the compound of formula (IIa) with toluenesulfonylmethyl isocyanide in the presence of sodium tert-pentoxide in dimethylacetamide at a temperature in the range of about −20° C. to about 10° C. to form an intermediate, and contacting the intermediate with an acid at a temperature in the range of about −10° C. to about 35° C. to form a compound of formula (IV):

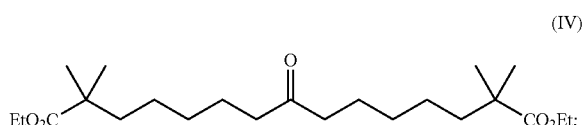

(IV)

and (d) contacting the compound of formula (IV) with about 0.35 molar equivalents of sodium borohydride to form a second intermediate, and contacting the second intermediate with sodium hydroxide in a solution to form a compound of formula (V).

In certain embodiments of the invention, the method further comprises:

(e) purifying the compound of formula (V) to provide a pharmaceutical material comprising a purified amount of the compound of formula (V).

In certain embodiments of the invention, purifying the compound of formula (V) comprises:

(f) adjusting the pH of the solution comprising the compound of formula (V) to about 6;
(g) extracting the compound of formula (V) from the solution using methyl tert-butyl ether to provide a methyl tert-butyl ether solution comprising the compound of formula (V);
(h) exchanging the methyl tert-butyl ether of the methyl tert-butyl ether solution with ethyl acetate to provide an ethyl acetate solution comprising the compound of formula (V);
(i) filtering the ethyl acetate solution comprising the compound of formula (V) through silica gel;
(j) crystallizing the compound of formula (V) using ethyl acetate and water to provide a crystalline form of the compound of formula (V); and
(k) recrystallizing the crystalline form of the compound of formula (V) using ethyl acetate and water to provide a pharmaceutical material comprising a purified amount of the compound of formula (V).

In another aspect, the invention provides high purity or purified bempedoic acid, or a pharmaceutically acceptable salt thereof. For example, described herein are pharmaceutical materials comprising a compound of formula (V):

(V)

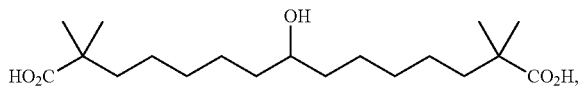

or a pharmaceutically acceptable salt thereof, wherein the pharmaceutical material comprises the compound of formula (V), or a pharmaceutically acceptable salt thereof, in an amount greater than 99.0% by weight based on the total weight of the pharmaceutical material.

In various embodiments, the pharmaceutical material comprises a crystalline form of the compound of formula (V), or a pharmaceutically acceptable salt thereof. In some embodiments, the pharmaceutical material comprises the compound of formula (V) in an amount greater than 99.0% by weight based on the total weight of the pharmaceutical material.

In another aspect, the invention provides pharmaceutical compositions or formulations including high purity bempedoic acid, or a pharmaceutically acceptable salt thereof, such as the pharmaceutical materials described herein. For example, a pharmaceutical composition can include a pharmaceutical material of the invention (e.g., a pharmaceutical material comprising the compound of formula (V), or a pharmaceutically acceptable salt thereof, in an amount greater than 99.0% by weight based on the total weight of the pharmaceutical material); and a pharmaceutically acceptable excipient. In some embodiments, a pharmaceutical composition can include a therapeutically effective amount of a pharmaceutical material of the invention; and a pharmaceutically acceptable excipient. In certain embodiments, the pharmaceutical composition comprises a crystalline form of the compound of formula (V), or a pharmaceutically acceptable salt thereof; and a pharmaceutically acceptable excipient.

Purified bempedoic acid, or a pharmaceutically acceptable salt thereof; a crystalline form of bempedoic acid, or a pharmaceutically acceptable salt thereof; a pharmaceutical material of the invention (e.g., a pharmaceutical material comprising the compound of formula (V), or a pharmaceutically acceptable salt thereof, in an amount greater than 99.0% by weight based on the total weight of the pharmaceutical material); or a pharmaceutical composition of the invention can be used in treating the various conditions and diseases described herein. For example, the methods of treatment can include inhibiting adenosine triphosphate citrate lyase (ACL), inhibiting cholesterol synthesis, and/or suppressing fatty acid biosynthesis. In some embodiments, the condition or disease can be hyperlipidemia such as primary hyperlipidemia and the methods include treating hyperlipidemia such as primary hyperlipidemia. In some embodiments, the disease can be cardiovascular disease and the methods include treating cardiovascular disease. In various embodiments, the methods of treatment can include improving or lowering low density lipid cholesterol (LDL-C), non-high density lipid cholesterol (non-HDL-C), total serum cholesterol (TC), apolipoprotein B (apoB), and/or high sensitivity C-reactive protein (hsCRP).

DETAILED DESCRIPTION OF THE INVENTION

Figure 1:
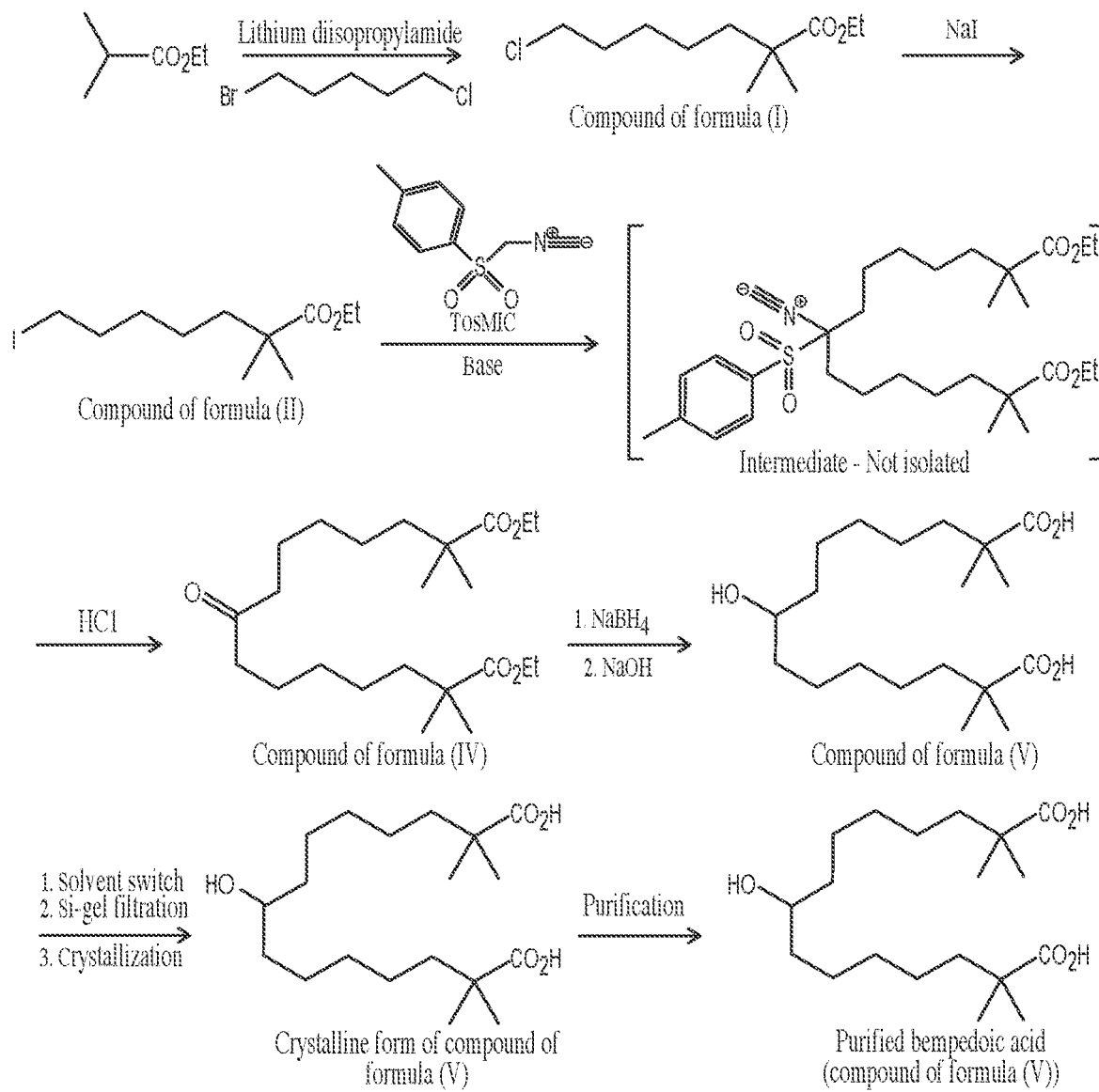
FIG. 1 is an exemplary reaction scheme of the invention for the synthesis of bempedoic acid (i.e., a compound of formula (V)) as described in Example 1, which reaction scheme includes the synthesis of a pharmaceutical material comprising the compound of formula (V) in an amount greater than 99.0% by weight based on the total weight of the pharmaceutical material.

It has now been discovered that bempedoic acid, including pharmaceutically acceptable salts thereof, can be prepared with high purity and/or in bulk quantities. In various embodiments, a crystalline form of bempedoic acid, or a pharmaceutically acceptable salt thereof, is provided.

The methods for preparing bempedoic acid described herein can provide a pharmaceutical material containing a high level or amount of bempedoic acid, or a pharmaceutically acceptable salt thereof, in part, due to the control of the formation of hard-to-remove impurities during the synthetic process.

In addition, a pharmaceutical material with a high purity crystalline form of bempedoic acid, or a pharmaceutically acceptable salt thereof, is provided, for example, where the pharmaceutical material comprises the crystalline form of bempedoic acid, or a pharmaceutically acceptable salt thereof, and wherein the pharmaceutical material comprises bempedoic acid, or a pharmaceutically acceptable salt thereof, in an amount greater than 99.0% by weight based on the total weight of the pharmaceutical material.

I. Definitions

To facilitate an understanding of the present invention, a number of terms and phrases are defined below.

Unless defined otherwise, all technical and scientific terms used herein have the same meaning as commonly understood by one of ordinary skill in the art to which this invention belongs. The abbreviations used herein have their conventional meaning within the chemical and biological arts. The chemical structures and formulae set forth herein are constructed according to the standard rules of chemical valency known in the chemical arts.

Throughout the description, where compositions and kits are described as having, including, or comprising specific components, or where processes and methods are described as having, including, or comprising specific steps, it is contemplated that, additionally, there are compositions and kits of the present invention that consist essentially of, or consist of, the recited components, and that there are processes and methods according to the present invention that consist essentially of, or consist of, the recited processing steps.

In the application, where an element or component is said to be included in and/or selected from a list of recited elements or components, it should be understood that the element or component can be any one of the recited elements or components, or the element or component can be selected from a group consisting of two or more of the recited elements or components.

Further, it should be understood that elements and/or features of a composition or a method described herein can be combined in a variety of ways without departing from the spirit and scope of the present invention, whether explicit or implicit herein. For example, where reference is made to a particular compound, that compound can be used in various embodiments of compositions of the present invention and/or in methods of the present invention, unless otherwise understood from the context. In other words, within this application, embodiments have been described and depicted in a way that enables a clear and concise application to be written and drawn, but it is intended and will be appreciated that embodiments may be variously combined or separated without parting from the present teachings and invention(s). For example, it will be appreciated that all features described and depicted herein can be applicable to all aspects of the invention(s) described and depicted herein.

The articles "a" and "an" are used in this disclosure to refer to one or more than one (i.e., to at least one) of the grammatical object of the article, unless the context is inappropriate. By way of example, "an element" means one element or more than one element.

The term "and/or" is used in this disclosure to mean either "and" or "or" unless indicated otherwise.

It should be understood that the expression "at least one of" includes individually each of the recited objects after the expression and the various combinations of two or more of the recited objects unless otherwise understood from the context and use. The expression "and/or" in connection with three or more recited objects should be understood to have the same meaning unless otherwise understood from the context.

The use of the term "include," "includes," "including," "have," "has," "having," "contain," "contains," or "containing," including grammatical equivalents thereof, should be understood generally as open-ended and non-limiting, for example, not excluding additional unrecited elements or steps, unless otherwise specifically stated or understood from the context.

Where the use of the term "about" is before a quantitative value, the present invention also includes the specific quantitative value itself, unless specifically stated otherwise. As used herein, the term "about" refers to a ±10% variation from the nominal value unless otherwise indicated or inferred from the context.

Where a molecular weight is provided and not an absolute value, for example, of a polymer, then the molecular weight should be understood to be an average molecule weight, unless otherwise stated or understood from the context.

It should be understood that the order of steps or order for performing certain actions is immaterial so long as the present invention remain operable. Moreover, two or more steps or actions may be conducted simultaneously.

At various places in the present specification, variable or parameters are disclosed in groups or in ranges. It is specifically intended that the description include each and every individual subcombination of the members of such groups and ranges. For example, an integer in the range of 0 to 40 is specifically intended to individually disclose 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40, and an integer in the range of 1 to 20 is specifically intended to individually disclose 1, 2, 3, 4, 5, 6, 7, 8, 9, 10, 11, 12, 13, 14, 15, 16, 17, 18, 19, and 20.

The use of any and all examples, or exemplary language herein, for example, "such as" or "including," is intended merely to illustrate better the present invention and does not pose a limitation on the scope of the invention unless claimed. No language in the specification should be construed as indicating any non-claimed element as essential to the practice of the present invention.

As a general matter, compositions specifying a percentage are by weight unless otherwise specified. Further, if a variable is not accompanied by a definition, then the previous definition of the variable controls.

As used herein, "pharmaceutically acceptable salt" refers to any salt of an acidic or a basic group that may be present in a compound of the present invention, which salt is compatible with pharmaceutical administration. For example, one or both of the carboxylic acid groups of bempedoic acid can be transformed to pharmaceutically acceptable salt(s).

As is known to those of skill in the art, "salts" of compounds may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic and benzenesulfonic acid.

Other acids, such as oxalic, while not in themselves pharmaceutically acceptable, may be employed in the preparation of salts useful as intermediates in obtaining the compounds described herein and their pharmaceutically acceptable acid addition salts.

Examples of bases include, but are not limited to, alkali metal (e.g., sodium and potassium) hydroxides, alkaline earth metal (e.g., magnesium and calcium) hydroxides, ammonia, and compounds of formula $NW_4^+$, wherein W is $C_{1-4}$ alkyl, and the like.

Examples of salts include, but are not limited, to acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like.

Other examples of salts include anions of the compounds of the present invention compounded with a suitable cation such as $Na^+$, $K^+$, $Ca^{2+}$, $NH_4^+$, and $NW_4^+$ (where W can be a $C_{1-4}$ alkyl group), and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

As used herein, "pharmaceutical composition" or "pharmaceutical formulation" refers to the combination of an active agent with a carrier, inert or active, making the composition especially suitable for diagnostic or therapeutic use in vivo or ex vivo.

The phrases "pharmaceutically acceptable" and "pharmacologically acceptable," as used herein, refer to compounds, molecular entities, compositions, materials, and/or dosage forms that do not produce an adverse, allergic or other untoward reaction when administered to an animal, or a human, as appropriate. For human administration, preparations should meet sterility, pyrogenicity, and general safety and purity standards as required by FDA Office of Biologics standards. "Pharmaceutically acceptable" and "pharmacologically acceptable" can mean approved or approvable by a regulatory agency of the federal or a state government or the corresponding agency in countries other than the United States, or that is listed in the U.S. Pharmacopoeia or other generally recognized pharmacopoeia for use in animals, and more particularly, in humans.

As used herein, "carrier" refers to a material, composition or vehicle, such as a liquid or solid filler, diluent, excipient, solvent or encapsulating material, involved in carrying or transporting a pharmaceutical agent such as bempedoic acid, or a pharmaceutically acceptable salt thereof, from one organ, or portion of the body, to another organ, or portion of the body.

As used herein, "pharmaceutically acceptable excipient" refers to a substance that aids the administration of an active agent to and/or absorption by a subject and can be included in the compositions of the present invention without causing a significant adverse toxicological effect on the patient.

Non-limiting examples of pharmaceutically acceptable excipients include water, NaCl, normal saline solutions, such as a phosphate buffered saline solution, emulsions (e.g., such as an oil/water or water/oil emulsions), lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. For examples of excipients, see Martin, Remington's Pharmaceutical Sciences, 15th Ed., Mack Publ. Co., Easton, PA (1975).

As used herein, "treating" or "treatment" includes any effect, for example, lessening, reducing, modulating, ameliorating or eliminating, that results in the improvement of the condition, disease, disorder, and the like, or ameliorating a symptom thereof. Treating can be curing, improving, or at least partially ameliorating the disorder. In certain embodiments, treating is curing the disease.

As used herein, "reducing" or "reduction" of a symptom or symptoms (and grammatical equivalents of this phrase) means decreasing of the severity or frequency of the symptom(s), or elimination of the symptom(s).

As used herein, "effective amount" or "therapeutically-effective amount" refers to the amount of a compound (e.g., a compound of the present invention) sufficient to effect beneficial or desired results. An effective amount can be administered in one or more administrations, applications or dosages and is not intended to be limited to a particular formulation or administration route. As used herein, the term "treating" includes any effect, e.g., lessening, reducing, modulating, ameliorating or eliminating, that results in the improvement of the condition, disease, disorder, and the like, or ameliorating a symptom thereof.

As used herein, "subject" and "patient" are used interchangeably and refer to an organism to be treated by the methods and compositions of the present invention. Such organisms are preferably a mammal (e.g., human, mouse, rat, guinea pig, dog, cat, horse, cow, pig, or non-human primate, such as a monkey, chimpanzee, baboon, and rhesus), and more preferably, a human.

As used herein, "disease," "disorder," "condition," or "illness," can be used interchangeably unless otherwise underacted or understood from the context, refers to a state of being or health status of a patient or subject capable of being treated with a compound, pharmaceutical materials, pharmaceutical composition, or method provided herein. In some embodiments, the compounds and methods described herein comprise reduction or elimination of one or more symptoms of the disease, disorder, or condition, or illness e.g., through administration of the compound of formula (V), or a pharmaceutically acceptable salt thereof.

As used herein, "administering" means oral administration, administration as a suppository, topical contact, intravenous, parenteral, intraperitoneal, intramuscular, intralesional, intrathecal, intracranial, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arterial, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies (e.g., anti-cancer agent, chemotherapeutic, or treatment for a neurodegenerative disease). The compound of the invention can be administered alone or can be co-administered to the patient. Co-administration is meant to include simultaneous or sequential administration of the compound individually or in combination (more than one compound or agent). Thus, the preparations can also be combined, when desired, with other active substances (e.g., to reduce metabolic degradation).

As used herein, "liver disorder" refers generally to a disease, a disorder, and/or a condition affecting the liver, and may have a wide range of severity encompassing, for example, simple accumulation of fat in the hepatocytes (steatosis), macrovescicular steatosis, periportal and lobular inflammation (steatohepatitis), cirrhosis, fibrosis, liver cancers, and liver failure.

As used herein, "fatty liver disease" ("FLD"), which is also called "fatty liver," refers to a disease leading to liver injury caused by abnormal fat accumulation in liver cells. FLD may arise from a number of sources, including excessive alcohol consumption and metabolic disorders, such as those associated with insulin resistance, obesity, and hypertension.

As used herein, "non-alcoholic fatty liver disease" ("NAFLD") refers to the spectrum of disorders resulting from an accumulation of fat in liver cells in individuals with no history of excessive alcohol consumption. In the mildest form, NAFLD refers to hepatic steatosis.

As used herein, "drug-induced liver disease" or "toxic liver injury" refers to a disease or a condition in which an active agent has caused injury to the liver.

As used herein, "alcoholic liver disease," also called "alcoholic liver injury," refers to a disease caused by fat accumulation in liver cells, caused at least in part by alcohol ingestion. Examples include, but are not limited to, diseases such as alcoholic simple fatty liver, alcoholic steatohepatitis ("ASH"), alcoholic hepatic fibrosis, alcoholic cirrhosis, alcoholic fatty liver disease, and the like. It should be noted that alcoholic steatohepatitis is also called alcoholic fatty hepatitis and includes alcoholic hepatic fibrosis.

As used herein, "fatty liver of pregnancy" refers to acute fatty liver conditions that can arise during pregnancy and can be life-threatening.

As used herein, "altering lipid metabolism" refers to an observable (measurable) change in at least one aspect of lipid metabolism, including but not limited to total blood lipid content, blood HDL cholesterol, blood LDL cholesterol, blood VLDL cholesterol, blood triglyceride, blood Lp(a), blood apo A-I, blood apo E and blood non-esterified fatty acids.

As used herein, "altering glucose metabolism" refers to an observable (measurable) change in at least one aspect of glucose metabolism, including but not limited to total blood glucose content, blood insulin, the blood insulin to blood glucose ratio, insulin sensitivity, and oxygen consumption.

As used herein, "purified bempedoic acid" means that, when isolated as a solid, a pharmaceutical material contains at least 95% by weight of 8-hydroxy-2,2,14,14-tetramethylpentadecanedioic acid based on the total weight of the pharmaceutical material. In certain embodiments, purified bempedoic acid means that, when isolated as a solid, a pharmaceutical material contains at least 99.0% by weight of 8-hydroxy-2,2,14,14-tetramethylpentadecanedioic acid based on the total weight of the pharmaceutical material. In addition, purified bempedoic acid can include a pharmaceutically acceptable salt thereof, unless stated otherwise or understood from the context.

As used herein, a reaction that is "substantially complete" means that the reaction contains more than about 80% by weight of the desired product. In certain embodiments, a substantially complete reaction contains more than about 90% by weight of the desired product. In certain embodiments, a substantially complete reaction contains more than about 95% by weight of the desired product. In certain embodiments, a substantially complete reaction contains more than about 97% by weight of the desired product.

Unless stated otherwise, all X-ray powder diffraction (XRPD) patterns described herein correspond to XRPD patterns measured using a Cu Kα radiation source, and the crystalline forms of bempedoic acid are analyzed by XRPD at ambient temperature.

II. Crystalline Forms of Bempedoic Acid

A. Crystalline Bempedoic Acid

In one aspect, the invention provides a crystalline form of 8-hydroxy-2,2,14,14-tetramethylpentadecanedioic acid, which is also known as and referred to herein as "bempedoic acid" and/or a compound of formula (V):

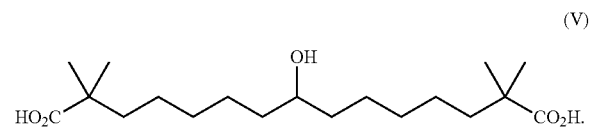 [SMILES: CC(C)(CCCCCC(O)CCCCCC(C)(C)C(=O)O)C(=O)O]

(V)

In certain embodiments, the crystalline form of the compound of formula (V) may be characterized by an X-ray powder diffraction pattern comprising peaks at the following diffraction angles (2θ): 10.3±0.2, 10.4±0.2, 17.9±0.2, 18.8±0.2, 19.5±0.2, and 20.7±0.2. In certain embodiments, the crystalline form of the compound of formula (V) may be characterized by an X-ray powder diffraction pattern comprising peaks at the following diffraction angles (2θ): 10.3±0.2, 10.4±0.2, 17.6±0.2, 17.9±0.2, 18.8±0.2, 19.5±0.2, 19.7±0.2, 20.4±0.2, 20.7±0.2 and 22.6±0.2.

In certain embodiments, the crystalline form of the compound of formula (V) is characterized by the X-ray powder diffraction pattern expressed in terms of diffraction angle 2θ, and optionally inter-planar distances d, and relative intensity (expressed as a percentage with respect to the most intense peak) as set forth in Table 1.

TABLE 1

X-ray Powder Diffraction Data of the Crystalline
Form of the Compound of Formula (V)

| Angle [2θ] | d-spacing [Å] | Relative Intensity [%] |
|---|---|---|
| 5.2 | 16.84 | 2.33 |
| 10.3 | 8.61 | 70.75 |
| 10.4 | 8.48 | 78.65 |
| 11.8 | 7.51 | 2.88 |
| 13.7 | 6.44 | 2.72 |
| 15.5 | 5.73 | 8.08 |
| 15.6 | 5.67 | 7.16 |
| 17.3 | 5.12 | 8.20 |

TABLE 1-continued

X-ray Powder Diffraction Data of the Crystalline
Form of the Compound of Formula (V)

| Angle [2θ] | d-spacing [Å] | Relative Intensity [%] |
|---|---|---|
| 17.6 | 5.04 | 18.72 |
| 17.9 | 4.95 | 100.00 |
| 18.8 | 4.73 | 42.30 |
| 19.5 | 4.55 | 21.42 |
| 19.7 | 4.51 | 15.07 |
| 20.4 | 4.35 | 16.93 |
| 20.7 | 4.29 | 23.95 |
| 21.1 | 4.21 | 5.78 |
| 22.0 | 4.05 | 13.87 |
| 22.6 | 3.94 | 17.54 |
| 23.1 | 3.84 | 7.78 |
| 23.6 | 3.78 | 4.97 |
| 23.9 | 3.73 | 6.19 |
| 24.7 | 3.60 | 1.98 |
| 25.8 | 3.46 | 3.04 |
| 26.3 | 3.39 | 2.10 |
| 27.5 | 3.24 | 13.36 |
| 29.2 | 3.06 | 3.86 |
| 30.2 | 2.96 | 1.27 |
| 30.8 | 2.90 | 5.34 |
| 31.3 | 2.86 | 1.40 |
| 31.9 | 2.81 | 2.95 |
| 32.9 | 2.72 | 1.27 |
| 34.4 | 2.61 | 5.98 |
| 35.1 | 2.56 | 2.07 |
| 36.2 | 2.48 | 3.16 |
| 37.2 | 2.42 | 2.37 |
| 37.9 | 2.37 | 1.79 |

Figure 4:
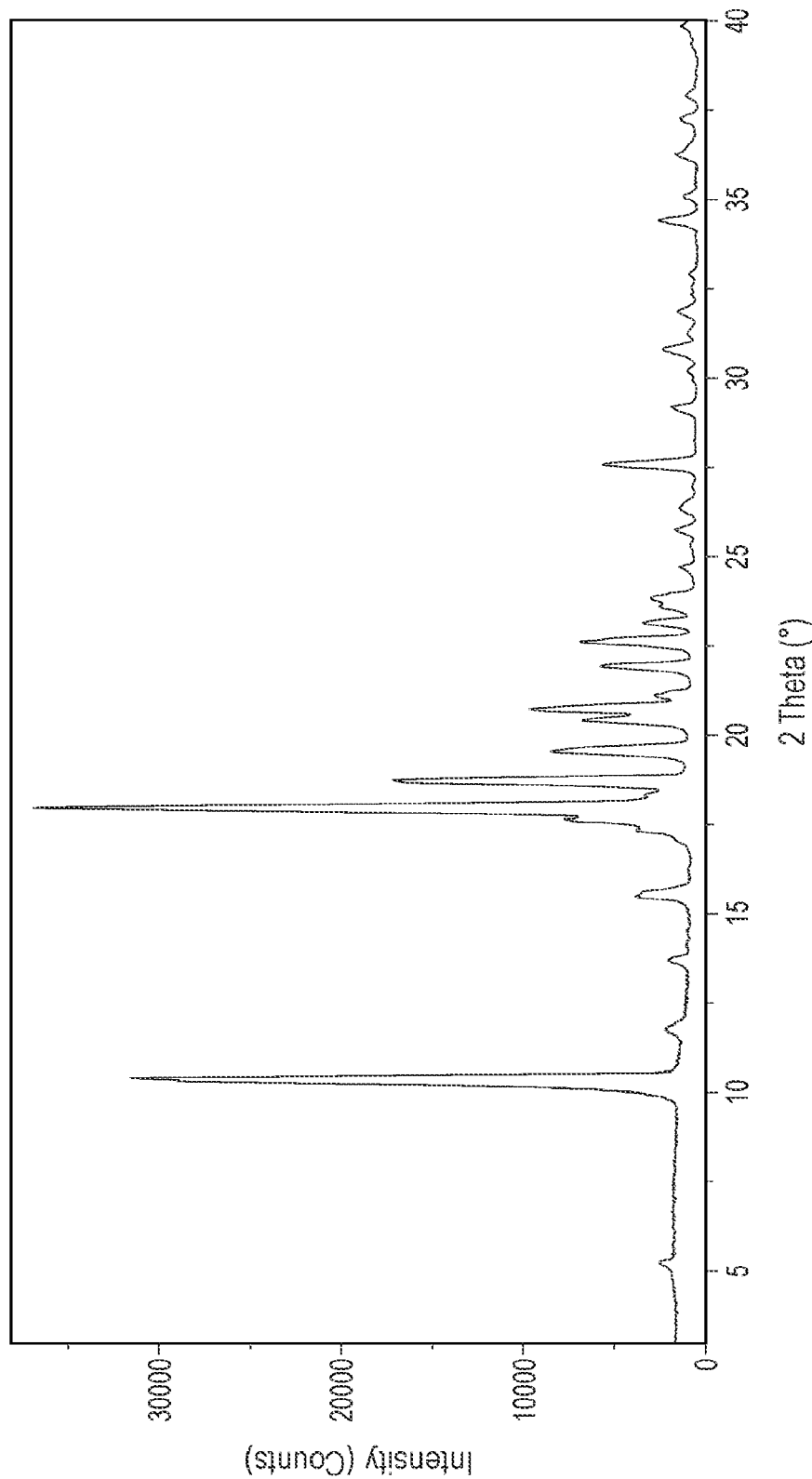
FIG. 4 is an X-ray powder diffraction pattern of the crystalline form of the compound of formula (V), as further described in Example 1.

In certain embodiments, the crystalline form of the compound of formula (V) is characterized by an X-ray powder diffraction pattern substantially the same as shown in FIG. 4.

In certain embodiments, the crystalline form of the compound of formula (V) exists in a monoclinic crystal system and has a $P2_1/c$ space group. In certain embodiments, the crystalline form of the compound of formula (V) is characterized by the crystallographic unit cell parameters as set forth in Table 2.

TABLE 2

Unit Cell Parameters of the Crystalline
Form of Compound of Formula (V)

| Unit cell dimensions | a = 17.9209(8) Å | α = 90° |
|---|---|---|
| | b = 9.8547(5) Å | β = 106.834(10)° |
| | c = 12.2775(6) | γ = 90° |
| Volume | 2075.35(17) Å³ | |
| Z | 4 | |
| Density (calculated) | 1.102 Mg/m³ | |

Figure 5:
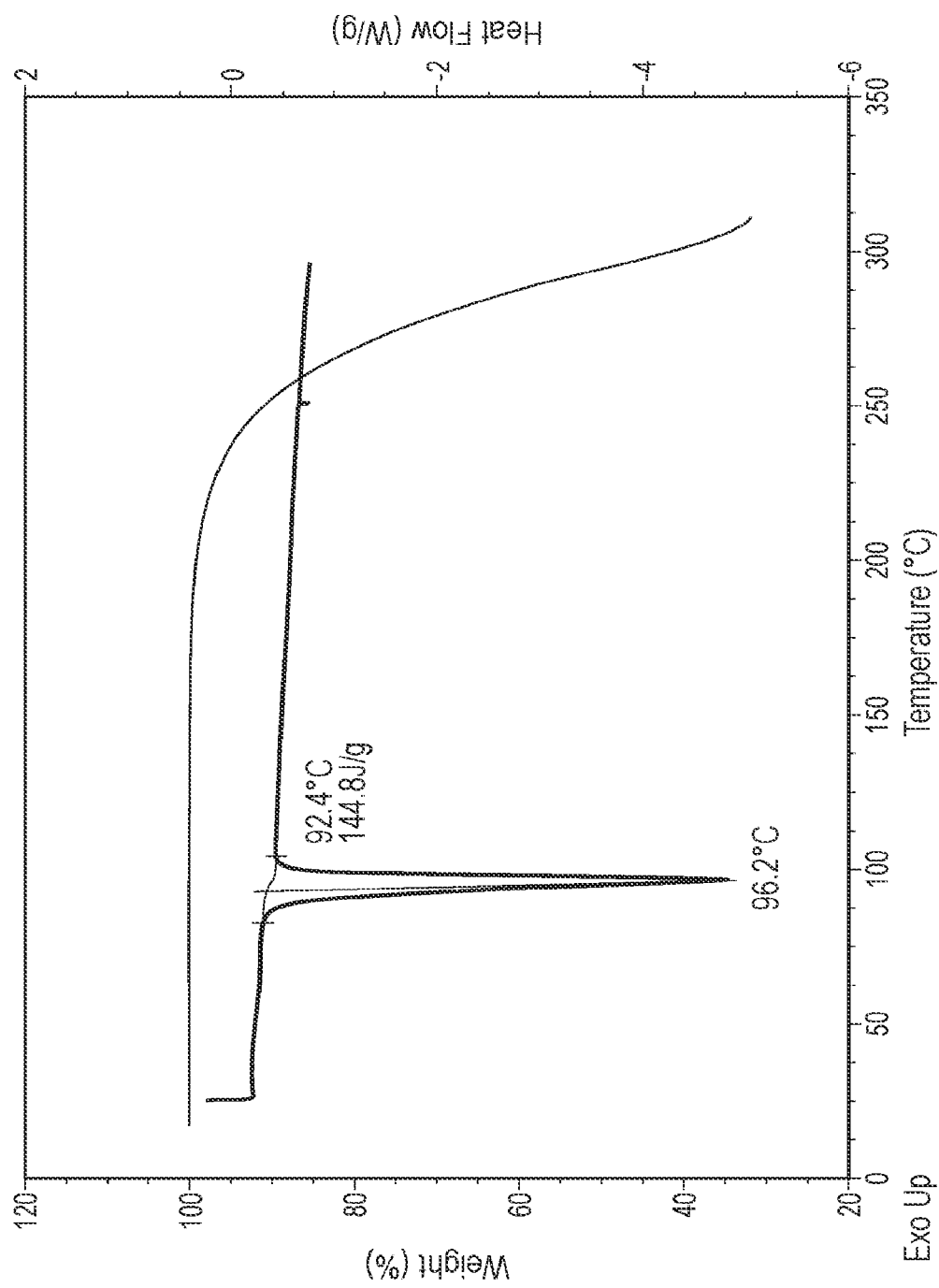
FIG. 5 is an overlay of differential scanning calorimetry (DSC) and thermogravimetric analysis (TGA) curves of the crystalline form of the compound of formula (V), as further described in Example 1.

The crystalline form of the compound of formula (V) may also be characterized according to the temperature of melting point onset. Accordingly, in certain embodiments, the crystalline form of the compound of formula (V) has a melting point onset as determined by differential scanning calorimetry in the range of from about 82° C. to about 94° C. In certain embodiments, the crystalline form of the compound of formula (V) has a melting point onset as determined by differential scanning calorimetry in the range of about 90° C. to about 94° C. In certain embodiments, the crystalline form of the compound of formula (V) has a melting point onset as determined by differential scanning calorimetry at about 92° C. In certain embodiments, the crystalline form of the compound of formula (V) has a differential scanning calorimetry curve substantially the same as shown in FIG. 5.

The crystalline form of the compound of formula (V) may also be characterized according to its mass gain/mass loss as a function of temperature. Accordingly, in certain embodiments, the crystalline form of the compound of formula (V) exhibits a reduction in mass, as determined by thermogravimetric analysis, of from about 0.1% to about 0.7% upon heating to about 200° C. In certain embodiments, the crystalline form of the compound of formula (V) exhibits a reduction in mass, as determined by thermogravimetric analysis, of less than or equal to about 0.7% upon heating to about 200° C. In certain embodiments, the crystalline form of the compound of formula (V) has a thermogravimetric analysis curve substantially the same as shown in FIG. 5.

Figure 6:
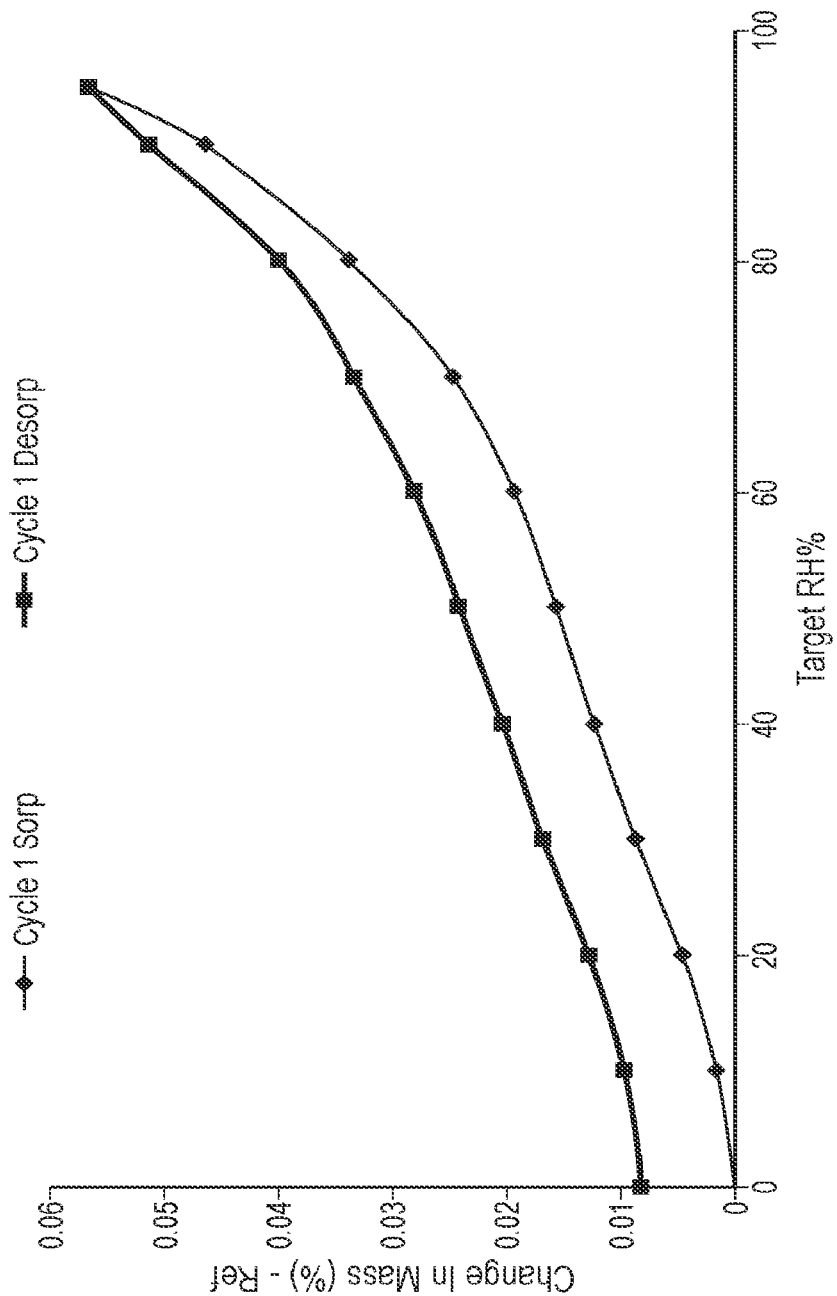
FIG. 6 is a water sorption isotherm of the crystalline form of the compound of formula (V).

The crystalline form of the compound of formula (V) may also be characterized according to its water sorption properties. Accordingly, in certain embodiments, the crystalline form of the compound of formula (V) exhibits a change in mass, as determined by dynamic vapor sorption, of from about 0.01% to about 0.05% at a relative humidity of 80% and a temperature of 25° C. In certain embodiments, the crystalline form of the compound of formula (V) exhibits a change in mass, as determined by dynamic vapor sorption, of about 0.03% at a relative humidity of 80% and a temperature of 25° C. In certain embodiments, the crystalline form of the compound of formula (V) has a water sorption isotherm, when measured at 25° C., substantially the same as shown in FIG. 6.

It should be understood that reference herein to bempedoic acid or a purified bempedoic acid includes the crystalline form of bempedoic acid, unless otherwise stated or understood from the context.

B. Crystalline Salt Forms of Bempedoic Acid

In addition, it has been discovered that various crystalline salt forms of bempedoic acid can be prepared. In particular, the following counter ions produced crystalline salt forms of bempedoic acid: ammonium, sodium, potassium, calcium (two crystal forms), lysine, diethylamine, ethylenediamine, piperazine, betaine, tromethamine, and isonicotinamide.

(i) Crystalline Betaine Salt Form of Bempedoic Acid

In certain embodiments, the crystalline salt form of bempedoic acid is a crystalline betaine salt of bempedoic acid. In certain embodiments, the crystalline betaine salt of bempedoic acid may be characterized by an X-ray powder diffraction pattern comprising peaks at the following diffraction angles (2θ): 6.2±0.2, 13.5±0.2, 17.5±0.2, 19.3±0.2, and 25.6±0.2. In certain embodiments, the crystalline betaine salt of bempedoic acid may be characterized by an X-ray powder diffraction pattern comprising peaks at the following diffraction angles (2θ): 6.2±0.2, 13.5±0.2, 16.1±0.2, 17.5±0.2, 19.3±0.2, 19.9±0.2, 25.6±0.2, and 27.2±0.2.

In certain embodiments, the crystalline betaine salt of bempedoic acid is characterized by the X-ray powder diffraction pattern expressed in terms of diffraction angle 2θ, and optionally inter-planar distances d, and relative intensity (expressed as a percentage with respect to the most intense peak) as set forth in Table 3.

TABLE 3

X-ray Powder Diffraction Data of the Crystalline
Betaine Salt of Bempedoic Acid

| Angle [2θ] | d-spacing [Å] | Relative Intensity [%] |
|---|---|---|
| 6.20 | 14.25 | 95.15 |
| 10.33 | 8.56 | 1.75 |

TABLE 3-continued

X-ray Powder Diffraction Data of the Crystalline Betaine Salt of Bempedoic Acid

| Angle [2θ] | d-spacing [Å] | Relative Intensity [%] |
| --- | --- | --- |
| 11.68 | 7.58 | 6.08 |
| 12.38 | 7.15 | 3.16 |
| 13.52 | 6.55 | 35.24 |
| 15.25 | 5.81 | 4.53 |
| 16.10 | 5.51 | 10.15 |
| 17.48 | 5.07 | 20.77 |
| 19.33 | 4.59 | 20.56 |
| 19.94 | 4.45 | 14.49 |
| 21.48 | 4.14 | 5.58 |
| 25.64 | 3.47 | 29.74 |
| 27.24 | 3.27 | 13.51 |
| 31.47 | 2.84 | 7.33 |
| 39.02 | 2.31 | 2.27 |

(ii) Crystalline Calcium Salt Forms of Bempedoic Acid

In certain embodiments, the crystalline salt form of bempedoic acid is a crystalline calcium salt of bempedoic acid. In certain embodiments, the crystalline calcium salt of bempedoic acid may be characterized by an X-ray powder diffraction pattern comprising peaks at the following diffraction angles (2θ): 4.9±0.2, 9.1±0.2, and 19.7±0.2. In certain embodiments, the crystalline calcium salt of bempedoic acid may be characterized by an X-ray powder diffraction pattern comprising peaks at the following diffraction angles (2θ): 4.9±0.2, 6.4±0.2, 9.1±0.2, 14.8±0.2, 19.7±0.2, and 37.1±0.2.

In certain embodiments, the crystalline calcium salt of bempedoic acid is characterized by the X-ray powder diffraction pattern expressed in terms of diffraction angle 2θ, and optionally inter-planar distances d, and relative intensity (expressed as a percentage with respect to the most intense peak) as set forth in Table 4.

TABLE 4

X-ray Powder Diffraction Data of the Crystalline Calcium Salt of Bempedoic Acid

| Angle [2θ] | d-spacing [Å] | Relative Intensity [%] |
| --- | --- | --- |
| 4.86 | 18.16 | 21.41 |
| 6.44 | 13.72 | 5.99 |
| 7.51 | 11.77 | 1.16 |
| 9.15 | 9.67 | 59.65 |
| 12.25 | 7.22 | 1.94 |
| 14.79 | 5.99 | 6.51 |
| 16.11 | 5.50 | 4.16 |
| 19.71 | 4.50 | 10.32 |
| 27.26 | 3.27 | 2.07 |
| 32.66 | 2.74 | 1.12 |
| 37.10 | 2.42 | 5.22 |
| 38.55 | 2.34 | 1.40 |

In certain embodiments, the crystalline calcium salt of bempedoic acid may be characterized by an X-ray powder diffraction pattern comprising peaks at the following diffraction angles (2θ): 6.0±0.2, 6.8±0.2, 8.5±0.2, and 9.8±0.2. In certain embodiments, the crystalline calcium salt of bempedoic acid may be characterized by an X-ray powder diffraction pattern comprising peaks at the following diffraction angles (2θ): 6.0±0.2, 6.8±0.2, 8.5±0.2, 9.8±0.2, 17.1±0.2, and 19.0±0.2.

In certain embodiments, the crystalline calcium salt of bempedoic acid is characterized by the X-ray powder diffraction pattern expressed in terms of diffraction angle 2θ, and optionally inter-planar distances d, and relative intensity (expressed as a percentage with respect to the most intense peak) as set forth in Table 5.

TABLE 5

X-ray Powder Diffraction Data of the Crystalline Calcium Salt of Bempedoic Acid

| Angle [2θ] | d-spacing [Å] | Relative Intensity [%] |
| --- | --- | --- |
| 6.03 | 14.65 | 49.46 |
| 6.79 | 13.01 | 28.89 |
| 8.53 | 10.37 | 100.00 |
| 9.80 | 9.02 | 77.92 |
| 12.05 | 7.35 | 2.31 |
| 14.09 | 6.29 | 4.03 |
| 17.10 | 5.18 | 13.68 |
| 19.03 | 4.66 | 5.37 |
| 33.15 | 2.70 | 0.90 |
| 35.89 | 2.50 | 1.92 |

(iii) Crystalline Diethylamine Salt Form of Bempedoic Acid

In certain embodiments, the crystalline salt form of bempedoic acid is a crystalline diethylamine salt of bempedoic acid. In certain embodiments, the crystalline diethylamine salt of bempedoic acid may be characterized by an X-ray powder diffraction pattern comprising peaks at the following diffraction angles (2θ): 9.6±0.2, 14.1±0.2, and 19.8±0.2. In certain embodiments, the crystalline diethylamine salt of bempedoic acid may be characterized by an X-ray powder diffraction pattern comprising peaks at the following diffraction angles (2θ): 9.6±0.2, 14.1±0.2, 17.8±0.2, 19.8±0.2, 22.6±0.2, and 38.7±0.2.

In certain embodiments, the crystalline diethylamine salt of bempedoic acid is characterized by the X-ray powder diffraction pattern expressed in terms of diffraction angle 2θ, and optionally inter-planar distances d, and relative intensity (expressed as a percentage with respect to the most intense peak) as set forth in Table 6.

TABLE 6

X-ray Powder Diffraction Data of the Crystalline Diethylamine Salt of Bempedoic Acid

| Angle [2θ] | d-spacing [Å] | Relative Intensity [%] |
| --- | --- | --- |
| 9.55 | 9.26 | 29.82 |
| 14.08 | 6.29 | 69.49 |
| 17.79 | 4.99 | 11.34 |
| 19.77 | 4.49 | 37.13 |
| 22.60 | 3.93 | 3.08 |
| 38.70 | 2.33 | 6.24 |

(iv) Crystalline Ethylenediamine Salt Form of Bempedoic Acid

In certain embodiments, the crystalline salt form of bempedoic acid is a crystalline ethylenediamine salt of bempedoic acid. In certain embodiments, the crystalline ethylenediamine salt of bempedoic acid may be characterized by an X-ray powder diffraction pattern comprising peaks at the following diffraction angles (2θ): 6.8±0.2, 10.8±0.2, 16.2±0.2, 18.3±0.2, and 18.8±0.2. In certain embodiments, the crystalline ethylenediamine salt of bempedoic acid may be characterized by an X-ray powder diffraction pattern comprising peaks at the following diffraction angles (2θ): 6.8±0.2, 7.7±0.2, 10.8±0.2, 13.9±0.2, 15.2±0.2, 16.2±0.2, 18.3±0.2, 18.8±0.2, 21.4±0.2, and 22.3±0.2.

In certain embodiments, the crystalline ethylenediamine salt of bempedoic acid is characterized by the X-ray powder diffraction pattern expressed in terms of diffraction angle 2θ, and optionally inter-planar distances d, and relative intensity (expressed as a percentage with respect to the most intense peak) as set forth in Table 7.

TABLE 7

X-ray Powder Diffraction Data of the Crystalline Ethylenediamine Salt of Bempedoic Acid

| Angle [2θ] | d-spacing [Å] | Relative Intensity [%] |
|---|---|---|
| 6.76 | 13.07 | 66.63 |
| 7.73 | 11.44 | 52.39 |
| 10.83 | 8.17 | 85.3 |
| 13.53 | 6.54 | 19.73 |
| 13.92 | 6.36 | 24.35 |
| 15.23 | 5.82 | 29.21 |
| 16.23 | 5.46 | 100.00 |
| 16.71 | 5.31 | 10.30 |
| 17.39 | 5.10 | 10.74 |
| 18.28 | 4.85 | 71.04 |
| 18.84 | 4.71 | 53.54 |
| 19.74 | 4.50 | 11.79 |
| 20.96 | 4.24 | 12.84 |
| 21.37 | 4.16 | 24.85 |
| 21.65 | 4.10 | 22.22 |
| 22.25 | 4.00 | 28.05 |
| 22.85 | 3.89 | 21.63 |
| 24.86 | 3.58 | 17.81 |
| 26.03 | 3.42 | 3.96 |
| 27.02 | 3.30 | 7.08 |
| 28.10 | 3.18 | 10.24 |
| 28.33 | 3.15 | 12.26 |
| 31.17 | 2.87 | 9.27 |
| 32.07 | 2.79 | 8.88 |
| 33.13 | 2.70 | 6.27 |
| 34.60 | 2.59 | 3.21 |
| 37.45 | 2.40 | 3.41 |

(v) Crystalline Isonicotinamide Salt Form of Bempedoic Acid

In certain embodiments, the crystalline salt form of bempedoic acid is a crystalline isonicotinamide salt of bempedoic acid. In certain embodiments, the crystalline isonicotinamide salt of bempedoic acid may be characterized by an X-ray powder diffraction pattern comprising peaks at the following diffraction angles (2θ): 4.4±0.2, 18.8±0.2, 20.1±0.2, and 24.5±0.2. In certain embodiments, the crystalline isonicotinamide salt of bempedoic acid may be characterized by an X-ray powder diffraction pattern comprising peaks at the following diffraction angles (2θ): 4.4±0.2, 14.5±0.2, 18.8±0.2, 20.1±0.2, 24.5±0.2, 26.2±0.2, and 29.5±0.2.

In certain embodiments, the crystalline isonicotinamide salt of bempedoic acid is characterized by the X-ray powder diffraction pattern expressed in terms of diffraction angle 2θ, and optionally inter-planar distances d, and relative intensity (expressed as a percentage with respect to the most intense peak) as set forth in Table 8.

TABLE 8

X-ray Powder Diffraction Data of the Crystalline Isonicotinamide Salt of Bempedoic Acid

| Angle [2θ] | d-spacing [Å] | Relative Intensity [%] |
|---|---|---|
| 4.36 | 20.26 | 31.75 |
| 8.89 | 9.95 | 0.44 |
| 11.49 | 7.70 | 1.86 |
| 13.05 | 6.78 | 1.75 |
| 14.47 | 6.12 | 4.77 |
| 18.36 | 4.83 | 3.21 |

TABLE 8-continued

X-ray Powder Diffraction Data of the Crystalline Isonicotinamide Salt of Bempedoic Acid

| Angle [2θ] | d-spacing [Å] | Relative Intensity [%] |
|---|---|---|
| 18.84 | 4.71 | 15.30 |
| 20.09 | 4.42 | 13.54 |
| 24.51 | 3.63 | 8.22 |
| 25.90 | 3.44 | 2.54 |
| 26.24 | 3.40 | 4.32 |
| 26.76 | 3.33 | 2.22 |
| 27.69 | 3.22 | 1.44 |
| 28.69 | 3.11 | 1.38 |
| 29.49 | 3.03 | 3.67 |
| 30.08 | 2.97 | 1.49 |
| 30.77 | 2.91 | 1.16 |
| 32.56 | 2.75 | 1.14 |
| 34.83 | 2.58 | 1.16 |
| 36.79 | 2.44 | 0.69 |

(vi) Crystalline Potassium Salt Form of Bempedoic Acid

In certain embodiments, the crystalline salt form of bempedoic acid is a crystalline potassium salt of bempedoic acid. In certain embodiments, the crystalline potassium salt of bempedoic acid may be characterized by an X-ray powder diffraction pattern comprising peaks at the following diffraction angles (2θ): 5.7±0.2, 7.3±0.2, 9.6±0.2, and 22.1±0.2. In certain embodiments, the crystalline potassium salt of bempedoic acid may be characterized by an X-ray powder diffraction pattern comprising peaks at the following diffraction angles (2θ): 5.7±0.2, 7.3±0.2, 9.6±0.2, 16.0±0.2, 22.1±0.2, and 23.0±0.2.

In certain embodiments, the crystalline potassium salt of bempedoic acid is characterized by the X-ray powder diffraction pattern expressed in terms of diffraction angle 2θ, and optionally inter-planar distances d, and relative intensity (expressed as a percentage with respect to the most intense peak) as set forth in Table 9.

TABLE 9

X-ray Powder Diffraction Data of the Crystalline Potassium Salt of Bempedoic Acid

| Angle [2θ] | d-spacing [Å] | Relative Intensity [%] |
|---|---|---|
| 5.71 | 15.48 | 95.20 |
| 7.33 | 12.06 | 100.00 |
| 9.58 | 9.23 | 17.10 |
| 15.99 | 5.54 | 9.16 |
| 22.10 | 4.02 | 18.51 |
| 22.97 | 3.87 | 3.21 |
| 24.83 | 3.59 | 2.48 |
| 29.94 | 2.98 | 0.86 |
| 37.72 | 2.39 | 1.40 |

(vii) Crystalline Lysine Salt Form of Bempedoic Acid

In certain embodiments, the crystalline salt form of bempedoic acid is a crystalline lysine salt of bempedoic acid. In certain embodiments, the crystalline lysine salt of bempedoic acid may be characterized by an X-ray powder diffraction pattern comprising peaks at the following diffraction angles (2θ): 4.2±0.2, 10.2±0.2, 19.1±0.2, 19.7±0.2, and 21.9±0.2. In certain embodiments, the crystalline lysine salt of bempedoic acid may be characterized by an X-ray powder diffraction pattern comprising peaks at the following diffraction angles (2θ): 4.2±0.2, 10.2±0.2, 13.5±0.2, 14.2±0.2, 16.0±0.2, 19.1±0.2, 19.7±0.2, and 21.9±0.2.

In certain embodiments, the crystalline lysine salt of bempedoic acid is characterized by the X-ray powder diffraction pattern expressed in terms of diffraction angle 2θ, and optionally inter-planar distances d, and relative intensity (expressed as a percentage with respect to the most intense peak) as set forth in Table 10.

TABLE 10

X-ray Powder Diffraction Data of the Crystalline Lysine Salt of Bempedoic Acid

| Angle [2θ] | d-spacing [Å] | Relative Intensity [%] |
|---|---|---|
| 4.22 | 20.95 | 79.22 |
| 10.23 | 8.65 | 24.52 |
| 13.53 | 6.55 | 18.67 |
| 14.22 | 6.23 | 20.50 |
| 15.96 | 5.55 | 16.26 |
| 19.12 | 4.64 | 100.00 |
| 19.68 | 4.51 | 30.60 |
| 21.91 | 4.06 | 36.00 |
| 23.09 | 3.85 | 11.64 |
| 25.45 | 3.50 | 13.58 |
| 33.18 | 2.70 | 4.36 |

(viii) Crystalline Sodium Salt Form of Bempedoic Acid

In certain embodiments, the crystalline salt form of bempedoic acid is a crystalline sodium salt of bempedoic acid. In certain embodiments, the crystalline sodium salt of bempedoic acid may be characterized by an X-ray powder diffraction pattern comprising peaks at the following diffraction angles (2θ): 6.1±0.2, 14.2±0.2, 18.3±0.2, and 24.5±0.2. In certain embodiments, the crystalline sodium salt of bempedoic acid may be characterized by an X-ray powder diffraction pattern comprising peaks at the following diffraction angles (2θ): 6.1±0.2, 13.4±0.2, 14.2±0.2, 16.6±0.2, 18.3±0.2, 19.1±0.2, and 24.5±0.2.

In certain embodiments, the crystalline sodium salt of bempedoic acid is characterized by the X-ray powder diffraction pattern expressed in terms of diffraction angle 2θ, and optionally inter-planar distances d, and relative intensity (expressed as a percentage with respect to the most intense peak) as set forth in Table 11.

TABLE 11

X-ray Powder Diffraction Data of the Crystalline Sodium Salt of Bempedoic Acid

| Angle [2θ] | d-spacing [Å] | Relative Intensity [%] |
|---|---|---|
| 6.10 | 14.48 | 100.00 |
| 8.16 | 10.83 | 1.15 |
| 10.89 | 8.13 | 2.68 |
| 12.19 | 7.28 | 3.98 |
| 13.36 | 6.63 | 6.65 |
| 14.22 | 6.23 | 11.60 |
| 16.63 | 5.33 | 8.50 |
| 16.86 | 5.26 | 1.01 |
| 18.32 | 4.84 | 24.10 |
| 19.12 | 4.64 | 9.38 |
| 21.36 | 4.16 | 1.36 |
| 21.83 | 4.07 | 1.51 |
| 22.07 | 4.03 | 2.91 |
| 22.42 | 3.97 | 1.34 |
| 22.67 | 3.92 | 1.91 |
| 24.08 | 3.70 | 3.19 |
| 24.50 | 3.63 | 11.00 |
| 25.11 | 3.55 | 3.04 |
| 28.92 | 3.09 | 0.79 |
| 29.79 | 3.00 | 1.62 |
| 30.77 | 2.91 | 1.87 |
| 32.32 | 2.77 | 0.59 |
| 33.02 | 2.71 | 1.13 |
| 34.12 | 2.63 | 0.32 |
| 37.11 | 2.42 | 0.34 |

TABLE 11-continued

X-ray Powder Diffraction Data of the Crystalline Sodium Salt of Bempedoic Acid

| Angle [2θ] | d-spacing [Å] | Relative Intensity [%] |
|---|---|---|
| 37.89 | 2.37 | 0.41 |
| 38.77 | 2.32 | 0.40 |

(ix) Crystalline Ammonium Salt Form of Bempedoic Acid

In certain embodiments, the crystalline salt form of bempedoic acid is a crystalline ammonium salt of bempedoic acid. In certain embodiments, the crystalline ammonium salt of bempedoic acid may be characterized by an X-ray powder diffraction pattern comprising peaks at the following diffraction angles (2θ): 6.9±0.2, 7.1±0.2, 14.3±0.2, 16.0±0.2, and 21.4±0.2. In certain embodiments, the crystalline ammonium salt of bempedoic acid may be characterized by an X-ray powder diffraction pattern comprising peaks at the following diffraction angles (2θ): 6.9±0.2, 7.1±0.2, 9.3±0.2, 14.3±0.2, 16.0±0.2, 18.2±0.2, 19.2±0.2, 21.4±0.2, and 22.3±0.2.

In certain embodiments, the crystalline ammonium salt of bempedoic acid is characterized by the X-ray powder diffraction pattern expressed in terms of diffraction angle 2θ, and optionally inter-planar distances d, and relative intensity (expressed as a percentage with respect to the most intense peak) as set forth in Table 12.

TABLE 12

X-ray Powder Diffraction Data of the Crystalline Ammonium Salt of Bempedoic Acid

| Angle [2θ] | d-spacing [Å] | Relative Intensity [%] |
|---|---|---|
| 6.92 | 12.78 | 32.02 |
| 7.12 | 12.41 | 52.37 |
| 9.27 | 9.54 | 25.96 |
| 12.37 | 7.15 | 11.85 |
| 14.26 | 6.21 | 45.64 |
| 15.96 | 5.55 | 47.86 |
| 16.72 | 5.30 | 22.51 |
| 17.08 | 5.19 | 24.62 |
| 18.16 | 4.89 | 33.61 |
| 19.17 | 4.63 | 31.17 |
| 21.43 | 4.15 | 44.99 |
| 22.26 | 3.99 | 31.44 |
| 24.05 | 3.70 | 16.43 |
| 24.56 | 3.62 | 10.08 |
| 27.32 | 3.26 | 12.47 |
| 27.79 | 3.21 | 9.98 |
| 27.98 | 3.19 | 10.01 |
| 29.36 | 3.04 | 3.14 |
| 29.83 | 3.00 | 3.47 |
| 30.30 | 2.95 | 4.46 |
| 30.94 | 2.89 | 4.92 |
| 35.56 | 2.52 | 14.29 |
| 36.67 | 2.45 | 5.59 |
| 37.62 | 2.39 | 2.72 |
| 38.66 | 2.33 | 2.81 |

(x) Crystalline Piperazine Salt Form of Bempedoic Acid

In certain embodiments, the crystalline salt form of bempedoic acid is a crystalline piperazine salt of bempedoic acid. In certain embodiments, the crystalline piperazine salt of bempedoic acid may be characterized by an X-ray powder diffraction pattern comprising peaks at the following diffraction angles (2θ): 6.7±0.2, 8.7±0.2, 10.7±0.2, 15.7±0.2, and 16.0±0.2. In certain embodiments, the crystalline piperazine salt of bempedoic acid may be characterized by an X-ray powder diffraction pattern comprising peaks at the following diffraction angles (2θ): 6.7±0.2, 8.7±0.2, 10.7±0.2, 15.7±0.2, 16.0±0.2, 19.4±0.2, 20.1±0.2, and 21.4±0.2.

In certain embodiments, the crystalline piperazine salt of bempedoic acid is characterized by the X-ray powder diffraction pattern expressed in terms of diffraction angle 2θ, and optionally inter-planar distances d, and relative intensity (expressed as a percentage with respect to the most intense peak) as set forth in Table 13.

TABLE 13

X-ray Powder Diffraction Data of the Crystalline Piperazine Salt of Bempedoic Acid

| Angle [2θ] | d-spacing [Å] | Relative Intensity [%] |
|---|---|---|
| 6.66 | 13.27 | 74.02 |
| 8.69 | 10.18 | 40.75 |
| 10.70 | 8.27 | 33.84 |
| 13.35 | 6.63 | 11.79 |
| 15.68 | 5.65 | 48.82 |
| 15.99 | 5.54 | 100.00 |
| 19.38 | 4.58 | 23.99 |
| 20.10 | 4.42 | 18.23 |
| 21.35 | 4.16 | 18.56 |
| 27.52 | 3.24 | 3.45 |
| 28.61 | 3.12 | 6.01 |
| 34.01 | 2.64 | 5.19 |

(xi) Crystalline Tromethamine Salt Form of Bempedoic Acid

In certain embodiments, the crystalline salt form of bempedoic acid is a crystalline tromethamine salt of bempedoic acid. In certain embodiments, the crystalline tromethamine salt of bempedoic acid may be characterized by an X-ray powder diffraction pattern comprising peaks at the following diffraction angles (2θ): 6.6±0.2, 18.2±0.2, 18.6±0.2, and 19.8±0.2. In certain embodiments, the crystalline tromethamine salt of bempedoic acid may be characterized by an X-ray powder diffraction pattern comprising peaks at the following diffraction angles (2θ): 6.6±0.2, 13.6±0.2, 18.2±0.2, 18.6±0.2, 19.8±0.2, and 26.5±0.2.

In certain embodiments, the crystalline tromethamine salt of bempedoic acid is characterized by the X-ray powder diffraction pattern expressed in terms of diffraction angle 2θ, and optionally inter-planar distances d, and relative intensity (expressed as a percentage with respect to the most intense peak) as set forth in Table 14.

TABLE 14

X-ray Powder Diffraction Data of the Crystalline Tromethamine Salt Bempedoic Acid

| Angle [2θ] | d-spacing [Å] | Relative Intensity [%] |
|---|---|---|
| 6.60 | 13.39 | 100.00 |
| 9.10 | 9.72 | 1.10 |
| 13.57 | 6.53 | 1.90 |
| 13.94 | 6.35 | 1.47 |
| 17.08 | 5.19 | 1.34 |
| 18.19 | 4.88 | 2.33 |
| 18.62 | 4.77 | 2.76 |
| 19.31 | 4.60 | 1.40 |
| 19.79 | 4.49 | 10.06 |
| 21.68 | 4.10 | 0.33 |
| 26.55 | 3.36 | 2.17 |
| 28.21 | 3.16 | 0.61 |
| 30.67 | 2.92 | 0.27 |
| 33.69 | 2.66 | 0.24 |

C. Co-Crystal Forms of Bempedoic Acid

Moreover, it was discovered that certain co-crystal forms of bempedoic acid could be prepared. In particular, the following co-formers produced co-crystals with bempedoic acid: palmitic acid and aspartame (two crystal forms).

(i) Co-Crystal of Bempedoic Acid and Aspartame

In certain embodiments, the co-crystal form of bempedoic acid is a co-crystal form of bempedoic acid and aspartame. In certain embodiments, the co-crystal form of bempedoic acid and aspartame may be characterized by an X-ray powder diffraction pattern comprising peaks at the following diffraction angles (2θ): 7.6±0.2, 8.6±0.2, 17.3±0.2, 18.4±0.2, and 25.1±0.2. In certain embodiments, the co-crystal form of bempedoic acid and aspartame may be characterized by an X-ray powder diffraction pattern comprising peaks at the following diffraction angles (2θ): 7.6±0.2, 8.6±0.2, 14.4±0.2, 17.3±0.2, 18.4±0.2, 25.1±0.2, 25.2±0.2, 26.1.

In certain embodiments, the co-crystal form of bempedoic acid and aspartame is characterized by the X-ray powder diffraction pattern expressed in terms of diffraction angle 2θ, and optionally inter-planar distances d, and relative intensity (expressed as a percentage with respect to the most intense peak) as set forth in Table 15.

TABLE 15

X-ray Powder Diffraction Data of the Co-crystal Form of Bempedoic Acid and Aspartame

| Angle [2θ] | d-spacing [Å] | Relative Intensity [%] |
|---|---|---|
| 7.6 | 11.60 | 82.14 |
| 8.6 | 10.23 | 22.88 |
| 13.3 | 6.67 | 3.69 |
| 14.4 | 6.14 | 19.99 |
| 15.3 | 5.80 | 7.52 |
| 17.3 | 5.12 | 32.09 |
| 18.4 | 4.82 | 100.00 |
| 20.9 | 4.26 | 4.07 |
| 23.0 | 3.87 | 6.98 |
| 25.1 | 3.54 | 23.14 |
| 25.2 | 3.53 | 17.65 |
| 26.1 | 3.42 | 19.40 |
| 29.0 | 3.08 | 1.60 |
| 31.2 | 2.87 | 8.23 |
| 32.4 | 2.76 | 2.29 |
| 35.6 | 2.52 | 2.32 |
| 36.6 | 2.45 | 3.48 |

In certain embodiments, the co-crystal form of bempedoic acid and aspartame may be characterized by an X-ray powder diffraction pattern comprising peaks at the following diffraction angles (2θ): 4.4±0.2, 6.8±0.2, 10.6±0.2, 13.2±0.2, and 18.4±0.2. In certain embodiments, the co-crystal form of bempedoic acid and aspartame may be characterized by an X-ray powder diffraction pattern comprising peaks at the following diffraction angles (2θ): 4.4±0.2, 5.6±0.2, 6.8±0.2, 10.6±0.2, 12.3±0.2, 13.2±0.2, 13.6±0.2, 16.2±0.2, 17.6±0.2, and 18.4±0.2.

In certain embodiments, the co-crystal form of bempedoic acid and aspartame is characterized by the X-ray powder diffraction pattern expressed in terms of diffraction angle 2θ, and optionally inter-planar distances d, and relative intensity (expressed as a percentage with respect to the most intense peak) as set forth in Table 16.

TABLE 16

X-ray Powder Diffraction Data of the Co-crystal Form of Bempedoic Acid and Aspartame

| Angle [2θ] | d-spacing [Å] | Relative Intensity [%] |
|---|---|---|
| 4.4 | 20.07 | 100.00 |
| 5.6 | 15.71 | 18.95 |
| 6.8 | 13.01 | 23.46 |

TABLE 16-continued

X-ray Powder Diffraction Data of the
Co-crystal Form of Bempedoic Acid and Aspartame

| Angle [2θ] | d-spacing [Å] | Relative Intensity [%] |
|---|---|---|
| 8.6 | 10.27 | 3.51 |
| 10.6 | 8.38 | 26.31 |
| 12.3 | 7.22 | 14.92 |
| 13.2 | 6.70 | 23.91 |
| 13.6 | 6.53 | 18.83 |
| 16.2 | 5.47 | 15.84 |
| 16.8 | 5.28 | 13.01 |
| 17.6 | 5.03 | 19.15 |
| 18.4 | 4.83 | 25.66 |
| 19.0 | 4.68 | 12.76 |
| 22.9 | 3.88 | 8.04 |
| 25.1 | 3.54 | 5.95 |
| 29.2 | 3.05 | 6.26 |
| 31.0 | 2.89 | 5.42 |
| 31.5 | 2.83 | 5.95 |
| 32.9 | 2.72 | 4.77 |

(ii) Co-Crystal of Bempedoic Acid and Palmitic Acid

In certain embodiments, the co-crystal form of bempedoic acid is a co-crystal form of bempedoic acid and palmitic acid. In certain embodiments, the co-crystal form of bempedoic acid and palmitic acid may be characterized by an X-ray powder diffraction pattern comprising peaks at the following diffraction angles (2θ): 4.3±0.2, 6.3±0.2, 8.5±0.2, and 17.0±0.2. In certain embodiments, the co-crystal form of bempedoic acid and palmitic acid may be characterized by an X-ray powder diffraction pattern comprising peaks at the following diffraction angles (2θ): 4.3±0.2, 6.3±0.2, 8.5±0.2, 10.5±0.2, 17.0±0.2, and 25.5±0.2.

In certain embodiments, the co-crystal form of bempedoic acid and palmitic acid is characterized by the X-ray powder diffraction pattern expressed in terms of diffraction angle 2θ, and optionally inter-planar distances d, and relative intensity (expressed as a percentage with respect to the most intense peak) as set forth in Table 17.

TABLE 17

X-ray Powder Diffraction Data of the Co-crystal
Form of Bempedoic Acid and Palmitic Acid

| Angle [2θ] | d-spacing [Å] | Relative Intensity [%] |
|---|---|---|
| 4.3 | 20.74 | 100.00 |
| 6.3 | 14.00 | 27.40 |
| 8.5 | 10.42 | 11.40 |
| 10.5 | 8.41 | 6.34 |
| 17.0 | 5.22 | 9.46 |
| 21.2 | 4.19 | 4.72 |
| 24.6 | 3.61 | 4.33 |
| 25.5 | 3.49 | 4.99 |
| 29.9 | 2.99 | 2.02 |
| 34.4 | 2.61 | 2.54 |

III. Methods of Preparing Bempedoic Acid
Including Purified Bempedoic Acid

As described herein, in one aspect, the invention provides methods of preparing 8-hydroxy-2,2,14,14-tetramethylpentadecanedioic acid, which is a compound of formula (V):

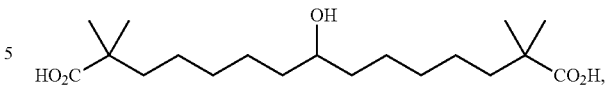

which methods also include making a pharmaceutically acceptable salt thereof.

It should be understood that methods of the invention include preparing bempedoic acid. In certain embodiments, the methods of preparing bempedoic acid result in purified bempedoic acid, which also can be described herein with respect to a pharmaceutical material, i.e., a pharmaceutical material comprising an amount of bempedoic acid or an amount of a compound of formula (V), or a pharmaceutically acceptable salt thereof. These terms and phrases can be used interchangeably herein, unless otherwise stated or understood from the context.

Accordingly, in various embodiments, methods are provided for preparing a pharmaceutical material comprising a compound of formula (V):

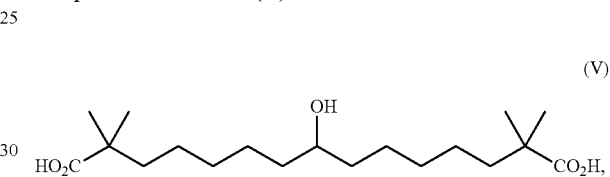

or a pharmaceutically acceptable salt thereof.

In various embodiments, the methods generally include:

(a) contacting ethyl isobutyrate with a substituted 5-chloropentane in the presence of a first base to form a compound of formula (I):

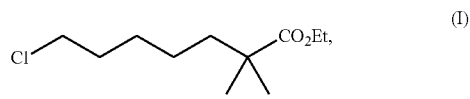

wherein the substituted 5-chloropentane is selected from the group consisting of 1-bromo-5-chloropentane and 1-iodo-5-chloropentane;

(b) contacting the compound of formula (I) with a salt of formula [M]$^+$[X]$^-$ to form a compound of formula (II):

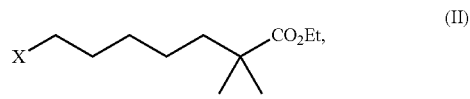

wherein [M]$^+$ is selected from the group consisting of Li$^+$, Na$^+$ and K$^+$, wherein [X]$^-$ is selected from the group consisting of Br$^-$ and I$^-$;

(c) contacting the compound of formula (II) with toluenesulfonylmethyl isocyanide in the presence of a second base to form a first intermediate, and contacting the first intermediate with an acid to form a compound of formula (IV):

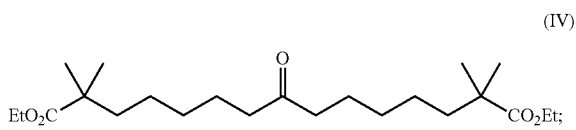 [SMILES: CCOC(=O)C(C)(C)CCCCCC(=O)CCCCCC(C)(C)C(=O)OCC]

and (d) contacting the compound of formula (IV) with a reducing agent to form a second intermediate, and contacting the second intermediate with a hydrolyzing base to form a compound of formula (V).

In certain embodiments of the invention, the method further comprises:

(e) purifying the compound of formula (V) to provide a pharmaceutical material comprising a purified amount of the compound of formula (V).

Synthesis of a Compound of Formula (I)—Step (a)

In various embodiments, synthesis of the compound of formula (I):

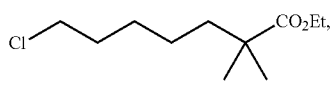

generally comprises contacting ethyl isobutyrate with a substituted 5-chloropentane in the presence of a first base.

In certain embodiments, in step (a), contacting ethyl isobutyrate with the substituted 5-chloropentane in the presence of a first base is conducted at a temperature in the range of from about −30° C. to about 10° C., from about −25° C. to about 10° C., from about −20° C. to about 10° C., from about −18° C. to about 10° C., from about −15° C. to about 10° C., from about −10° C. to about 10° C., from about −5° C. to about 10° C., from about 0° C. to about 10° C., from about 5° C. to about 10° C., from about −30° C. to about 5° C., from about −30° C. to about 0° C., from about −30° C. to about −5° C., from about −30° C. to about −10° C., from about −30° C. to about −15° C., from about −30° C. to about −18° C., from about −30° C. to about −20° C., from about −30° C. to about −25° C., from about −25° C. to about 5° C., from about −25° C. to about 0° C., from about −25° C. to about −5° C., from about −25° C. to about −10° C., from about −25° C. to about −15° C., from about −25° C. to about −18° C., from about −25° C. to about −20° C., from about −20° C. to about 5° C., from about −20° C. to about 0° C., from about −20° C. to about −5° C., from about −20° C. to about −10° C., from about −20° C. to about −15° C., from about −20° C. to about −18° C., from about −18° C. to about 5° C., from about −18° C. to about 0° C., from about −18° C. to about −5° C., from about −18° C. to about −10° C., from about −18° C. to about −15° C., from about −15° C. to about 5° C., from about −15° C. to about 0° C., from about −15° C. to about −5° C., from about −15° C. to about −10° C., from about −10° C. to about 5° C., from about −10° C. to about 0° C., from about −10° C. to about −5° C., from about −5° C. to about 5° C., or from about −5° C. to about 0° C. In certain embodiments, in step (a), contacting ethyl isobutyrate with the substituted 5-chloropentane in the presence of a first base is conducted at a temperature in the range of from about −20° C. to about 0° C. In certain embodiments, in step (a), contacting ethyl isobutyrate with the substituted 5-chloropentane in the presence of a first base is conducted at a temperature in the range of from about −18° C. to about −5° C.

In certain embodiments, in step (a), less than about 0.5% by weight, about 0.6% by weight, about 0.7% by weight, about 0.8% by weight, about 0.9% by weight, about 1% by weight, about 1.1% by weight, about 1.2% by weight, about 1.3% by weight, about 1.4% by weight, or about 1.5% by weight of the substituted 5-chloropentane remains after forming the compound of formula (I). In some embodiments, in step (a), less than about 1% by weight of the substituted 5-chloropentane remains after forming the compound of formula (I).

In certain embodiments, in step (a), the molar ratio of ethyl isobutyrate to the substituted 5-chloropentane is about 1:1, about 1.01:1, about 1.02:1, about 1.03:1, about 1.04:1, about 1.05:1, about 1.06:1, about 1.07:1, about 1.08:1, about 1.09:1, about 1.1:1, about 1.11:1, about 1.12:1, about 1.13:1, about 1.14:1, about 1.15:1, about 1.16:1, about 1.17:1, about 1.18:1, about 1.19:1, about 1.2:1, or about 1.21:1, including the ranges between each of these ratios. In some embodiments, in step (a), the molar ratio of ethyl isobutyrate to the substituted 5-chloropentane is about 1.1:1. In some embodiments, the molar ratio of ethyl isobutyrate to the substituted 5-chloropentane is from about 1.1:1 to about 1.21:1.

In certain embodiments, in step (a), the substituted 5-chloropentane is contacted ethyl isobutyrate, which is present in an amount of about 1 molar equivalent, about 1.01 molar equivalents, about 1.02 molar equivalents, about 1.03 molar equivalents, about 1.04 molar equivalents, about 1.05 molar equivalents, about 1.06 molar equivalents, about 1.07 molar equivalents, about 1.08 molar equivalents, about 1.09 molar equivalents, about 1.1 molar equivalents, about 1.11 molar equivalents, about 1.12 molar equivalents, about 1.13 molar equivalents, about 1.14 molar equivalents, about 1.15 molar equivalents, about 1.16 molar equivalents, about 1.17 molar equivalents, about 1.18 molar equivalents, about 1.19 molar equivalents, about 1.2 molar equivalents, or about 1.21 molar equivalents. In some embodiments, in step (a), the substituted 5-chloropentane is contacted with about 1.1 molar equivalents of ethyl isobutyrate.

In certain embodiments, in step (a), contacting ethyl isobutyrate and the substituted 5-chloropentane occurs by adding ethyl isobutyrate and the substituted 5-chloropentane to a reactor. In some embodiments, in step (a), adding ethyl isobutyrate and the substituted 5-chloropentane to the reactor occurs at a temperature of less than about 10° C., less than about 5° C., less than about 0° C., less than about −5° C., less than about −10° C., less than about −15° C., less than about −20° C., less than about −25° C., or less than about −30° C. In some embodiments, in step (a), adding ethyl isobutyrate and the substituted 5-chloropentane to the reactor occurs at a temperature of about 10° C., about 5° C., about 0° C., about −5° C., about −7° C., about −10° C., about −12° C., about −14° C., about −16° C., about −18° C., about −20° C., about −22° C., about −24° C., about −26° C., about −28° C., or about −30° C. In some embodiments, in step (a), adding ethyl isobutyrate and the substituted 5-chloropentane to the reactor occurs at a temperature of about −5° C. In some embodiments, in step (a), adding ethyl isobutyrate and the substituted 5-chloropentane to the reactor occurs at a temperature of about −12° C. In some embodiments, in step (a), adding ethyl isobutyrate and the substituted 5-chloropentane to the reactor occurs at a temperature of about −18° C.

In certain embodiments, in step (a), the time of adding ethyl isobutyrate and the substituted 5-chloropentane to the reactor is about 5 mins, about 10 mins, about 15 mins, about 20 mins, about 30 mins, about 40 mins, about 50 mins, about 1 hour, about 2 hours, about 3 hours, about 4 hours, about 5 hours, about 6 hours, about 7 hours, about 8 hours, about 9 hours, about 10 hours, about 11 hours, or about 12 hours.

In certain embodiments, in step (a), the time of adding ethyl isobutyrate and the substituted 5-chloropentane to the reactor is from about 10 mins to about 60 mins, from about 20 mins to about 60 mins, from about 30 mins to about 60 mins, from about 40 mins to about 60 mins, from about 50 mins to about 60 mins, from about 10 mins to about 50 mins, from about 10 mins to about 40 mins, from about 10 mins to about 30 mins, from about 10 mins to about 20 mins, from about 20 mins to about 50 mins, from about 20 mins to about 40 mins, from about 20 mins to about 30 mins, from about 30 mins to about 50 mins, from about 30 mins to about 40 mins, or from about 40 mins to about 50 mins.

In certain embodiments, in step (a), the time of adding ethyl isobutyrate and the substituted 5-chloropentane to the reactor is from about 1 hour to about 12 hours, from about 2 hours to about 12 hours, from about 3 hours to about 12 hours, from about 4 hours to about 12 hours, from about 5 hours to about 12 hours, from about 6 hours to about 12 hours, from about 7 hours to about 12 hours, from about 8 hours to about 12 hours, from about 9 hours to about 12 hours, from about 10 hours to about 12 hours, from about 11 hours to about 12 hours, from about 1 hours to about 11 hours, from about 1 hours to about 10 hours, from about 1 hours to about 9 hours, from about 1 hours to about 8 hours, from about 1 hours to about 7 hours, from about 1 hours to about 6 hours, from about 1 hours to about 5 hours, from about 1 hours to about 4 hours, from about 1 hours to about 3 hours, from about 1 hours to about 2 hours, from about 2 hours to about 11 hours, from about 2 hours to about 10 hours, from about 2 hours to about 9 hours, from about 2 hours to about 8 hours, from about 2 hours to about 7 hours, from about 2 hours to about 6 hours, from about 2 hours to about 5 hours, from about 2 hours to about 4 hours, from about 2 hours to about 3 hours, from about 3 hours to about 11 hours, from about 3 hours to about 10 hours, from about 3 hours to about 9 hours, from about 3 hours to about 8 hours, from about 3 hours to about 7 hours, from about 3 hours to about 6 hours, from about 3 hours to about 5 hours, from about 3 hours to about 4 hours, from about 4 hours to about 11 hours, from about 4 hours to about 10 hours, from about 4 hours to about 9 hours, from about 4 hours to about 8 hours, from about 4 hours to about 7 hours, from about 4 hours to about 6 hours, from about 4 hours to about 5 hours, from about 5 hours to about 11 hours, from about 5 hours to about 10 hours, from about 5 hours to about 9 hours, from about 5 hours to about 8 hours, from about 5 hours to about 7 hours, from about 5 hours to about 6 hours, from about 6 hours to about 11 hours, from about 6 hours to about 10 hours, from about 6 hours to about 9 hours, from about 6 hours to about 8 hours, from about 6 hours to about 7 hours, from about 7 hours to about 11 hours, from about 7 hours to about 10 hours, from about 7 hours to about 9 hours, from about 7 hours to about 8 hours, from about 8 hours to about 11 hours, from about 8 hours to about 10 hours, from about 8 hours to about 9 hours, from about 9 hours to about 11 hours, from about 9 hours to about 10 hours, or from about 10 hours to about 11 hours.

In some embodiments, adding ethyl isobutyrate and the substituted 5-chloropentane to the reactor occurs simultaneously. In some embodiments, adding ethyl isobutyrate to the reactor occurs prior to adding the substituted 5-chloropentane to the reactor. In some embodiments, adding ethyl isobutyrate to the reactor occurs after adding the substituted 5-chloropentane to the reactor.

In certain embodiments, contacting ethyl isobutyrate with the substituted 5-chloropentane in the presence of a first base forms a reaction mixture. In certain embodiments, in step (a), at the end of the reaction, the methods include quenching the reaction mixture with an acid. In some embodiments, the acid is hydrochloric acid.

In certain embodiments, ethyl isobutyrate and the substituted 5-chloropentane are starting materials used in the production of the compound of formula (I). In certain embodiments, the purity of the substituted 5-chloropentane is ≥99%, ≥99.1%, ≥99.2%, ≥99.3%, ≥99.4%, ≥99.5%, ≥99.6%, ≥99.7%, ≥99.8%, or ≥99.9%, as measured by gas chromatography (GC). In some embodiments, the purity of the substituted 5-chloropentane is ≥99%, as measured by GC.

In certain embodiments, the purity of ethyl isobutyrate is ≥99%, ≥99.1%, ≥99.2%, ≥99.3%, ≥99.4%, ≥99.5%, ≥99.6%, ≥99.7%, ≥99.8%, or ≥99.9%, as measured by gas chromatography (GC). In some embodiments, the purity of ethyl isobutyrate is ≥99.5%, as measured by GC.

In certain embodiments, the concentration of ethanol present in ethyl isobutyrate is ≤0.05%, ≤0.06%, ≤0.07%, 0.08%, ≤0.09%, 0.1%, ≤0.11%, ≤0.12%, ≤0.13%, ≤0.14%, or ≤0.15%, as measured by GC. In some embodiments, the concentration of ethanol present in ethyl isobutyrate is 0.1%, as measured by GC.

In certain embodiments, the substituted 5-chloropentane is 1-iodo-5-chloropentane. In certain embodiments, the substituted 5-chloropentane is 1-bromo-5-chloropentane.

In certain embodiments, the purity of 1-iodo-5-chloropentane or 1-bromo-5-chloropentane is ≥99%, ≥99.1%, ≥99.2%, ≥99.3%, ≥99.4%, ≥99.5%, ≥99.6%, ≥99.7%, 99.8%, or ≥99.9%, as measured by gas chromatography (GC).

In certain embodiments, in step (a), the first base is selected from the group consisting of lithium diisopropylamide, lithium bis(trimethylsilyl)amide, sodium hydride, sodium amide, lithium amide, and lithium tetramethylpiperidide. In some embodiments, in step (a), the first base is lithium diisopropylamide.

In certain embodiments, the amount of unreacted substituted 5-chloropentane remaining upon completion of step (a) is ≤0.05%, ≤0.06%, ≤0.07%, ≤0.08%, ≤0.09%, ≤0.1%, ≤0.11%, ≤0.12%, ≤0.12%, ≤0.13%, ≤0.14%, ≤0.15%, ≤0.16%, ≤0.17%, ≤0.18%, ≤0.19%, or ≤0.2%, as measured by GC. In some embodiments, the amount of unreacted substituted 5-chloropentane remaining upon completion of step (a) is ≤0.21%, ≤0.22%, ≤0.23%, ≤0.24%, ≤0.25%, ≤0.25%, ≤0.26%, ≤0.27%, ≤0.28%, ≤0.29%, ≤0.3%, ≤0.31%, ≤0.32%, ≤0.33%, ≤0.34%, ≤0.35%, ≤0.36%, ≤0.37%, ≤0.38%, ≤0.39%, or ≤0.4%, as measured by GC.

Synthesis of Lithium Diisopropylamide (a First Base for Making the Compound of Formula (I))

In various embodiments, the synthesis of lithium diisopropylamide, which is a base used for making the compound of formula (I):

(I)

generally comprises contacting diisopropylamine with butyllithium.

In certain embodiments, the molar ratio of butyllithium to diisopropylamine is about 1:1.04, about 1:1.05, about 1:1.06, about 1:1.07, about 1:1.08, about 1:1.09, about 1:1.1, about 1:1.2, about 1:1.3, about 1:1.4, about 1:1.5, or about 1:1.6. In some embodiments, the molar ratio of butyllithium to diisopropylamine is about 1:1.07. In some embodiments, the molar ratio of butyllithium to diisopropylamine is about 1:1.5.

In certain embodiments, the molar ratio of butyllithium to diisopropylamine is from about 1:1.04 to about 1:1.1, from about 1:1.05 to about 1:1.1, from about 1:1.06 to about 1:1.1, from about 1:1.07 to about 1:1.1, from about 1:1.08 to about 1:1.1, from about 1:1.09 to about 1:1, from about 1:1.04 to about 1:1.09, from about 1:1.04 to about 1:1.08, from about 1:1.04 to about 1:1.07, from about 1:1.04 to about 1:1.06, from about 1:1.04 to about 1:1.05, from about 1:1.05 to about 1:1.09, from about 1:1.05 to about 1:1.08, from about 1:1.05 to about 1:1.07, from about 1:1.05 to about 1:1.06, from about 1:1.06 to about 1:1.09, from about 1:1.06 to about 1:1.08, from about 1:1.06 to about 1:1.07, from about 1:1.07 to about 1:1.09, from about 1:1.07 to about 1:1.08, or from about 1:1.08 to about 1:1.09. In some embodiments, the molar ratio of butyllithium to diisopropylamine is from about 1:1.06 to about 1:1.07.

In certain embodiments, contacting diisopropylamine with butyllithium is conducted at a temperature of ≤0° C., ≤−5° C., ≤−10° C., ≤−15° C., or ≤−20° C. In some embodiments, contacting diisopropylamine with butyllithium is conducted at a temperature of ≤−5° C.

In certain embodiments, contacting diisopropylamine with butyllithium is conducted in tetrahydrofuran (THF).

In certain embodiments, lithium diisopropylamide is prepared before step (a), for example, before contacting ethyl isobutyrate with 1-bromo-5-chloropentane.

In certain embodiments, lithium diisopropylamide is prepared in situ during step (a), for example, while contacting ethyl isobutyrate with 1-bromo-5-chloropentane. In some embodiments, when lithium diisopropylamide is prepared in situ during step (a), the molar ratio of the substituted 5-chloropentane to ethyl isobutyrate to butyllithium to diisopropylamine is about 1:1.1:1.2:1.26, about 1:1.1:1.15:1.75, about 1:1.1:1.24:1.3, about 1:1.1:1.2:1.29, about 1:1.1:1.2:1.28, or about 1:1-1.25:1.15-1.2:1.25-1.75. In some embodiments, when lithium diisopropylamide is prepared in situ during step (a), the molar ratio of the substituted 5-chloropentane to ethyl isobutyrate to butyllithium to diisopropylamine is about 1:1.1:1.2:1.28.

In some embodiments, the substituted 5-chloropentane is 1-bromo-5-chloropentane.

Synthesis of a Compound of Formula (II)—Step (b)

In various embodiments, the synthesis of a compound of formula (II):

wherein X is Br or I, generally comprises contacting the compound of formula (I) with a salt of formula [M]⁺[X]⁻.

In certain embodiments, in step (b), contacting the compound of formula (I) with a salt of formula [M]+[X]⁻, is conducted in a solvent comprising one or more of acetone, 2-butanone, methyl isobutyl ketone, THF and 3-pentanone, wherein M is selected from the group consisting of Li, Na, and K, and X is selected from the group consisting of Br and I.

In certain embodiments, in step (b), the solvent comprises less than about 3.5% by weight water, less than about 3% by weight water, less than about 2.5% by weight water, less than about 2% by weight water, less than about 1.5% by weight water, less than about 1% by weight water, or less than about 0.5% by weight water. In some embodiments, in step (b), the solvent comprises less than less than about 3% by weight water.

In certain embodiments, in step (b), contacting the compound of formula (I) with the salt of formula [M]⁺[X]⁻ comprises contacting the compound of formula (I) with about 1 molar equivalent, about 1.05 molar equivalents, about 1.1 molar equivalents, about 1.15 molar equivalents, about 1.2 molar equivalents, or about 1.25 molar equivalents of the salt of formula [M]⁺[X]⁻ based on the molar amount of the compound of formula (I). In certain embodiments, in step (b), contacting the compound of formula (I) with the salt of formula [M]⁺[X]⁻ comprises contacting the compound of formula (I) with about 1.1 molar equivalents of the salt of formula [M]⁺[X]⁻ based on the molar amount of the compound of formula (I).

In certain embodiments, in step (b), contacting the compound of formula (I) with the salt of formula [M]⁺[X]⁻ is conducted at a temperature in the range of from about 75° C. to about 85° C., from about 76° C. to about 85° C., from about 77° C. to about 85° C., from about 78° C. to about 85° C., from about 79° C. to about 85° C., from about 80° C. to about 85° C., from about 81° C. to about 85° C., from about 82° C. to about 85° C., from about 83° C. to about 85° C., from about 84° C. to about 85° C., from about 75° C. to about 84° C., from about 75° C. to about 83° C., from about 75° C. to about 82° C., from about 75° C. to about 81° C., from about 75° C. to about 80° C., from about 75° C. to about 79° C., from about 75° C. to about 78° C., from about 75° C. to about 77° C., from about 75° C. to about 76° C., from about 76° C. to about 84° C., from about 76° C. to about 83° C., from about 76° C. to about 82° C., from about 76° C. to about 81° C., from about 76° C. to about 80° C., from about 76° C. to about 79° C., from about 76° C. to about 78° C., from about 76° C. to about 77° C., from about 77° C. to about 84° C., from about 77° C. to about 83° C., from about 77° C. to about 82° C., from about 77° C. to about 81° C., from about 77° C. to about 80° C., from about 77° C. to about 79° C., from about 77° C. to about 78° C., from about 78° C. to about 84° C., from about 78° C. to about 83° C., from about 78° C. to about 82° C., from about 78° C. to about 81° C., from about 78° C. to about 80° C., from about 78° C. to about 79° C., from about 79° C. to about 84° C., from about 79° C. to about 83° C., from about 79° C. to about 82° C., from about 79° C. to about 81° C., from about 79° C. to about 80° C., from about 80° C. to about 84° C., from about 80° C. to about 83° C., from about 80° C. to about 82° C., from about 80° C. to about 81° C., from about 81° C. to about 84° C., from about 81° C. to about 83° C., from about 81° C. to about 82° C., from about 82° C. to about 84° C., from about 82° C. to about 83° C., or from about 83° C. to about 84° C. In some embodiments, in step (b), contacting the compound of formula (I) with the salt of formula [M]⁺[X]⁻ is conducted at a temperature in the range of from about 78° C. to about 82° C.

In certain embodiments, in step (b), the salt of formula [M]⁺[X]⁻ is selected from the group consisting of lithium bromide (LiBr), lithium iodide (LiI), potassium bromide (KBr), potassium iodide (KI), sodium bromide (NaBr) and sodium iodide (NaI). In some embodiments, in step (b), the salt of formula [M]⁺[X]⁻ is sodium iodide.

Synthesis of a Compound of Formula (IV)—Step (c)

In various embodiments, the synthesis of a compound of formula (IV):

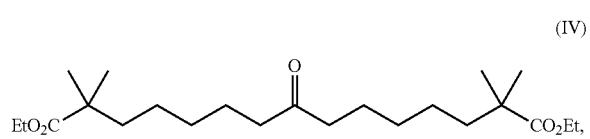

(IV)

generally comprises contacting the compound of formula (II) with toluenesulfonylmethyl isocyanide in the presence of a second base to form a first intermediate, and contacting the first intermediate with an acid.

Synthesis of the First Intermediate

In various embodiments, the synthesis of the first intermediate:

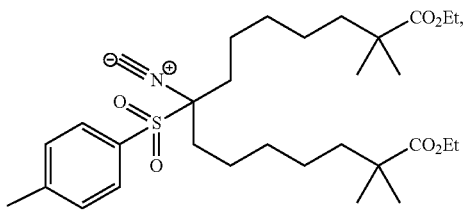 [SMILES: [C-]#[N+]C(CCCCCC(C)(C)C(=O)OCC)(CCCCCC(C)(C)C(=O)OCC)S(=O)(=O)c1ccc(C)cc1]

generally comprises contacting the compound of formula (II) with toluenesulfonylmethyl isocyanide in the presence of a second base.

In certain embodiments, in step (c), the second base is selected from sodium hydride, potassium tert-butoxide, and sodium tert-pentoxide. In some embodiments, in step (c), the second base is sodium tert-pentoxide.

In certain embodiments, in step (c), contacting the compound of formula (II) with toluenesulfonylmethyl isocyanide in the presence of sodium tert-pentoxide to form the first intermediate is conducted at a temperature in a range of from about −20° C. to about 10° C., from about −10° C. to about 10° C., from about 0° C. to about 10° C., from about −20° C. to about 0° C., from about −20° C. to about −10° C., or from about −10° C. to about 0° C. In certain embodiments, in step (c), contacting the compound of formula (II) with toluenesulfonylmethyl isocyanide in the presence of sodium tert-pentoxide to form the first intermediate is conducted at a temperature in a range of from about −20° C. to about 10° C. In certain embodiments, in step (c), contacting the compound of formula (II) with toluenesulfonylmethyl isocyanide in the presence of sodium tert-pentoxide to form the first intermediate is conducted at a temperature in a range of from about −15° C. to about 0° C.

In certain embodiments, in step (c), contacting the compound of formula (II) with toluenesulfonylmethyl isocyanide in the presence of a second base to form the first intermediate is conducted at a temperature of about −20° C., about −15° C., about −10° C., about −5° C., or about 0° C.

In certain embodiments, in step (c), the molar ratio of the compound of formula (II) to toluenesulfonylmethyl isocyanide is about 1.7:1, about 1.8:1, about 1.9:1, about 2:1, about 2.1:1, or about 2.2:1. In certain embodiments, in step (c), the molar ratio of the compound of formula (II) to toluenesulfonylmethyl isocyanide is about 1.9:1.

In some embodiments, in step (c), the molar ratio of the compound of formula (II) to toluenesulfonylmethyl isocyanide to the second base is about 1.9:1.0:2.1. In some embodiments, in step (c), the molar ratio of the compound of formula (II) to toluenesulfonylmethyl isocyanide to the second base is about 1.9:1.0:2.2.

In some embodiments, in step (c), the molar ratio of the compound of formula (II) to toluenesulfonylmethyl isocyanide to sodium tert-pentoxide is about 1.9:1.0:2.1. In some embodiments, in step (c), the molar ratio of the compound of formula (II) to toluenesulfonylmethyl isocyanide to sodium tert-pentoxide is about 1.9:1.0:2.2.

In certain embodiments, in step (c), contacting the compound of formula (II) with toluenesulfonylmethyl isocyanide is conducted in a solvent comprising dimethylacetamide or that is dimethylacetamide.

Synthesis of a Compound of Formula (IV)

In various embodiments, the synthesis of a compound of formula (IV):

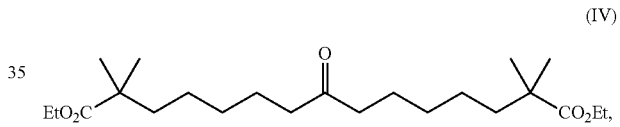

(IV)

generally comprises contacting the first intermediate with an acid.

In certain embodiments, in step (c), contacting the first intermediate with an acid is conducted at a temperature in a range of from about −15° C. to about 35° C., from about −10° C. to about 35° C., from about −5° C. to about 35° C., from about 0° C. to about 35° C., from about 5° C. to about 35° C., from about 10° C. to about 35° C., from about 15° C. to about 35° C., from about 20° C. to about 35° C., from about 25° C. to about 35° C., from about 30° C. to about 35° C., from about −15° C. to about 30° C., from about −15° C. to about 25° C., from about −15° C. to about 20° C., from about −15° C. to about 15° C., from about −15° C. to about 10° C., from about −15° C. to about 5° C., from about −15° C. to about 0° C., from about −15° C. to about −5° C., from about −15° C. to about −10° C., from about −10° C. to about 30° C., from about −10° C. to about 25° C., from about −10° C. to about 20° C., from about −10° C. to about 15° C., from about −10° C. to about 10° C., from about −10° C. to about 5° C., from about −10° C. to about −5° C., from about −5° C. to about 30° C., from about −5° C. to about 25° C., from about −5° C. to about 20° C., from about −5° C. to about 15° C., from about −5° C. to about 10° C., from about −5° C. to about 5° C., from about −5° C. to about 0° C., from about 0° C. to about 30° C., from about 0° C. to about 25° C., from about 0° C. to about 20° C., from about 0° C. to about 15° C., from about 0° C. to about 10° C., from about 0° C. to about 5° C., from about 5° C. to about 30° C., from about 5° C. to about 25° C., from about 5° C. to about 20° C., from about 5° C. to about 15° C., from about 5° C. to about 10° C., from about 10° C. to about 30° C., from about 10° C. to about 25° C., from about 10° C. to about 20° C., from about 10° C. to about 15° C., from about 15° C. to about 30° C., from about 15° C. to about 25° C., from about 15° C. to about 20° C., from about 20° C. to about 30° C., from about 20° C. to about 25° C., or from about 25° C. to about 30° C. In some embodiments, in step (c), contacting the first intermediate with an acid is conducted at a temperature in a range of from about −10° C. to about 35° C. In some embodiments, in step (c), contacting the first intermediate with an acid is conducted at a temperature in a range of from about −15° C. to about 25° C. In some embodiments, in step (c), contacting the first intermediate with an acid is conducted at a temperature in a range of from about 10° C. to about 25° C.

In certain embodiments, in step (c), the acid is hydrochloric acid.

Synthesis of a Compound of Formula (V)—Step (d)

In various embodiments the synthesis of a compound of formula (V):

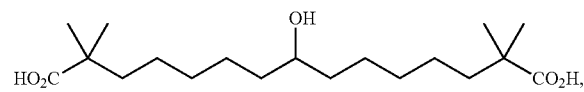

generally comprises contacting the compound of formula (IV) with a reducing agent to form a second intermediate, and contacting the second intermediate with a hydrolyzing base.

Synthesis of the Second Intermediate

In various embodiments, the synthesis of the second intermediate:

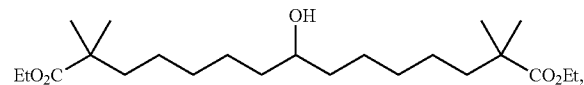

generally comprises contacting the compound of formula (IV) with a reducing agent.

In certain embodiments, in step (d), the reducing agent is selected from the group consisting of sodium borohydride, sodium cyanoborohydride, cerium borohydride, zinc borohydride and diisobutylaluminum hydride. In some embodiments, the reducing agent is sodium borohydride.

In certain embodiments, in step (d), contacting the compound of formula (IV) with a reducing agent comprises contacting the compound of formula (IV) with about 0.25 molar equivalents, about 0.3 molar equivalents, about 0.35 molar equivalents, about 0.4 molar equivalents, about 0.45, about 0.5 molar equivalents, about 0.6 molar equivalents, about 0.7 molar equivalents, about 0.8 molar equivalents, about 0.9 molar equivalents, about 1.0 molar equivalents, about 1.1 molar equivalents, about 1.2 molar equivalents, about 1.3 molar equivalents, about 1.4 molar equivalents, or about 1.5 molar equivalents of the reducing agent based on the molar amount of the compound of formula (IV). In some embodiments, in step (d), contacting the compound of formula (IV) with a reducing agent comprises contacting the compound of formula (IV) with about 0.35 molar equivalents of the reducing agent based on the molar amount of the compound of formula (IV).

In certain embodiments, in step (c), contacting the compound of formula (IV) with a reducing agent is conducted at a temperature in a range of from about 5° C. to about 30° C., from about 10° C. to about 30° C., from about 15° C. to about 30° C., from about 20° C. to about 30° C., from about 25° C. to about 30° C., from about 5° C. to about 25° C., from about 5° C. to about 20° C., from about 5° C. to about 15° C., from about 5° C. to about 10° C., from about 10° C. to about 25° C., from about 10° C. to about 20° C., from about 10° C. to about 15° C., from about 15° C. to about 25° C., from about 15° C. to about 20° C., or from about 20° C. to about 25° C.

In certain embodiments, in step (c), contacting the compound of formula (IV) with a reducing agent is conducted at a temperature of about 5° C., about 10° C., about 15° C., about 20° C., about 25° C., or about 30° C.

Synthesis of a Compound of Formula (V)

In various embodiments, the synthesis of a compound of formula (V):

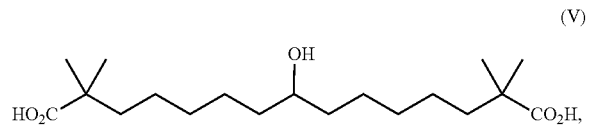

generally comprises contacting the second intermediate with a hydrolysing base.

In certain embodiments, in step (d), the concentration of the hydrolyzing base is about 20% w/w, about 25% w/w, about 30% w/w, about 35% w/w, about 40% w/w, about 45% w/w, about 50% w/w, about 55% w/w, or about 60% w/w. In some embodiments, in step (d), the concentration of the hydrolyzing base is about 50% w/w.

In certain embodiments, in step (d), contacting the second intermediate with a hydrolyzing base to form a compound of formula (V) is conducted in a solution. In some embodiments, in step (d), the method further comprises adjusting the pH of the solution comprising the compound of formula (V) to between about 3 to about 7.

In certain embodiments, in step (d), contacting the second intermediate with a hydrolyzing base is conducted at a temperature in a range of from about 30° C. to about 60° C., from about 35° C. to about 60° C., from about 40° C. to about 60° C., from about 45° C. to about 60° C., from about 50° C. to about 60° C., from about 55° C. to about 60° C., from about 30° C. to about 55° C., from about 30° C. to about 50° C., from about 30° C. to about 45° C., from about 30° C. to about 40° C., from about 30° C. to about 35° C., from about 35° C. to about 55° C., from about 35° C. to about 50° C., from about 35° C. to about 45° C., from about 35° C. to about 40° C., from about 40° C. to about 55° C., from about 40° C. to about 50° C., from about 40° C. to about 45° C., from about 45° C. to about 55° C., from about 45° C. to about 50° C., or from about 50° C. to about 60° C.

In certain embodiments, in step (d), contacting the second intermediate with a hydrolyzing base is conducted at a temperature of about 30° C., about 35° C., about 40° C., about 45° C., about 50° C., about 55° C., or about 60° C. In certain embodiments, in step (d), contacting the second intermediate with a hydrolyzing base is conducted at a temperature of about 50° C.

In certain embodiments, in step (d), the hydrolyzing base is sodium hydroxide.

In certain embodiments, in step (d), contacting the compound of formula (IV) with a reducing agent to form a second intermediate, and contacting the second intermediate with a hydrolyzing base to form a compound of formula (V) is conducted in a single reaction vessel.

In some embodiments of the present aspect, the methods can include:
(a) contacting ethyl isobutyrate with 1-bromo-5-chloropentane in the presence of a first base to form a compound of formula (I):

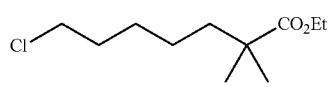
(I)

(b) contacting the compound of formula (I) with sodium iodide to form a compound of formula (IIa):

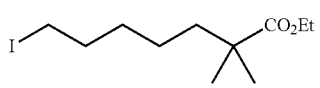
(IIa)

(c) contacting the compound of formula (IIa) with toluenesulfonylmethyl isocyanide in the presence of a second base to form a first intermediate, and contacting the first intermediate with an acid to form a compound of formula (IV):

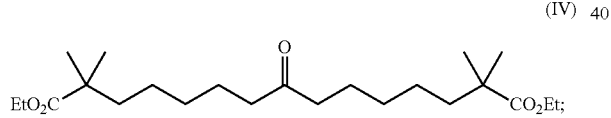
(IV)

and
(d) contacting the compound of formula (IV) with a reducing agent to form a second intermediate, and contacting the second intermediate with a hydrolyzing base to form a compound of formula (V).

In some embodiments of the invention, the method further comprises:
(e) purifying the compound of formula (V) to provide a pharmaceutical material comprising a purified amount of the compound of formula (V).

In some embodiments as described above, the same conditions (e.g., temperatures) amounts, ratios, equivalents, times, purities, and other parameters or variables that were previously described can be equally applicable, for example, where "1-bromo-5-chloropentane" is substituted for "substituted-5-chloropentane;" "sodium iodide" is substituted for "a salt of formula [M]⁺[X]⁻; "Na" is substituted for "M;" "I" is substituted for "X;" and a "compound of formula (IIa)" is substituted for a "compound of formula II."

In addition, in certain embodiments, the concentration of 1,5-dichloropentane in 1-bromo-5-chloropentane is ≤0.1%, ≤0.2%, ≤0.3%, ≤0.4%, ≤0.5%, ≤0.6%, ≤0.7%, ≤0.8%, ≤0.9%, or ≤1%, as measured by GC. In some embodiments, the concentration of 1,5-dichloropentane in 1-bromo-5-chloropentane is ≤0.5%, as measured by GC.

In certain embodiments, the concentration of 1,5-dibromopentane in 1-bromo-5-chloropentane is ≤0.05%, ≤0.1%, ≤0.15%, ≤0.2%, ≤0.25%, ≤0.3%, ≤0.35%, ≤0.4%, ≤0.45%, ≤0.5%, ≤0.6%, ≤0.7%, ≤0.8%, ≤0.9%, or ≤1.0%, as measured by GC. In some embodiments, the concentration of 1,5-dibromopentane in 1-bromo-5-chloropentane is ≤0.2%, as measured by GC. In some embodiments, the concentration of 1,5-dibromopentane in 1-bromo-5-chloropentane is ≤1.0%, as measured by GC.

In certain embodiments, the amount of unreacted 1-bromo-5-chloropentane remaining upon completion of step (a) is ≤0.05%, ≤0.06%, ≤0.07%, ≤0.08%, ≤0.09%, ≤0.1%, ≤0.11%, ≤0.12%, ≤0.12%, ≤0.13%, ≤0.14%, ≤0.15%, ≤0.16%, ≤0.17%, ≤0.18%, ≤0.19%, or ≤0.2%, as measured by GC. In some embodiments, the amount of unreacted 1-bromo-5-chloropentane remaining upon completion of step (a) is ≤0.21%, ≤0.22%, ≤0.23%, ≤0.24%, ≤0.25%, ≤0.25%, ≤0.26%, ≤0.27%, ≤0.28%, ≤0.29%, ≤0.3%, ≤0.31%, ≤0.32%, ≤0.33%, ≤0.34%, ≤0.35%, ≤0.36%, ≤0.37%, ≤0.38%, ≤0.39%, or ≤0.4%, as measured by GC.

In certain embodiments, a method of preparing a compound of formula (V) comprises:
(a) contacting 1-bromo-5-chloropentane with about 1.1 molar equivalents of ethyl isobutyrate in the presence of lithium diisopropylamide at a temperature in the range of from about −20° C. to about 0° C. to form a compound of formula (I):

(I)

(b) contacting the compound of formula (I) with about 1.1 molar equivalents of sodium iodide in 2-butanone at a temperature in the range of from about 78° C. to about 82° C. to form a compound of formula (IIa):

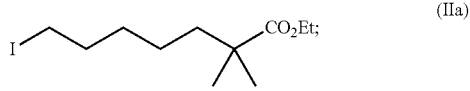
(IIa)

(c) contacting the compound of formula (IIa) with toluenesulfonylmethyl isocyanide in the presence of sodium tert-pentoxide in dimethylacetamide at a temperature in the range of from about −20° C. to about 10° C. to form a first intermediate, and contacting the first intermediate with an acid at a temperature in the range of from about −10° C. to about 35° C. to form a compound of formula (IV):

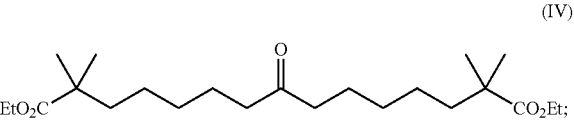 [SMILES: CCOC(=O)C(C)(C)CCCCCC(=O)CCCCCC(C)(C)C(=O)OCC]
(IV)

and
(d) contacting the compound of formula (IV) with about 0.35 molar equivalents of sodium borohydride to form a second intermediate, and contacting the second intermediate with sodium hydroxide in a solution to form a compound of formula (V).

In certain embodiments of the invention, the method further comprises:
(e) purifying the compound of formula (V) to provide a pharmaceutical material comprising a purified amount of the compound of formula (V).

In certain embodiments as described above, the same conditions (e.g., temperatures) amounts, ratios, equivalents, times, purities, and other parameters or variables that were previously described can be equally applicable, for example, where "lithium diisopropylamide" is substituted for "a first base;" "sodium tert-pentoxide" is substituted for "a second base;" "sodium borohydride" is substituted for "a reducing agent;" and "sodium hydroxide" is substituted for a hydrolyzing base."

In addition, in certain embodiments, in step (a), contacting ethyl isobutyrate with 1-bromo-5-chloropentane in the presence of lithium diisopropylamide is conducted at a temperature in the range of from about –20° C. to about 0° C., from about –15° C. to about 0° C., from about –10° C. to about 0° C., from about –5° C. to about 0° C., from about –20° C. to about –5° C., from about –20° C. to about –10° C., from about –20° C. to about –15° C., from about –15° C. to about –5° C., from about –15° C. to about –10° C., or from about –10° C. to about –5° C.

In certain embodiments, in step (b), contacting the compound of formula (I) with sodium iodide is conducted at a temperature in the range of from about 78° C. to about 82° C., from about 78° C. to about 80° C., or from about 80° C. to about 82° C.

In certain embodiments, in step (c), the molar ratio of the compound of formula (IIa) to toluenesulfonylmethyl isocyanide to sodium tert-pentoxide is about 1.9:1:2.1.

Purification of a Compound of Formula (V)—Step (e)

Various embodiments of the invention include methods for producing a pharmaceutical material comprising a purified amount of a compound of formula (V):

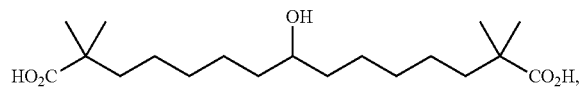

i.e., the methods can include purifying the compound of formula (V).

In various embodiments, purifying the compound of formula (V) comprises filtering the compound of formula (V) in a solvent through silica gel. In some embodiments, the solvent comprises ethyl acetate. In some embodiments, the solvent is ethyl acetate.

In certain embodiments, purifying the compound of formula (V) comprises crystallizing the compound of formula (V) to provide a crystalline form of the compound of formula (V).

In certain embodiments, purifying the compound of formula (V) comprises contacting the compound of formula (V) with charcoal and then filtering the charcoal. In some embodiments, contacting the compound of formula (V) with charcoal comprises contacting the compound of formula (V) with a solution, wherein the solution comprises acetonitrile and activated charcoal (e.g., 5% (w/w) activated charcoal).

In certain embodiments, purifying the compound of formula (V) comprises recrystallizing the crystalline form of the compound of formula (V) to provide a pharmaceutical material comprising a purified amount of the compound of formula (V).

In various embodiments, purifying the compound of formula (V) comprises:
(f) adjusting the pH of the solution comprising the compound of formula (V) to about 5 to about 6;
(g) extracting the compound of formula (V) from the solution using methyl tert-butyl ether to provide a methyl tert-butyl ether solution comprising the compound of formula (V);
(h) exchanging the methyl tert-butyl ether of the methyl tert-butyl ether solution with ethyl acetate to provide an ethyl acetate solution comprising the compound of formula (V);
(i) filtering the ethyl acetate solution comprising the compound of formula (V) through silica gel;
(j) crystallizing the compound of formula (V) using ethyl acetate and water to provide a crystalline form of the compound of formula (V); and
(k) recrystallizing the crystalline form of the compound of formula (V) using ethyl acetate and water to provide a pharmaceutical material comprising a purified amount of the compound of formula (V).

In certain embodiments, in step (g), extracting the compound of formula (V) from the solution using methyl tert-butyl ether is conducted at a temperature less than or equal to about 5° C., about 10° C., about 15° C., about 20° C., about 25° C., about 30° C., about 35° C., about 40° C., about 45° C., about 50° C., or about 55° C. In certain embodiments, in step (g), extracting the compound of formula (V) from the solution using methyl tert-butyl ether is conducted at a temperature less than or equal to about 15° C. In certain embodiments, in step (g), extracting the compound of formula (V) from the solution using methyl tert-butyl ether is conducted at a temperature less than or equal to about 50° C.

In certain embodiments, in step (j), crystallizing the compound of formula (V) using ethyl acetate and water is conducted over a temperature range of about 60° C. to about –10° C., about 55° C. to about –10° C., about 50° C. to about –10° C., about 45° C. to about –10° C., about 40° C. to about –10° C., about 35° C. to about –10° C., about 30° C. to about –10° C., about 25° C. to about –10° C., about 20° C. to about –10° C., about 15° C. to about –10° C., about 10° C. to about –10° C., about 5° C. to about –10° C., about 0° C. to about –10° C., about –5° C. to about –10° C., about 60° C. to about –5° C., about 55° C. to about –5° C., about 50° C. to about –5° C., about 45° C. to about –5° C., about 40° C. to about –5° C., about 35° C. to about –5° C., about 30° C. to about –5° C., about 25° C. to about –5° C., about 20° C. to about –5° C., about 15° C. to about –5° C., about 10° C. to about –5° C., about 5° C. to about –5° C., about 0° C. to about –5° C., about 60° C. to about 0° C., about 55° C. to about 0° C., about 50° C. to about 0° C., about 45° C. to about 0° C., about 40° C. to about 0° C., about 35° C. to about 0° C., about 30° C. to about 0° C., about 25° C. to about 0° C., about 20° C. to about 0° C., about 15° C. to about 0° C., about 10° C. to about 0° C., about 5° C. to about 0° C., about 60° C. to about 5° C., about 55° C. to about 5° C., about 50° C. to about 5° C., about 45° C. to about 5° C., about 40° C. to about 5° C., about 35° C. to about 5° C., about 30° C. to about 5° C., about 25° C. to about 5° C., about 20° C. to about 5° C., about 15° C. to about 5° C., about 10° C. to about 5° C., about 60° C. to about 10° C., about 55° C. to about 10° C., about 50° C. to about 10° C., about 45° C. to about 10° C., about 40° C. to about 10° C., about 35° C. to about 10° C., about 30° C. to about 10° C., about 25° C. to about 10° C., about 20° C. to about 10° C., about 15° C. to about 10° C., about 60° C. to about 15° C., about 55° C. to about 15° C., about 50° C. to about 15° C., about 45° C. to about 15° C., about 40° C. to about 15° C., about 35° C. to about 15° C., about 30° C. to about 15° C., about 25° C. to about 15° C., about 20° C. to about 15° C., about 60° C. to about 20° C., about 55° C. to about 20° C., about 50° C. to about 20° C., about 45° C. to about 20° C., about 40° C. to about 20° C., about 35° C. to about 20° C., about 30° C. to about 20° C., about 25° C. to about 20° C., about 60° C. to about 25° C., about 55° C. to about 25° C., about 50° C. to about 25° C., about 45° C. to about 25° C., about 40° C. to about 25° C., about 35° C. to about 25° C., about 30° C. to about 25° C., about 60° C. to about 30° C., about 55° C. to about 30° C., about 50° C. to about 30° C., about 45° C. to about 30° C., about 60° C. to about 35° C., about 55° C. to about 35° C., about 50° C. to about 35° C., about 45° C. to about 35° C., about 40° C. to about 35° C., about 60° C. to about 40° C., about 55° C. to about 40° C., about 50° C. to about 40° C., about 45° C. to about 40° C., about 60° C. to about 45° C., about 55° C. to about 45° C., about 50° C. to about 45° C., about 60° C. to about 50° C., about 55° C. to about 50° C., or about 60° C. to about 55° C. In certain embodiments, in step (j), crystallizing the compound of formula (V) using ethyl acetate and water is conducted over a temperature range of about 50° C. to about −5° C.

In certain embodiments, in step (k), recrystallizing the crystalline form of the compound of formula (V) using ethyl acetate and water is conducted over a temperature range of about 70° C. to about 5° C., about 65° C. to about 5° C., about 60° C. to about 5° C., about 55° C. to about 5° C., about 50° C. to about 5° C., about 45° C. to about 5° C., about 40° C. to about 5° C., about 35° C. to about 5° C., about 30° C. to about 5° C., about 25° C. to about 5° C., about 20° C. to about 5° C., about 15° C. to about 5° C., about 10° C. to about 5° C., about 70° C. to about 10° C., about 65° C. to about 10° C., about 60° C. to about 10° C., about 55° C. to about 10° C., about 50° C. to about 10° C., about 45° C. to about 10° C., about 40° C. to about 10° C., about 35° C. to about 10° C., about 30° C. to about 10° C., about 25° C. to about 10° C., about 20° C. to about 10° C., about 15° C. to about 10° C., about 70° C. to about 15° C., about 65° C. to about 15° C., about 60° C. to about 15° C., about 55° C. to about 15° C., about 50° C. to about 15° C., about 45° C. to about 15° C., about 40° C. to about 15° C., about 35° C. to about 15° C., about 30° C. to about 15° C., about 25° C. to about 15° C., about 20° C. to about 15° C., about 70° C. to about 20° C., about 65° C. to about 20° C., about 60° C. to about 20° C., about 55° C. to about 20° C., about 50° C. to about 20° C., about 45° C. to about 20° C., about 40° C. to about 20° C., about 35° C. to about 20° C., about 30° C. to about 20° C., about 25° C. to about 20° C., about 70° C. to about 25° C., about 65° C. to about 25° C., about 60° C. to about 25° C., about 55° C. to about 25° C., about 50° C. to about 25° C., about 45° C. to about 25° C., about 40° C. to about 25° C., about 35° C. to about 25° C., about 30° C. to about 25° C., about 70° C. to about 30° C., about 65° C. to about 30° C., about 60° C. to about 30° C., about 55° C. to about 30° C., about 50° C. to about 30° C., about 45° C. to about 30° C., about 40° C. to about 30° C., about 70° C. to about 35° C., about 65° C. to about 35° C., about 60° C. to about 35° C., about 55° C. to about 35° C., about 50° C. to about 35° C., about 45° C. to about 35° C., about 40° C. to about 35° C., about 70° C. to about 40° C., about 65° C. to about 40° C., about 60° C. to about 40° C., about 55° C. to about 40° C., about 50° C. to about 40° C., about 45° C. to about 40° C., about 70° C. to about 45° C., about 65° C. to about 45° C., about 60° C. to about 45° C., about 55° C. to about 45° C., about 50° C. to about 45° C., about 70° C. to about 50° C., about 65° C. to about 50° C., about 60° C. to about 50° C., about 55° C. to about 50° C., about 70° C. to about 55° C., about 65° C. to about 55° C., about 60° C. to about 55° C., about 70° C. to about 60° C., about 65° C. to about 60° C., or about 70° C. to about 65° C. In certain embodiments, in step (k), recrystallizing the crystalline form of the compound of formula (V) using ethyl acetate and water is conducted over a temperature range of about 70° C. to about 5° C.

In certain embodiments, purifying the compound of formula (V) comprises:
 (l) dissolving the crystalline form of the compound of formula (V) in acetonitrile, thereby forming a solution;
 (m) contacting the solution with charcoal;
 (n) filtering the charcoal to provide a purified solution comprising the compound of formula (V); and
 (o) crystallizing the compound of formula (V) from the purified solution to provide a pharmaceutical material comprising a purified amount of the compound of formula (V).

It should be understood that, in various embodiments, the above steps (1)-(o) can be conducted after or without conducting steps (f)-(k).

Crystallization of the Compound of Formula (V)

In various embodiments, purifying the compound of formula (V) comprises crystallizing the compound of formula (V) from a solvent or a mixture of solvents, for example, ethyl acetate and water.

In certain embodiments, the concentration of water in the mixture of solvents comprising ethyl acetate and water is about 0.5% (w/w), about 0.6% (w/w), about 0.75% (w/w), about 0.9% (w/w), about 1.05% (w/w), about 1.2% (w/w), about 1.35% (w/w), about 1.4% (w/w), or about 1.5% (w/w).

In some embodiments, the concentration of water in the mixture of solvents comprising ethyl acetate and water is about 1.05% (w/w).

In certain embodiments, the concentration of water in the mixture of solvents comprising ethyl acetate and water is from about 0.5% (w/w) to about 1.5% (w/w), from about 0.5% (w/w) to about 1.4% (w/w), from about 0.5% (w/w) to about 1.35% (w/w), from about 0.5% (w/w) to about 1.2% (w/w), from about 0.5% (w/w) to about 1.05% (w/w), from about 0.5% (w/w) to about 0.9% (w/w), from about 0.5% (w/w) to about 0.75% (w/w), from about 0.5% (w/w) to about 0.6% (w/w), from about 0.6% (w/w) to about 1.5% (w/w), from about 0.6% (w/w) to about 1.4% (w/w), from about 0.6% (w/w) to about 1.35% (w/w), from about 0.6% (w/w) to about 1.2% (w/w), from about 0.6% (w/w) to about 1.05% (w/w), from about 0.6% (w/w) to about 0.9% (w/w), from about 0.6% (w/w) to about 0.75% (w/w), from about 0.75% (w/w) to about 1.5% (w/w), from about 0.75% (w/w) to about 1.4% (w/w), from about 0.75% (w/w) to about 1.35% (w/w), from about 0.75% (w/w) to about 1.2% (w/w), from about 0.75% (w/w) to about 1.05% (w/w), from about 0.75% (w/w) to about 0.9% (w/w), from about 0.9% (w/w) to about 1.5% (w/w), from about 0.9% (w/w) to about 1.35% (w/w), from about 0.9% (w/w) to about 1.2% (w/w), from about 0.9% (w/w) to about 1.05% (w/w), from about 1.05% (w/w) to about 1.5% (w/w), from about 1.05% (w/w) to about 1.35% (w/w), from about 1.05% (w/w) to about 1.2% (w/w), from about 1.2% (w/w) to about 1.5% (w/w), from about 1.2%

(w/w) to about 1.35% (w/w), or from about 1.35% (w/w) to about 1.5% (w/w). In some embodiments, the concentration of water in the mixture of solvents comprising ethyl acetate and water is from about 0.6% (w/w) to about 1.4% (w/w). In some embodiments, the concentration of water in the mixture of solvents comprising ethyl acetate and water is from about 0.75% (w/w) to about 1.35% (w/w).

In various embodiments, crystallizing the compound of formula (V) from a mixture comprising the compound of formula (V), ethyl acetate and water comprises:
(1) cooling the mixture from a first temperature ($T^1$) to a second temperature ($T^2$), wherein $T^1$ is from about 40° C. to about 60° C., $T^2$ is from about 15° C. to about 30° C., and the mixture is cooled from $T^1$ to $T^2$ at a rate of from about 10° C./hour to about 20° C./hour;
(2) holding the mixture at $T^2$ for at least 3 hours;
(3) cooling the mixture from $T^2$ to a third temperature ($T^3$), wherein $T^3$ is from about −5° C. to about 10° C. and the mixture is cooled from $T^2$ to $T^3$ at a rate of from about 5° C./hour to about 15° C./hour; and
(4) holding the mixture at $T^3$ for at least 3 hours, thereby producing a crystalline form of the compound of formula (V).

In certain embodiments, in crystallization step (1), $T^1$ is from about 40° C. to about 60° C., from about 45° C. to about 60° C., from about 50° C. to about 60° C., from about 55° C. to about 60° C., from about 40° C. to about 55° C., from about 40° C. to about 50° C., from about 40° C. to about 45° C., from about 45° C. to about 55° C., from about 45° C. to about 50° C., or from about 50° C. to about 55° C. In some embodiments, in crystallization step (1), $T^1$ is from about 40° C. to about 60° C. In some embodiments, in crystallization step (1), $T^1$ is from about 45° C. to about 55° C.

In certain embodiments, in crystallization step (1), $T^1$ is about 40° C., about 45° C., about 50° C., about 55° C., or about 60° C. In some embodiments, in crystallization step (1), $T^1$ is about 50° C.

In certain embodiments, in crystallization step (1), $T^2$ is from about 15° C. to about 30° C., from about 20° C. to about 30° C., from about 25° C. to about 30° C., from about 15° C. to about 25° C., from about 15° C. to about 20° C., or from about 20° C. to about 25° C. In some embodiments, in crystallization step (i), $T^2$ is from about 15° C. to about 30° C. In some embodiments, in crystallization step (1), $T^2$ is from about 20° C. to about 25° C.

In certain embodiments, in crystallization step (1), $T^2$ is about 15° C., about 16° C., about 17° C., about 18° C., about 19° C., about 20° C., about 21° C., about 22° C., about 23° C., about 24° C., about 25° C., about 26° C., about 27° C., about 28° C., about 29° C., or about 30° C. In some embodiments, in crystallization step (1), $T^2$ is about 22° C.

In certain embodiments, in crystallization step (1), the mixture is cooled from $T^1$ to $T^2$ at a rate of from about 10° C./hour to about 20° C./hour, from about 12° C./hour to about 20° C./hour, from about 14° C./hour to about 20° C./hour, from about 16° C./hour to about 20° C./hour, from about 18° C./hour to about 20° C./hour, from about 10° C./hour to about 18° C./hour, from about 10° C./hour to about 16° C./hour, from about 10° C./hour to about 14° C./hour, from about 10° C./hour to about 12° C./hour, from about 12° C./hour to about 18° C./hour, from about 12° C./hour to about 16° C./hour, from about 12° C./hour to about 14° C./hour, from about 14° C./hour to about 18° C./hour, from about 14° C./hour to about 16° C./hour, or from about 16° C./hour to about 18° C./hour. In some embodiments, the mixture is cooled from $T^1$ to $T^2$ at a rate of from about 10° C./hour to about 20° C./hour. In some embodiments, the mixture is cooled from $T^1$ to $T^2$ at a rate of from about 10° C./hour to about 12° C./hour.

In certain embodiments, in crystallization step (1), the mixture is cooled from $T^1$ to $T^2$ at a rate of about 10° C./hour, about 11° C./hour, about 12° C./hour, about 13° C./hour, about 14° C./hour, about 15° C./hour, about 16° C./hour, about 17° C./hour, about 18° C./hour, about 19° C./hour, or about 20° C./hour. In certain embodiments, in crystallization step (1), the mixture is cooled from $T^1$ to $T^2$ at a rate of about 11° C./hour.

In certain embodiments, in crystallization step (2), the mixture is held at $T^2$ for at least 3 hours, at least 3.5 hours, at least 4 hours, at least 4.5 hours, at least 5 hours, at least 5.5 hours, at least 6 hours, at least 6.5 hours, at least 7 hours, at least 7.5 hours, at least 8 hours, at least 8.5 hours, at least 9 hours, at least 9.5 hours, or at least 10 hours. In some embodiments, in crystallization step (2), the mixture is held at $T^2$ for at least 6 hours.

In certain embodiments, in crystallization step (2), the mixture is held at $T^2$ for no greater than 3 hours, no greater than 3.5 hours, no greater than 4 hours, no greater than 4.5 hours, no greater than 5 hours, no greater than 5.5 hours, no greater than 6 hours, no greater than 6.5 hours, no greater than 7 hours, no greater than 7.5 hours, no greater than 8 hours, no greater than 8.5 hours, no greater than 9 hours, no greater than 9.5 hours, no greater than 10 hours, no greater than 10.5 hours, no greater than 11 hours, no greater than 11.5 hours, no greater than 12 hours, no greater than 16 hours, no greater than 20 hours, or no greater than 24 hours. In some embodiments, in crystallization step (2), the mixture is held at $T^2$ for no greater than 6 hours.

In certain embodiments, in crystallization step (3), $T^3$ is from about −5° C. to about 10° C., from about 0° C. to about 10° C., from about 5° C. to about 10° C., from about −5° C. to about 5° C., from about −5° C. to about 0° C., or from about 0° C. to about 5° C. In some embodiments, $T^3$ is from about −5° C. to about 10° C. In some embodiments, $T^3$ is from about −5° C. to about 5° C.

In certain embodiments, in crystallization step (3), $T^3$ is about −5° C., about 0° C., about 5° C., or about 10° C. In some embodiments, in crystallization step (3), $T^3$ is about 0° C.

In certain embodiments, in crystallization step (3), the mixture is cooled from $T^2$ to $T^3$ at a rate of from about 5° C./hour to about 15° C./hour, from about 7° C./hour to about 15° C./hour, from about 9° C./hour to about 15° C./hour, from about 11° C./hour to about 15° C./hour, from about 13° C./hour to about 15° C./hour, from about 5° C./hour to about 13° C./hour, from about 5° C./hour to about 11° C./hour, from about 5° C./hour to about 9° C./hour, from about 5° C./hour to about 7° C./hour, from about 7° C./hour to about 13° C./hour, from about 7° C./hour to about 11° C./hour, from about 7° C./hour to about 9° C./hour, from about 9° C./hour to about 13° C./hour, from about 9° C./hour to about 11° C./hour, or from about 11° C./hour to about 13° C./hour. In some embodiments, in crystallization step (3), the mixture is cooled from $T^2$ to $T^3$ at a rate of from about 5° C./hour to about 15° C./hour. In some embodiments, in crystallization step (3), the mixture is cooled from $T^2$ to $T^3$ at a rate of from about 7° C./hour to about 13° C./hour.

In certain embodiments, in crystallization step (3), the mixture is cooled from $T^2$ to $T^3$ at a rate of about 5° C./hour, about 6° C./hour, about 7° C./hour, about 8° C./hour, about 9° C./hour, about 10° C./hour, about 11° C./hour, about 12° C./hour, about 13° C./hour, about 14° C./hour, or about 15°

C./hour. In some embodiments, in crystallization step (3), the mixture is cooled from $T^2$ to $T^3$ at a rate of about 11° C./hour.

In certain embodiments, in crystallization step (4), the mixture is held at $T^3$ for at least 3 hours, at least 3.5 hours, at least 4 hours, at least 4.5 hours, at least 5 hours, at least 5.5 hours, at least 6 hours, at least 6.5 hours, at least 7 hours, at least 7.5 hours, at least 8 hours, at least 8.5 hours, at least 9 hours, at least 9.5 hours, or at least 10 hours. In some embodiments, in crystallization step (4), the mixture is held at $T^3$ for at least 6 hours.

In certain embodiments, in crystallization step (4), the mixture is held at $T^1$ for no greater than 3 hours, no greater than 3.5 hours, no greater than 4 hours, no greater than 4.5 hours, no greater than 5 hours, no greater than 5.5 hours, no greater than 6 hours, no greater than 6.5 hours, no greater than 7 hours, no greater than 7.5 hours, no greater than 8 hours, no greater than 8.5 hours, no greater than 9 hours, no greater than 9.5 hours, no greater than 10 hours, no greater than 10.5 hours, no greater than 11 hours, no greater than 11.5 hours, no greater than 12 hours, no greater than 16 hours, no greater than 20 hours, or no greater than 24 hours. In some embodiments, in crystallization step (4), the mixture is held at $T^3$ for no greater than 10 hours.

In certain embodiments, crystallizing the compound of formula (V) from a mixture comprising the compound of formula (V), ethyl acetate and water further comprises seeding the mixture with an amount of a crystalline form of the compound of formula (V) prior to crystallization step (1), during crystallization step (1), during crystallization step (2), during crystallization step (3), during crystallization step (4), or any combination thereof, in order to facilitate the crystallization of the compound of formula (V).

In certain embodiments, the amount of seed added to the mixture is about 0.001 kg/kg, about 0.0012 kg/kg, about 0.0014 kg/kg, about 0.0016 kg/kg, about 0.0018 kg/kg, or about 0.002 kg/kg, based on the weight of seed per kilogram of the compound of formula (IV) produced in step (c). In some embodiments, the amount of seed added to the mixture is about 0.0014 kg/kg, based on the weight of seed per kilogram of the compound of formula (IV) produced in step (c).

In certain embodiments, the crystalline form of the compound of formula (V) added as seed to the mixture may be a crystalline form of the compound of formula (V) as characterized herein, for example, by an X-ray powder diffraction pattern or peak(s), and/or other characteristic properties of the crystalline form of bempedoic acid.

In certain embodiments, crystallizing the compound of formula (V) from a mixture comprising the compound of formula (V), ethyl acetate and water comprises filtration of the compound of formula (V).

In certain embodiments, filtering the crystalline form of the compound of formula (V) occurs at a temperature of from about −20° C. to about 5° C., from about −15° C. to about 5° C., from about −10° C. to about 5° C., from about −5° C. to about 5° C., from about 0° C. to about 5° C., from about −20° C. to about 0° C., from about −20° C. to about −5° C., from about −20° C. to about −10° C., from about −20° C. to about −15° C., from about −15° C. to about 5° C., from about −15° C. to about 0° C., from about −15° C. to about −5° C., from about −15° C. to about −10° C., from about −10° C. to about 5° C., from about −10° C. to about 0° C., from about −10° C. to about −5° C., from about −5° C. to about 5° C., from about −5° C. to about 0° C., or from about 0° C. to about 5° C. In some embodiments, filtering the crystalline form of the compound of formula (V) occurs at a temperature of from about −20° C. to about −5° C. In some embodiments, filtering the crystalline form of the compound of formula (V) occurs at a temperature of about −5° C. to about 5° C.

In certain embodiments, filtering the crystalline form of the compound of formula (V) occurs at a temperature of about −20° C., about −15° C., about −10° C., about −5° C., about 0° C., or about 5° C. In some embodiments, filtering the crystalline form of the compound of formula (V) occurs at a temperature of about −10° C., about −5° C., or about 0° C.

In certain embodiments, filtration further comprises washing. In certain embodiments, washing comprises washing the crystalline form of the compound of formula (V) with a solvent. In some embodiments, washing comprises washing the crystalline form of the compound of formula (V) with ethyl acetate.

In certain embodiments, the temperature of the solvent, for example, ethyl acetate, is from about −20° C. to about 10° C., from about −10° C. to about 10° C., from about 0° C. to about 10° C., from about −20° C. to about 0° C., from about −20° C. to about −10° C., or from about −10° C. to about 0° C. In some embodiments, the temperature of the solvent is from about −10° C. to about 10° C.

In certain embodiments, the temperature of the solvent, for example, ethyl acetate, is about −20° C., about −15° C., about −10° C., about −5° C., about 0° C., about 5° C., or about 10° C.

In some embodiments, the temperature of the solvent is about 0° C.

In various embodiments, crystallizing the compound of formula (V) from a mixture comprising the compound of formula (V), ethyl acetate and water comprises:
(1) cooling the mixture from a first temperature ($T^1$) to a second temperature ($T^2$), wherein $T^1$ is about 50° C., $T^2$ is about 22° C., and the mixture is cooled from $T^1$ to $T^2$ at a rate of about 11° C./hour;
(2) holding the compound of formula (V) at $T^2$ for at least 6 hours;
(3) cooling the compound of formula (V) from $T^2$ to a third temperature ($T^3$), wherein $T^3$ is about 0° C. and the mixture is cooled from $T^2$ to $T^3$ at a rate of about 11° C./hour; and
(4) holding the compound of formula (V) at $T^3$ for at least 6 hours, thereby producing a crystalline form of the compound of formula (V).

It should be understood that the conditions (e.g., temperatures), times, seeding, amounts, compounds, and other parameters and/or variables for crystallizing the compound of formula (V) as described herein can be equally applicable to the immediately above-described crystallizing process, unless otherwise stated or understood from the context (e.g., the conditions or parameters fall outside the values or ranges in the immediately above-described crystallizing process).

In certain embodiments, the crystalline form of the compound of formula (V) produced by any of the crystallization methods described herein may be a crystalline form of the compound of formula (V) as characterized herein, for example, by an X-ray powder diffraction pattern or peak(s), and/or other characteristic properties of the crystalline form of bempedoic acid.

In certain embodiments, the purity of the crystalline form of the compound of formula (V) produced by any of the crystallization methods described herein is greater than about 85%, greater than about 90%, greater than about 95%, greater than about 96%, greater than about 97%, greater than about 98%, greater than about 99%, greater than about 99.1%, greater than about 99.2%, greater than about 99.3%, greater than about 99.4%, greater than about 99.5%, greater than about 99.6%, greater than about 99.7%, greater than about 99.8%, greater than about 99.85%, greater than about 99.9%, greater than about 99.95%, or greater than about 99.98% by weight of the total weight of the crystalline form of the compound of formula (V).

Recrystallization of the Crystalline Form of the Compound of Formula (V)

In various embodiments, in step (e), purifying the compound of formula (V) comprises one or more recrystallizations of the crystalline form of the compound of formula (V) to provide a pharmaceutical material comprising a purified amount of the compound of formula (V).

In certain embodiments, the one or more recrystallizations of the crystalline form of the compound of formula (V) comprises:

(1) dissolving the crystalline compound of formula (V) in one or more solvents, thereby forming a mixture;
(2) cooling the mixture from a first temperature ($T^1$) to a second temperature ($T^2$), wherein $T^1$ is from about 40° C. to about 65° C., $T^2$ is from about 20° C. to about 40° C., and the mixture is cooled from $T^1$ to $T^2$ at a rate of from about 3° C./hour to about 11° C./hour;
(3) holding the mixture at $T^2$ for at least 0.5 hours;
(4) heating the mixture from $T^2$ to a third temperature ($T^3$), wherein $T^3$ is from about 30° C. to about 50° C., and the mixture is heated from $T^2$ to $T^3$ at a rate of from about 3° C./hour to about 11° C./hour;
(5) holding the mixture at $T^3$ for at least 0.5 hours;
(6) cooling the mixture from $T^3$ to a fourth temperature ($T^4$), wherein $T^4$ is from about 25° C. to about 40° C. and the mixture is cooled from $T^3$ to $T^4$ at a rate of from about 3° C./hour to about 11° C./hour;
(7) holding the mixture at $T^4$ for at least 0.5 hours;
(8) cooling the mixture from $T^4$ to a fifth temperature ($T^5$), wherein $T^5$ is from about −10° C. to about 10° C. and the mixture is cooled from $T^4$ to $T^5$ at a rate of from about 3° C./hour to about 11° C./hour; and
(9) holding the mixture at $T^5$ for at least 0.5 hours, thereby producing a pharmaceutical material comprising a purified amount of crystalline form of the compound of formula (V).

In certain embodiments, in recrystallization step (1), the one or more solvents comprises ethyl acetate and water. In certain embodiments, the one or more solvents are ethyl acetate and water.

In certain embodiments, in recrystallization step (1), the amount of ethyl acetate in the mixture is from about 2.5 kg/kg to about 3.3 kg/kg, from about 2.7 kg/kg to about 3.3 kg/kg, from about 2.9 kg/kg to about 3.3 kg/kg, from about 3.1 kg/kg to about 3.3 kg/kg, from about 2.5 kg/kg to about 3.1 kg/kg, from about 2.5 kg/kg to about 2.9 kg/kg, from about 2.5 kg/kg to about 2.7 kg/kg, from about 2.7 kg/kg to about 3.1 kg/kg, from about 2.7 kg/kg to about 2.9 kg/kg, or from about 2.9 kg/kg to about 3.1 kg/kg, based on the weight of ethyl acetate per kilogram of the crystalline compound of formula (V). In some embodiments, in recrystallization step (1), the amount of ethyl acetate in the mixture is from about 2.5 kg/kg to about 3.3 kg/kg, based on the weight of ethyl acetate per kilogram of the crystalline compound of formula (V). In some embodiments, in recrystallization step (1), the amount of ethyl acetate in the mixture is from about 2.7 kg/kg to about 3.1 kg/kg, based on the weight of ethyl acetate per kilogram of the crystalline compound of formula (V).

In certain embodiments, in recrystallization step (1), the amount of ethyl acetate in the mixture is about 2.5 kg/kg, about 2.7 kg/kg, about 2.9 kg/kg, about 3.1 kg/kg, or about 3.3 kg/kg, based on the weight of ethyl acetate per kilogram of the crystalline compound of formula (V). In some embodiments, in recrystallization step (1), the amount of ethyl acetate in the mixture is about 2.9 kg/kg, based on the weight of ethyl acetate per kilogram of the crystalline compound of formula (V).

In certain embodiments, in recrystallization step (2), $T^1$ is from about 40° C. to about 65° C., from about 45° C. to about 65° C., from about 50° C. to about 65° C., from about 55° C. to about 65° C., from about 60° C. to about 65° C., from about 40° C. to about 60° C., from about 40° C. to about 55° C., from about 40° C. to about 50° C., from about 40° C. to about 45° C., from about 45° C. to about 60° C., from about 45° C. to about 55° C., from about 45° C. to about 50° C., from about 50° C. to about 60° C., from about 50° C. to about 55° C., or from about 55° C. to about 60 GC. In some embodiments, in recrystallization step (2), $T^1$ is from about 40° C. to about 65° C. In some embodiments, in recrystallization step (2), $T^1$ is from about 50° C. to about 60° C.

In certain embodiments, in recrystallization step (2), $T^1$ is about 40° C., about 45° C., about 50° C., about 55° C., about 60° C., or about 65° C. In some embodiments, in recrystallization step (2), $T^1$ is about 55° C.

In certain embodiments, in recrystallization step (2), $T^2$ is from about 20° C. to about 40° C., from about 25° C. to about 40° C., from about 30° C. to about 40° C., from about 35° C. to about 40° C., from about 20° C. to about 35° C., from about 20° C. to about 30° C., from about 20° C. to about 25° C., from about 25° C. to about 35° C., from about 25° C. to about 30° C., or from about 30° C. to about 40° C. In certain embodiments, in recrystallization step (2), $T^2$ is from about 25° C. to about 35° C.

In certain embodiments, in recrystallization step (2), $T^1$ is about 20° C., about 25° C., about 30° C., about 35° C., or about 40° C. In some embodiments, in recrystallization step (2), $T^1$ is about 30° C.

In certain embodiments, in recrystallization step (2), the mixture is cooled from $T^1$ to $T^2$ at a rate of from about 3° C./hour to about 11° C./hour, from about 5° C./hour to about 11° C./hour, from about 7° C./hour to about 11° C./hour, from about 9° C./hour to about 11° C./hour, from about 3° C./hour to about 9° C./hour, from about 3° C./hour to about 7° C./hour, from about 3° C./hour to about 5° C./hour, from about 5° C./hour to about 9° C./hour, from about 5° C./hour to about 7° C./hour, or from about 7° C./hour to about 9° C./hour. In some embodiments, in recrystallization step (2), the mixture is cooled from $T^1$ to $T^2$ at a rate of from about 3° C./hour to about 11° C./hour. In some embodiments, in recrystallization step (2), the mixture is cooled from $T^1$ to $T^2$ at a rate of from about 5° C./hour to about 7° C./hour.

In certain embodiments, in recrystallization step (2), the mixture is cooled from $T^1$ to $T^2$ at a rate of about 3° C./hour, about 4° C./hour, about 5° C./hour, about 6° C./hour, about 7° C./hour, about 8° C./hour, about 9° C./hour, about 10° C./hour, or about 11° C./hour. In some embodiments, in recrystallization step (2), the mixture is cooled from $T^1$ to $T^2$ at a rate of about 5° C./hour, about 6° C./hour, or about 7° C./hour.

In certain embodiments, in recrystallization step (3), the mixture is held at $T^2$ for at least 1 hour, 1.5 hours, 2 hours, 2.5 hours, 3 hours, 3.5 hours, 4 hours, 4.5 hours, 5 hours, 5.5 hours, 6 hours, 6.5 hours, at least 7 hours, at least 7.5 hours, at least 8 hours, at least 8.5 hours, at least 9 hours, at least 9.5 hours, or at least 10 hours. In some embodiments, in recrystallization step (3), the mixture is held at $T^2$ for at least 2 hours.

In certain embodiments, in recrystallization step (3), the mixture is held at $T^2$ for no greater than 1 hour, no greater than 1.5 hours, no greater than 2 hours, no greater than 2.5 hours, no greater than 3 hours, no greater than 3.5 hours, no greater than 4 hours, no greater than 4.5 hours, no greater than 5 hours, no greater than 5.5 hours, no greater than 6 hours, no greater than 6.5 hours, no greater than 7 hours, no greater than 7.5 hours, no greater than 8 hours, no greater than 8.5 hours, no greater than 9 hours, no greater than 9.5 hours, no greater than 10 hours, no greater than 10.5 hours, no greater than 11 hours, no greater than 11.5 hours, no greater than 12 hours, no greater than 16 hours, no greater than 20 hours, or no greater than 24 hours. In some embodiments, in recrystallization step (3), the mixture is held at $T^2$ for no greater than 2 hours.

In certain embodiments, in recrystallization step (4), $T^3$ is from about 30° C. to about 50° C., from about 35° C. to about 50° C., from about 40° C. to about 50° C., from about 45° C. to about 50° C., from about 30° C. to about 45° C., from about 30° C. to about 40° C., from about 30° C. to about 35° C., from about 35° C. to about 45° C., from about 35° C. to about 40° C., or from about 40° C. to about 45° C. In some embodiments, in recrystallization step (4), $T^3$ is from about 30° C. to about 50° C. In some embodiments, in recrystallization step (4), $T^3$ is from about 35° C. to about 45° C.

In certain embodiments, in recrystallization step (4), $T^3$ is about 30° C., about 35° C., about 40° C., about 45° C., or about 50° C. In some embodiments, in recrystallization step (4), $T^3$ is about 40° C.

In certain embodiments, in recrystallization step (4), the mixture is heated from $T^2$ to $T^3$ at a rate of from about 3° C./hour to about 11° C./hour, from about 5° C./hour to about 11° C./hour, from about 7° C./hour to about 11° C./hour, from about 9° C./hour to about 11° C./hour, from about 3° C./hour to about 9° C./hour, from about 3° C./hour to about 7° C./hour, from about 3° C./hour to about 5° C./hour, from about 5° C./hour to about 9° C./hour, from about 5° C./hour to about 7° C./hour, or from about 7° C./hour to about 9° C./hour. In some embodiments, in recrystallization step (4), the mixture is heated from $T^2$ to $T^3$ at a rate of from about 3° C./hour to about 11° C./hour. In some embodiments, in recrystallization step (4), the mixture is heated from $T^2$ to $T^3$ at a rate of from about 5° C./hour to about 7° C./hour.

In certain embodiments, in recrystallization step (4), the mixture is heated from $T^2$ to $T^3$ at a rate of about 3° C./hour, about 4° C./hour, about 5° C./hour, about 6° C./hour, about 7° C./hour, about 8° C./hour, about 9° C./hour, about 10° C./hour, or about 11° C./hour. In some embodiments, in recrystallization step (4), the mixture is heated from $T^2$ to $T^3$ at a rate of about 5° C./hour, about 6° C./hour, or about 7° C./hour.

In certain embodiments, in recrystallization step (5), the mixture is held at $T^3$ for at least 1 hour, 1.5 hours, 2 hours, 2.5 hours, 3 hours, 3.5 hours, 4 hours, 4.5 hours, 5 hours, 5.5 hours, 6 hours, 6.5 hours, at least 7 hours, at least 7.5 hours, at least 8 hours, at least 8.5 hours, at least 9 hours, at least 9.5 hours, or at least 10 hours. In some embodiments, in recrystallization step (5), the mixture is held at $T^3$ for at least 1 hour.

In certain embodiments, in recrystallization step (5), the mixture is held at $T^3$ for no greater than 1 hour, no greater than 1.5 hours, no greater than 2 hours, no greater than 2.5 hours, no greater than 3 hours, no greater than 3.5 hours, no greater than 4 hours, no greater than 4.5 hours, no greater than 5 hours, no greater than 5.5 hours, no greater than 6 hours, no greater than 6.5 hours, no greater than 7 hours, no greater than 7.5 hours, no greater than 8 hours, no greater than 8.5 hours, no greater than 9 hours, no greater than 9.5 hours, no greater than 10 hours, no greater than 10.5 hours, no greater than 11 hours, no greater than 11.5 hours, no greater than 12 hours, no greater than 16 hours, no greater than 20 hours, or no greater than 24 hours.

In certain embodiments, in recrystallization step (6), $T^4$ is from about 25° C. to about 40° C., from about 30° C. to about 40° C., from about 35° C. to about 40° C., from about 25° C. to about 35° C., from about 25° C. to about 30° C., or from about 30° C. to about 35° C. In some embodiments, in recrystallization step (6), $T^4$ is from about 25° C. to about 40° C. In some embodiments, in recrystallization step (6), $T^4$ is from about 30° C. to about 40° C.

In certain embodiments, in recrystallization step (6), $T^4$ is about 25° C., about 30° C., about 35° C., or about 40° C. In some embodiments, in recrystallization step (6), $T^4$ is about 35° C.

In certain embodiments, in recrystallization step (6), the mixture is cooled from $T^3$ to $T^4$ at a rate of from about 3° C./hour to about 11° C./hour, from about 5° C./hour to about 11° C./hour, from about 7° C./hour to about 11° C./hour, from about 9° C./hour to about 11° C./hour, from about 3° C./hour to about 9° C./hour, from about 3° C./hour to about 7° C./hour, from about 3° C./hour to about 5° C./hour, from about 5° C./hour to about 9° C./hour, from about 5° C./hour to about 7° C./hour, or from about 7° C./hour to about 9° C./hour. In some embodiments, in recrystallization step (6), the mixture is cooled from $T^3$ to $T^4$ at a rate of from about 3° C./hour to about 11° C./hour. In some embodiments, in recrystallization step (6), the mixture is cooled from $T^3$ to $T^4$ at a rate of from about 5° C./hour to about 7° C./hour.

In certain embodiments, in recrystallization step (6), the mixture is cooled from $T^3$ to $T^4$ at a rate of about 3° C./hour, about 4° C./hour, about 5° C./hour, about 6° C./hour, about 7° C./hour, about 8° C./hour, about 9° C./hour, about 10° C./hour, or about 11° C./hour. In some embodiments, in recrystallization step (6), the mixture is cooled from $T^3$ to $T^4$ at a rate of about 5° C./hour, about 6° C./hour, or about 7° C./hour.

In certain embodiments, in recrystallization step (7), the mixture is held at $T^4$ for at least 1 hour, 1.5 hours, 2 hours, 2.5 hours, 3 hours, 3.5 hours, 4 hours, 4.5 hours, 5 hours, 5.5 hours, 6 hours, 6.5 hours, at least 7 hours, at least 7.5 hours, at least 8 hours, at least 8.5 hours, at least 9 hours, at least 9.5 hours, or at least 10 hours. In some embodiments, in recrystallization step (7), the mixture is held at $T^4$ for at least 2 hours.

In certain embodiments, in recrystallization step (7), the mixture is held at $T^4$ for no greater than 1 hour, no greater than 1.5 hours, no greater than 2 hours, no greater than 2.5 hours, no greater than 3 hours, no greater than 3.5 hours, no greater than 4 hours, no greater than 4.5 hours, no greater than 5 hours, no greater than 5.5 hours, no greater than 6 hours, no greater than 6.5 hours, no greater than 7 hours, no greater than 7.5 hours, no greater than 8 hours, no greater than 8.5 hours, no greater than 9 hours, no greater than 9.5 hours, no greater than 10 hours, no greater than 10.5 hours, no greater than 11 hours, no greater than 11.5 hours, no greater than 12 hours, no greater than 16 hours, no greater than 20 hours, or no greater than 24 hours.

In certain embodiments, in recrystallization step (8), $T^5$ is from about −10° C. to about 10° C., from about −5° C. to about 10° C., from about 0° C. to about 10° C., from about 5° C. to about 10° C., from about −10° C. to about 5° C., from about −10° C. to about 0° C., from about −10° C. to about −5° C., from about −5° C. to about 5° C., from about −5° C. to about 0° C., or from about 0° C. to about 5° C. In some embodiments, in recrystallization step (8), $T^5$ is from about −10° C. to about 10° C. In some embodiments, in recrystallization step (8), $T^5$ is from about 0° C. to about 10° C.

In certain embodiments, in recrystallization step (8), $T^5$ is about −10° C., about −5° C., about 0° C., about 5° C., or about 10° C. In some embodiments, in recrystallization step (8), $T^5$ is about 5° C.

In certain embodiments, in recrystallization step (8), the mixture is cooled from $T^4$ to $T^5$ at a rate of from about 3° C./hour to about 11° C./hour, from about 5° C./hour to about 11° C./hour, from about 7° C./hour to about 11° C./hour, from about 9° C./hour to about 11° C./hour, from about 3° C./hour to about 9° C./hour, from about 3° C./hour to about 7° C./hour, from about 3° C./hour to about 5° C./hour, from about 5° C./hour to about 9° C./hour, from about 5° C./hour to about 7° C./hour, or from about 7° C./hour to about 9° C./hour. In some embodiments, in recrystallization step (8), the mixture is cooled from $T^4$ to $T^5$ at a rate of from about 3° C./hour to about 11° C./hour. In some embodiments, in recrystallization step (8), the mixture is cooled from $T^4$ to $T^5$ at a rate of from about 5° C./hour to about 7° C./hour.

In certain embodiments, in recrystallization step (8), the mixture is cooled from $T^4$ to $T^5$ at a rate of about 3° C./hour, about 4° C./hour, about 5° C./hour, about 6° C./hour, about 7° C./hour, about 8° C./hour, about 9° C./hour, about 10° C./hour, or about 11° C./hour. In some embodiments, in recrystallization step (8), the mixture is cooled from $T^4$ to $T^5$ at a rate of about 5° C./hour, about 6° C./hour, or about 7° C./hour.

In certain embodiments, in recrystallization step (9), the mixture is held at $T^5$ for at least 1 hour, 1.5 hours, 2 hours, 2.5 hours, 3 hours, 3.5 hours, 4 hours, 4.5 hours, 5 hours, 5.5 hours, 6 hours, 6.5 hours, at least 7 hours, at least 7.5 hours, at least 8 hours, at least 8.5 hours, at least 9 hours, at least 9.5 hours, or at least 10 hours. In some embodiments, in recrystallization step (9), the mixture is held at $T^5$ for at least 4 hours.

In certain embodiments, in recrystallization step (9), the mixture is held at $T^5$ for no greater than 1 hour, no greater than 1.5 hours, no greater than 2 hours, no greater than 2.5 hours, no greater than 3 hours, no greater than 3.5 hours, no greater than 4 hours, no greater than 4.5 hours, no greater than 5 hours, no greater than 5.5 hours, no greater than 6 hours, no greater than 6.5 hours, no greater than 7 hours, no greater than 7.5 hours, no greater than 8 hours, no greater than 8.5 hours, no greater than 9 hours, no greater than 9.5 hours, no greater than 10 hours, no greater than 10.5 hours, no greater than 11 hours, no greater than 11.5 hours, no greater than 12 hours, no greater than 16 hours, no greater than 20 hours, or no greater than 24 hours.

In certain embodiments, recrystallizing the compound of formula (V) further comprises seeding the mixture with an amount of a crystalline form of the compound of formula (V) prior to recrystallization step (2), during recrystallization step (2), during recrystallization step (3), during recrystallization step (4), during recrystallization step (5), during recrystallization step (6), during recrystallization step (7), during recrystallization step (8), during recrystallization step (9), or any combination thereof, in order to facilitate the crystallization of the compound of formula (V).

It should be understood that the conditions (e.g., temperatures), times, seeding, amounts, compounds, and other parameter and/or variables for crystallizing the compound of formula (V) as described herein can be equally applicable to recrystallization of the compound of formula (V), unless otherwise stated or understood from the context, or as noted below.

For example, in certain embodiments, recrystallizing the compound of formula (V) comprises filtration of the crystalline form of the compound of formula (V). In certain embodiments, filtering the crystalline form of the compound of formula (V) occurs at a temperature of from about −20° C. to about 15° C., from about −15° C. to about 15° C., from about −10° C. to about 15° C., from about −5° C. to about 15° C., from about 0° C. to about 15° C., from about 5° C. to about 15° C., from about 10° C. to about 15° C., from about −20° C. to about 10° C., from about −20° C. to about 5° C., from about −20° C. to about 0° C., from about −20° C. to about −5° C., from about −20° C. to about −10° C., from about −20° C. to about −15° C., from about −15° C. to about 10° C., from about −15° C. to about 5° C., from about −15° C. to about 0° C., from about −15° C. to about −5° C., from about −15° C. to about −10° C., from about −10° C. to about 10° C., from about −10° C. to about 5° C., from about −10° C. to about 0° C., from about −10° C. to about −5° C., from about −5° C. to about 10° C., from about −5° C. to about 5° C., from about −5° C. to about 0° C., from about 0° C. to about 10° C., from about 0° C. to about 5° C., or from about 5° C. to about 10° C. In some embodiments, filtering of the crystalline form of the compound of formula (V) occurs at a temperature of from about 0° C. to about 15° C.

In certain embodiments, filtering of the crystalline form of the compound of formula (V) occurs at a temperature of about −20° C., about −15° C., about −10° C., about −5° C., about 0° C., about 5° C., about 10° C., or about 15° C. In some embodiments, filtering of the crystalline form of the compound of formula (V) occurs at a temperature of about 0° C., about 5° C., about 10° C., or about 15° C.

In certain embodiments, filtration further comprises washing. In certain embodiments, washing comprises washing the crystalline form of the compound of formula (V) with a solvent. In some embodiments, washing comprises washing the crystalline form of the compound of formula (V) with acetonitrile.

In certain embodiments, recrystallizing the compound of formula (V) comprises isolating the crystalline form of the compound of formula (V) from the mixture by centrifugation.

In certain embodiments, isolation of the crystalline form of the compound of formula (V) by centrifugation further comprises washing. In certain embodiments, washing comprises washing the crystalline form of the compound of formula (V) with a solvent. In some embodiments, washing comprises washing the crystalline form of the compound of formula (V) with acetonitrile.

In certain embodiments, the temperature of the solvent, for example, acetonitrile, is from about −20° C. to about 30° C., from about −10° C. to about 30° C., from about 0° C. to about 30° C., from about 10° C. to about 30° C., from about −20° C. to about 20° C., from about −20° C. to about 10° C., from about −20° C. to about 0° C., from about −20° C. to about −10° C., from about −10° C. to about 20° C., from about −10° C. to about 10° C., from about −10° C. to about 0° C., from about 0° C. to about 20° C., from about 0° C. to about 10° C., or from about 10° C. to about 20° C. In some embodiments, the temperature of the solvent is from about 10° C. to about 30° C.

In certain embodiments, the temperature of the solvent, for example, acetonitrile, is about −20° C., about −10° C., about 0° C., about 10° C., about 20° C., or about 30° C. In some embodiments, the temperature of the solvent is about 20° C.

In certain embodiments, recrystallizing the compound of formula (V) comprises drying.

In certain embodiments, drying comprises heating the crystalline form of the compound of formula (V) to a temperature of less than about 85° C., less than about 75° C., less than about 65° C., less than about 55° C., less than about 45° C., less than about 35° C., or less than about 25° C. In some embodiments, the drying step comprises heating the crystalline form of the compound of formula (V) to a temperature of less than about 85° C. In some embodiments, the drying step comprises heating the crystalline form of the compound of formula (V) to a temperature of less than about 45° C.

In certain embodiments, the one or more recrystallizations of the crystalline form of the compound of formula (V) comprises 1, 2, 3, 4, 5, 6, 7, 8, 9 or 10 recrystallizations.

In certain embodiments, the one or more recrystallizations of the crystalline form of the compound of formula (V) comprises:
(1) dissolving the crystalline compound of formula (V) in one or more solvents comprising ethyl acetate and water, thereby forming a mixture;
(2) cooling the mixture from a first temperature ($T^1$) to a second temperature ($T^2$), wherein $T^1$ is about 55° C., $T^2$ is about 30° C., and the mixture is cooled from $T^1$ to $T^2$ at a rate of from about 5° C./hour to about 7° C./hour;
(3) holding the compound of formula (V) at $T^2$ for at least 2 hours;
(4) heating the mixture from $T^2$ to a third temperature ($T^3$), wherein $T^3$ is about 40° C. and the mixture is heated from $T^2$ to $T^3$ at a rate of from about 5° C./hour to about 7° C./hour;
(5) holding the mixture at $T^3$ for at least 1 hour;
(6) cooling the mixture from $T^3$ to a fourth temperature ($T^4$), wherein $T^4$ is about 35° C. and the mixture is cooled from $T^3$ to $T^4$ at a rate of from about 5° C./hour to about 7° C./hour;
(7) holding the mixture at $T^4$ for at least 2 hours;
(8) cooling the mixture from $T^4$ to a fifth temperature ($T^5$), wherein $T^5$ is about 5° C. and the mixture is cooled from $T^4$ to $T^5$ at a rate of from about 5° C./hour to about 7° C./hour; and
(9) holding the mixture at $T^5$ for at least 4 hours, thereby producing a pharmaceutical material comprising a purified amount of crystalline form of the compound of formula (V).

It should be understood that the conditions (e.g., temperatures), times, seeding, amounts, compounds, and other parameters and/or variables for crystallizing and/or recrystallizing the compound of formula (V) as described herein can be equally applicable to the immediately above-described recrystallizing process, unless otherwise stated or understood from the context (e.g., the conditions or parameters fall outside the values or ranges in the immediately above-described recrystallizing process).

In certain embodiments, the crystalline form of the compound of formula (V) in the pharmaceutical material produced by any of the recrystallization methods described herein may be a crystalline form of the compound of formula (V) as characterized herein, for example, by an X-ray powder diffraction pattern or peak(s), and/or other characteristic properties of the crystalline form of bempedoic acid.

In various embodiments, the purified amount of the compound of formula (V) in the pharmaceutical material is greater than 99.0%, greater than about 99.1%, greater than about 99.2%, greater than about 99.3%, greater than about 99.4%, greater than about 99.5%, greater than about 99.6%, greater than about 99.7%, greater than about 99.8%, greater than about 99.85%, greater than about 999%, greater than about 9995%, or greater than about 99.98% by weight of the total weight of the pharmaceutical material. In some embodiments, the purified amount of the compound of formula (V) in the pharmaceutical material is greater than 99.0% by weight of the total weight of the pharmaceutical material. In some embodiments, the purified amount of the compound of formula (V) in the pharmaceutical material is greater than about 99.5% by weight of the total weight of the pharmaceutical material. In some embodiments, the purified amount of the compound of formula (V) in the pharmaceutical material is greater than about 99.7% by weight of the total weight of the pharmaceutical material. In some embodiments, the purified amount of the compound of formula (V) in the pharmaceutical material is greater than about 99.85% by weight of the total weight of the pharmaceutical material.

In certain embodiments, subsequent to recrystallizing the crystalline form of the compound of formula (V), which provides a recrystallized compound of formula (V), the method comprises contacting the recrystallized compound of formula (V) with charcoal, and filtering the charcoal to provide a pharmaceutical material comprising a purified amount of the compound of formula (V). In some embodiments, contacting the compound of formula (V) with charcoal comprises contacting the compound of formula (V) with a solution, wherein the solution comprises acetonitrile and activated charcoal (e.g., 5% (w/w) activated charcoal).

In certain embodiments, the methods described herein can be used to prepare a batch of bempedoic acid. In certain embodiments, the methods described herein can be used to prepare a batch of a pharmaceutical material, wherein the pharmaceutical material comprises a purified amount of the compound of formula (V). In certain embodiments, the purified amount of the compound of formula (V), or a pharmaceutically acceptable salt thereof, is greater than 99.0% by weight of the total weight of the pharmaceutical material.

In certain embodiments, the batch is in an amount of about 1 kg, 2 kg, 3 kg, 4 kg, 5 kg, 10 kg, 20 kg, 30 kg, 40 kg, 50 kg, 60 kg, 70 kg, 80 kg, 90 kg, 100 kg, 200 kg, 300 kg, 400 kg, 500 kg, 600 kg, 700 kg, 800 kg, 900 kg, or 1000 kg.

IV. High Purity Compositions of Bempedoic Acid

As described herein, in one aspect, the invention provides pharmaceutical materials comprising bempedoic acid such as a crystalline form of bempedoic acid, or a pharmaceutically acceptable salt thereof.

In various embodiments, a pharmaceutical material generally comprises a crystalline form of the compound of formula (V):

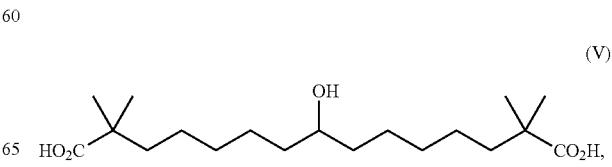

or a pharmaceutically acceptable salt thereof, wherein the pharmaceutical material comprises the compound of formula (V), or a pharmaceutically acceptable salt thereof, in an amount greater than 99.0% by weight based on the total weight of the pharmaceutical material. In some embodiments, the amount of the compound of formula (V) in the pharmaceutical material is greater than about 99.1%, greater than about 99.2%, greater than about 99.3%, greater than about 99.4%, greater than about 99.5%, greater than about 99.6%, greater than about 99.7%, greater than about 99.8%, greater than about 99.85%, greater than about 99.9%, greater than about 99.95%, or greater than about 99.98% by weight of the total weight of the pharmaceutical material. In some embodiments, the pharmaceutical material comprises the compound of formula (V) in an amount greater than 99.5% by weight based on the total weight of the pharmaceutical material. In some embodiments, the pharmaceutical material comprises the compound of formula (V) in an amount greater than 99.7% by weight based on the total weight of the pharmaceutical material. In some embodiments, the pharmaceutical material comprises the compound of formula (V) in an amount greater than 99.9% by weight based on the total weight of the pharmaceutical material.

In certain embodiments, the pharmaceutical material comprises the compound of formula (V) in an amount of from about 98% to about 102% by weight based on the total weight of the pharmaceutical material (anhydrous, solvent-free basis), as determined by a high performance liquid chromatography (HPLC) assay.

In certain embodiments, the HPLC assay comprises one or more of:
(i) a Waters XBridge BEH C18 column (4.6 mm i.d.×150 mm, 2.5 µm);
(ii) a column temperature of about 40° C.;
(iii) a mobile phase comprising about 0.05% phosphoric acid in water/acetonitrile (about 50:50);
(iv) isocratic elution;
(v) a flow rate of about 1.2 mL/minute;
(vi) a sample temperature of ambient temperature;
(vii) detection at 215 nm; and
(viii) the retention time of the compound of formula (V) is about 4.6 minutes.

In some embodiments, the HPLC assay comprises each of the above, i.e., (i)-(viii).

In certain embodiments, the crystalline form of the compound of formula (V) may be a crystalline form of the compound of formula (V) as characterized herein, for example, by an X-ray powder diffraction pattern or peak(s), and/or other characteristic properties of the crystalline form of bempedoic acid.

In certain embodiments, a pharmaceutical material described herein can comprise a compound of formula (VI):

0.0001% by weight based on the total weight of the pharmaceutical material. In some embodiments, the amount of the diol impurity in the pharmaceutical material is less than about 1.25% by weight based on the total weight of the pharmaceutical material. In some embodiments, the amount of the diol impurity in the pharmaceutical material is less than about 0.15% by weight based on the total weight of the pharmaceutical material. In some embodiments, the amount of the diol impurity in the pharmaceutical material is less than about 0.1% by weight based on the total weight of the pharmaceutical material.

In certain embodiments, the pharmaceutical material comprises the compound of formula (VI), or a pharmaceutically acceptable salt thereof, in an amount no greater than about 0.15%, about 0.125%, about 0.1%, about 0.075%, about 0.05%, about 0.025%, about 0.01%, about 0.001%, or about 0.0001% by weight based on the total weight of the pharmaceutical material. In some embodiments, the pharmaceutical material comprises the compound of formula (VI), or a pharmaceutically acceptable salt thereof, in an amount no greater than about 0.125% by weight based on the total weight of the pharmaceutical material. In some embodiments, the pharmaceutical material comprises the compound of formula (VI), or a pharmaceutically acceptable salt thereof, in an amount no greater than about 0.15% by weight based on the total weight of the pharmaceutical material. In some embodiments, the pharmaceutical material comprises the compound of formula (VI), or a pharmaceutically acceptable salt thereof, in an amount no greater than about 0.1% by weight based on the total weight of the pharmaceutical material.

In certain embodiments, the amount of the diol impurity in the pharmaceutical material is from about 0.0001% to about 0.15%, from about 0.001% to about 0.15%, from about 0.01% to about 0.15%, from about 0.025% to about 0.15%, from about 0.05% to about 0.15%, from about 0.075% to about 0.15%, from about 0.1% to about 0.15%, from about 0.125% to about 0.15%, from about 0.01% to about 0.125%, from about 0.01% to about 0.1%, from about 0.01% to about 0.075%, from about 0.01% to about 0.05%, from about 0.01% to about 0.25%, from about 0.025% to about 0.125%, from about 0.025% to about 0.1%, from about 0.025% to about 0.075%, from about 0.025% to about 0.05%, from about 0.05% to about 0.125%, from about 0.05% to about 0.1%, from about 0.05% to about 0.075%, from about 0.075% to about 0.125%, from about 0.075% to about 0.1%, or from about 0.1% to about 0.125% by weight based on the total weight of the pharmaceutical material. In some embodiments, the amount of the diol impurity in the pharmaceutical material is from about 0.01% to about 0.15% by weight based on the total weight of the pharmaceutical

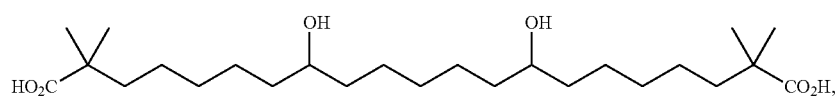

(VI)

or a pharmaceutically acceptable salt thereof. The compound of formula (VI), or a pharmaceutically acceptable salt thereof, is also referred to herein as the "diol impurity."

In certain embodiments, the amount of the diol impurity in the pharmaceutical material is less than about 0.15%, about 0.125%, about 0.1%, about 0.075%, about 0.05%, about 0.025%, about 0.01%, about 0.001%, or about material. In some embodiments, the amount of the diol impurity in the pharmaceutical material is from about 0.01% to about 0.1% by weight based on the total weight of the pharmaceutical material.

In certain embodiments, a pharmaceutical material described herein can comprise the compound of formula (VII):

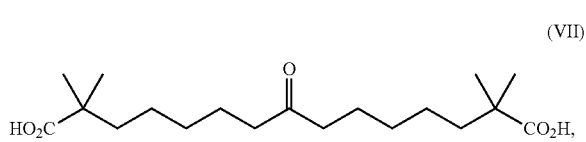 [SMILES: CC(C)(CCCCCC(=O)CCCCCC(C)(C)C(=O)O)C(=O)O]

(VII)

or a pharmaceutically acceptable salt thereof. The compound of formula (VII), or a pharmaceutically acceptable salt thereof, is also referred to herein as the "ketone impurity."

In certain embodiments, the amount of the ketone impurity in the pharmaceutical material is less than about 0.15%, about 0.125%, about 0.1%, about 0.075%, about 0.05%, about 0.025%, about 0.01%, about 0.001%, or about 0.0001% by weight based on the total weight of the pharmaceutical material. In certain embodiments, the amount of the ketone impurity in the pharmaceutical material is less than about 0.15% by weight based on the total weight of the pharmaceutical material. In certain embodiments, the amount of the ketone impurity in the pharmaceutical material is less than about 0.05% by weight based on the total weight of the pharmaceutical material.

In certain embodiments, the pharmaceutical material comprises the compound of formula (VII), or a pharmaceutically acceptable salt thereof, in an amount no greater than about 0.15%, about 0.125%, about 0.1%, about 0.075%, about 0.05%, about 0.025%, about 0.01%, about 0.001%, or about 0.0001% by weight based on the total weight of the pharmaceutical material. In some embodiments, the pharmaceutical material comprises the compound of formula (VII), or a pharmaceutically acceptable salt thereof, in an amount no greater than about 0.15% by weight based on the total weight of the pharmaceutical material. In some embodiments, the pharmaceutical material comprises the compound of formula (VII), or a pharmaceutically acceptable salt thereof, in an amount no greater than about 0.05% by weight based on the total weight of the pharmaceutical material.

In certain embodiments, the amount of the ketone impurity in the pharmaceutical material is from about 0.0001% to about 0.15%, from about 0.001% to about 0.15%, from about 0.01% to about 0.15%, from about 0.025% to about 0.15%, from about 0.05% to about 0.15%, from about 0.075% to about 0.15%, from about 0.1% to about 0.15%, from about 0.125% to about 0.15%, from about 0.01% to about 0.125%, from about 0.01% to about 0.1%, from about 0.01% to about 0.075%, from about 0.01% to about 0.05%, from about 0.01% to about 0.025%, from about 0.025% to about 0.125%, from about 0.025% to about 0.1%, from about 0.025% to about 0.075%, from about 0.025% to about 0.05%, from about 0.05% to about 0.125%, from about 0.05% to about 0.1%, from about 0.05% to about 0.075%, from about 0.075% to about 0.125%, from about 0.075% to about 0.1%, or from about 0.1% to about 0.125% by weight based on the total weight of the pharmaceutical material. In some embodiments, the amount of the ketone impurity in the pharmaceutical material is from about 0.01% to about 0.15% by weight based on the total weight of the pharmaceutical material. In some embodiments, the amount of the ketone impurity in the pharmaceutical material is from about 0.01% to about 0.05% by weight based on the total weight of the pharmaceutical material.

In certain embodiments, a pharmaceutical material described herein can comprise the compound of formula (VIII):

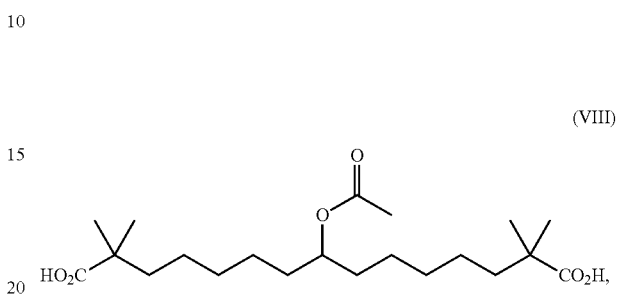

(VIII)

or a pharmaceutically acceptable salt thereof. The compound of formula (VIII), or a pharmaceutically acceptable salt thereof, is also referred to herein as the "acetate impurity."

In certain embodiments, the amount of the acetate impurity in the pharmaceutical material is less than about 0.15%, about 0.125%, about 0.1%, about 0.075%, about 0.05%, about 0.025%, about 0.01%, about 0.001% or about 0.0001% by weight based on the total weight of the pharmaceutical material.

In certain embodiments, the pharmaceutical material comprises the compound of formula (VIII), or a pharmaceutically acceptable salt thereof, in an amount no greater than about 0.15%, about 0.125%, about 0.1%, about 0.075%, about 0.05%, about 0.025%, about 0.01%, about 0.001%, or about 0.0001% by weight based on the total weight of the pharmaceutical material.

In certain embodiments, the amount of the acetate impurity in the pharmaceutical material is from about 0.0001% to about 0.15%, from about 0.001% to about 0.15%, from about 0.01% to about 0.15%, from about 0.025% to about 0.15%, from about 0.05% to about 0.15%, from about 0.075% to about 0.15%, from about 0.1% to about 0.15%, from about 0.125% to about 0.15%, from about 0.01% to about 0.125%, from about 0.01% to about 0.1%, from about 0.01% to about 0.075%, from about 0.01% to about 0.05%, from about 0.01% to about 0.025%, from about 0.025% to about 0.125%, from about 0.025% to about 0.1%, from about 0.025% to about 0.075%, from about 0.025% to about 0.05%, from about 0.05% to about 0.125%, from about 0.05% to about 0.1%, from about 0.05% to about 0.075%, from about 0.075% to about 0.125%, from about 0.075% to about 0.1%, or from about 0.1% to about 0.125% by weight based on the total weight of the pharmaceutical material.

In certain embodiments, a pharmaceutical material described herein can comprise the compound of formula (IX):

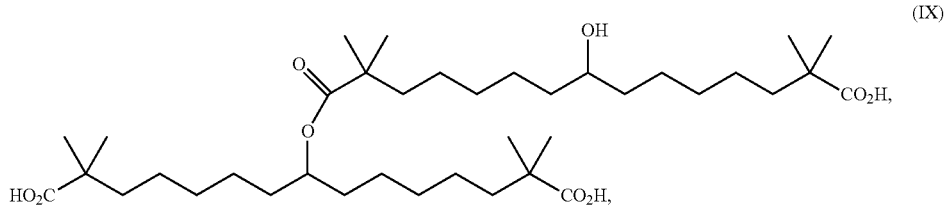 [SMILES: CC(C)(CCCCCC(O)CCCCCC(C)(C)C(=O)OC(CCCCCC(C)(C)C(=O)O)CCCCCC(C)(C)C(=O)O)C(=O)O]

or a pharmaceutically acceptable salt thereof. The compound of formula (IX), or a pharmaceutically acceptable salt thereof, is also referred to herein as the "dimer impurity."

In certain embodiments, the amount of the dimer impurity in the pharmaceutical material is less than about 0.15%, about 0.125%, about 0.1%, about 0.075%, about 0.05%, about 0.025%, about 0.010%, about 0.0010% or about 0.0001% by weight based on the total weight of the pharmaceutical material.

In certain embodiments, the pharmaceutical material comprises the compound of formula (IX), or a pharmaceutically acceptable salt thereof, in an amount no greater than about 0.15%, about 0.125%, about 0.1%, about 0.075%, about 0.05%, about 0.025%, about 0.01%, about 0.001%, or about 0.0001% by weight based on the total weight of the pharmaceutical material.

In certain embodiments, the amount of the dimer impurity in the pharmaceutical material is from about 0.0001% to about 0.15%, from about 0.0005% to about 0.15%, from about 0.01% to about 0.15%, from about 0.025% to about 0.15%, from about 0.05% to about 0.15%, from about 0.075% to about 0.15%, from about 0.1% to about 0.15%, from about 0.125% to about 0.15%, from about 0.01% to about 0.125%, from about 0.01% to about 0.1%, from about 0.01% to about 0.075%, from about 0.01% to about 0.05%, from about 0.01% to about 0.025%, from about 0.025% to about 0.125%, from about 0.025% to about 0.1%, from about 0.025% to about 0.075%, from about 0.025% to about 0.05%, from about 0.05% to about 0.125%, from about 0.05% to about 0.1%, from about 0.05% to about 0.075%, from about 0.075% to about 0.125%, from about 0.075% to about 0.1%, or from about 0.1% to about 0.125% by weight based on the total weight of the pharmaceutical material.

In certain embodiments, a pharmaceutical material described herein can comprise the compound of formula (X):

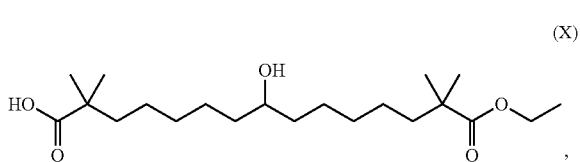 [SMILES: CCOC(=O)C(C)(C)CCCCCC(O)CCCCCC(C)(C)C(=O)O]

or a pharmaceutically acceptable salt thereof. The compound of formula (X), or a pharmaceutically acceptable salt thereof, is also referred to herein as the "monoethyl ester impurity."

In certain embodiments, the amount of the monoethyl ester impurity in the pharmaceutical material is less than about 0.15%, about 0.125%, about 0.1%, about 0.075%, about 0.05%, about 0.025%, about 0.01%, about 0.001% or about 0.0001% by weight based on the total weight of the pharmaceutical material.

In certain embodiments, the pharmaceutical material comprises the compound of formula (X), or a pharmaceutically acceptable salt thereof, in an amount no greater than about 0.15%, about 0.125%, about 0.1%, about 0.075%, about 0.05%, about 0.025%, about 0.01%, about 0.001%, or about 0.0001% by weight based on the total weight of the pharmaceutical material.

In certain embodiments, the amount of the monoethyl ester impurity in the pharmaceutical material is from about 0.0001% to about 0.15%, from about 0.0005% to about 0.15%, from about 0.01% to about 0.15%, from about 0.025% to about 0.15%, from about 0.05% to about 0.15%, from about 0.075% to about 0.15%, from about 0.1% to about 0.15%, from about 0.125% to about 0.15%, from about 0.01% to about 0.125%, from about 0.01% to about 0.1%, from about 0.01% to about 0.075%, from about 0.01% to about 0.05%, from about 0.01% to about 0.025%, from about 0.025% to about 0.125%, from about 0.025% to about 0.1%, from about 0.025% to about 0.075%, from about 0.025% to about 0.05%, from about 0.05% to about 0.125%, from about 0.05% to about 0.1%, from about 0.05% to about 0.075%, from about 0.075% to about 0.125%, from about 0.075% to about 0.1%, or from about 0.1% to about 0.125% by weight based on the total weight of the pharmaceutical material.

In certain embodiments, a pharmaceutical material described herein can comprise the compound of formula (XI):

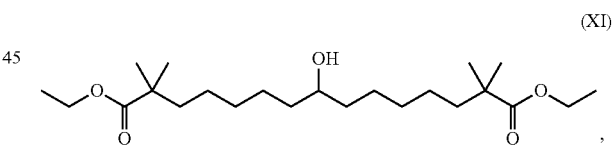

or a pharmaceutically acceptable salt thereof. The compound of formula (XI), or a pharmaceutically acceptable salt thereof, is also referred to herein as the "diethyl ester impurity."

In certain embodiments, the amount of the diethyl ester impurity in the pharmaceutical material is less than about 0.15%, about 0.125%, about 0.1%, about 0.075%, about 0.05%, about 0.025%, about 0.01%, about 0.001% or about 0.0001% by weight based on the total weight of the pharmaceutical material.

In certain embodiments, the pharmaceutical material comprises the compound of formula (XI), or a pharmaceutically acceptable salt thereof, in an amount no greater than about 0.15%, about 0.125%, about 0.1%, about 0.075%, about 0.05%, about 0.025%, about 0.01%, about 0.001%, or about 0.0001% by weight based on the total weight of the pharmaceutical material.

In certain embodiments, the amount of the diethyl ester impurity in the pharmaceutical material is from about 0.0001% to about 0.15%, from about 0.0005% to about 0.15%, from about 0.01% to about 0.15%, from about 0.025% to about 0.15%, from about 0.05% to about 0.15%, from about 0.075% to about 0.15%, from about 0.10% to about 0.15%, from about 0.125% to about 0.15%, from about 0.01% to about 0.125%, from about 0.01% to about 0.1%, from about 0.01% to about 0.075%, from about 0.01% to about 0.05%, from about 0.01% to about 0.025%, from about 0.025% to about 0.125%, from about 0.025% to about 0.1%, from about 0.025% to about 0.075%, from about 0.025% to about 0.05%, from about 0.05% to about 0.125%, from about 0.05% to about 0.1%, from about 0.05% to about 0.075%, from about 0.075% to about 0.125%, from about 0.075% to about 0.1%, or from about 0.1% to about 0.125% by weight based on the total weight of the pharmaceutical material.

In certain embodiments, a pharmaceutical material described herein can comprise an impurity with a relative retention time (RRT) of about 1.04 to about 1.05, as determined by HPLC. In certain embodiments, a pharmaceutical material described herein can comprise an impurity with a relative retention time (RRT) of about 1.06 to about 1.08, as determined by HPLC. In certain embodiments, a pharmaceutical material described herein can comprise an impurity with a relative retention time (RRT) of about 1.18 to about 1.20, as determined by HPLC. In certain embodiments, a pharmaceutical material described herein can comprise an impurity with a relative retention time (RRT) of about 1.36, as determined by HPLC. In certain embodiments, a pharmaceutical material described herein can comprise an impurity with a RRT of about 1.43, as determined by HPLC. In certain embodiments, a pharmaceutical material described herein can comprise an impurity with a RRT of about 1.86, as determined by HPLC. In certain embodiments, a pharmaceutical material described herein can comprise a first impurity with a RRT of about 1.36 and a second impurity with a RRT of about 1.86, as determined by HPLC. In certain embodiments, the RRT of the impurity is based on the retention time of bempedoic acid, wherein the RRT of bempedoic acid is about 1.00.

In certain embodiments, a pharmaceutical material described herein can comprise one or more unidentified impurities (e.g., impurities in the pharmaceutical material whose chemical structure cannot be determined but whose RRT is known).

In certain embodiments, the pharmaceutical material comprises one or more of the impurities described herein, as determined by a high performance liquid chromatography (HPLC) assay.

In certain embodiments, the HPLC assay comprises one or more of:
 (i) a Waters XBridge BEH C18 column (4.6 mm i.d.×150 mm, 2.5 µm);
 (ii) a column temperature of about 40° C.;
 (iii) a first mobile phase comprising about 0.05% formic acid in water;
 (iv) a second mobile phase comprising about 0.05% formic acid in acetonitrile;
 (v) a flow rate of about 1.2 mL/minute;
 (vi) a sample temperature of ambient temperature; and
 (vii) the retention time of the compound of formula (V) is about 15.2 minutes.

In some embodiments, the HPLC assay comprises each of the above, i.e., (i)-(vii).

In certain embodiments, the amount of the one or more unidentified impurities in the pharmaceutical material is less than about 0.010%, about 0.02%, about 0.03%, about 0.04%, about 0.05%, about 0.06%, about 0.07%, about 0.08%, about 0.09%, or about 0.1% by weight based on the total weight of the pharmaceutical material. In some embodiments, the amount of the one or more unidentified impurities in the pharmaceutical material is less than about 0.05% by weight based on the total weight of the pharmaceutical material.

In certain embodiments, the amount of the one or more unidentified impurities in the pharmaceutical material is from about 0.0001% to about 0.1%, from about 0.0005% to about 0.1%, from about 0.001% to about 0.1%, from about 0.005% to about 0.1%, from about 0.01% to about 0.1%, from about 0.05% to about 0.1%, from about 0.0001% to about 0.05%, from about 0.0001% to about 0.01%, from about 0.0001% to about 0.005%, from about 0.0001% to about 0.001%, from about 0.0001% to about 0.0005%, from about 0.0005% to about 0.05%, from about 0.0005% to about 0.010%, from about 0.0005% to about 0.005%, from about 0.0005% to about 0.001%, from about 0.001% to about 0.05%, from about 0.001% to about 0.01%, from about 0.001% to about 0.005%, from about 0.005% to about 0.05%, from about 0.005% to about 0.01%, or from about 0.01% to about 0.05% by weight based on the total weight of the pharmaceutical material. In certain embodiments, the amount of the one or more unidentified impurities in the pharmaceutical material is from about 0.0001% to about 0.1% by weight based on the total weight of the pharmaceutical material. In certain embodiments, the amount of the one or more unidentified impurities in the pharmaceutical material is from about 0.05% to about 0.1% by weight based on the total weight of the pharmaceutical material.

V. Pharmaceutical Compositions

In another aspect, provided herein are pharmaceutical compositions comprising bempedoic acid, or a pharmaceutically acceptable salt thereof, as described and/or made herein, including any of the pharmaceutical materials as well as the impurities. In various embodiments, a pharmaceutical composition generally comprises a pharmaceutical material as described herein; and a pharmaceutically acceptable excipient. For example, the pharmaceutical material can comprise greater than 99.0% of the compound of formula (V), or a pharmaceutically acceptable salt thereof.

In certain embodiments, the pharmaceutical compositions may be specially formulated for administration as solid or liquid dosage forms. In some embodiments, the pharmaceutical compositions described herein are formulated for administration as an oral dosage form. Examples of oral dosage forms include, but are not limited to a drench, a tablet, a capsule, a cachet, a pill, an emulsion, a lozenge, a solution, a suspension, a bolus, a powder, an elixir or syrup, a pastille, a mouthwash, a granule, or a paste for application to the tongue. In some embodiments, the pharmaceutical compositions described herein are formulated as a dosage form suitable for parenteral administration. In some embodiments, the pharmaceutical compositions described herein are administered by subcutaneous, intramuscular, intravenous or epidural injection. Examples of dosage forms suitable for parenteral administration include, but are not limited to, a sterile solution or suspension, or a sustained-release formulation. In some embodiments, the pharmaceutical compositions described herein are formulated as a dosage form suitable for topical application.

Examples of dosage forms suitable for topical administration include, but are not limited to, a powder, a spray, an ointment, a paste, a cream, a lotion, a gel, a solution, a patch, an inhalant, or a controlled-release patch or spray applied to the skin. In some embodiments, the pharmaceutical compositions described herein are formulated as a dosage form suitable for intravaginal or intrarectal administration. Examples of dosage forms suitable for intravaginal or intrarectal administration include, but are not limited to, a pessary, a cream, or a foam. In some embodiments, the pharmaceutical compositions described herein are formulated as a dosage form suitable for sublingual, ocular, transdermal or nasal administration.

In certain embodiments, the solid dosage forms described herein to be used for oral administration are prepared by mixing a pharmaceutical material with one or more pharmaceutically acceptable excipients. Pharmaceutical excipients can be selected from the group consisting of a filler or extender, a sweetening agent, a binder, a humectant, a disintegrating agent, a preservative, a perfuming agent, a flavoring agent, an antioxidant, a solution retarding agent, an absorption accelerator, a wetting agent, an absorbent, a lubricant, a coloring agent, and a controlled release agent. In some embodiments, when the solid dosage form is a capsule, a tablet or a pill, the pharmaceutical compositions described herein may also comprise a buffering agent. In some embodiments, when the solid dosage form is a gelatin capsule, the pharmaceutical composition may further comprise one or more excipients selected from lactose, a milk sugar, a high molecular weight polyethylene glycol and combinations thereof.

In certain embodiments, a pharmaceutical composition of the invention may comprise one or more excipients selected from the group consisting of a cyclodextrin, a cellulose, a liposome, a micelle forming agent, and a polymeric carrier. In some embodiments, the pharmaceutical compositions of the present invention comprise an antibacterial agent, an antifungal agent, or combinations thereof. Examples antibacterial and antifungal agents include, but are not limited to, paraben, chlorobutanol, phenol and sorbic acid. In some embodiments, the pharmaceutical compositions of the present invention comprise an isotonic agent In certain embodiments, the dosage forms of the present invention may be formulated so as to provide slow or controlled release of the compound of formula (V), or a pharmaceutically acceptable salt thereof. See, e.g., PCT/US2019/018356, which discloses sustained release formulations of bempedoic acid. In some embodiments, the dosage forms of the present invention may be formulated for rapid release.

In certain embodiments, a liquid dosage form of a pharmaceutical composition of the invention comprises one or more of the following; an inert diluent, a solubilizing agent and an emulsifier.

In certain embodiments, oral suspensions of a pharmaceutical composition of the invention comprise one or more suspending agents including an ethoxylated isostearyl alcohol, a polyoxyethylene sorbitol and sorbitan ester, a microcrystalline cellulose, an aluminum metahydroxide, bentonite, agar-agar and tragacanth, and mixtures thereof.

In some embodiments, the ointments, pastes, creams and gels of a pharmaceutical composition of the invention comprise one or more excipients, wherein the one or more excipients can comprise an animal fat, a vegetable fat, an oil, a wax, a paraffin, a starch, a tragacanth, a cellulose derivative, a polyethylene glycol, a silicone, a bentonite, silicic acid, talc, zinc oxide, or mixtures thereof.

In certain embodiments, powders and sprays of a pharmaceutical composition of the invention comprise one or more excipients, wherein the one or more excipients can comprise lactose, talc, silicic acid, aluminum hydroxide, a calcium silicate, a polyamide powder, or mixtures thereof. In some embodiments, a spray of the present invention can comprise a customary propellant, wherein the customary propellant comprises one or more of a chlorofluorohydrocarbon and a volatile unsubstituted hydrocarbon.

In certain embodiments, a transdermal patch of a pharmaceutical composition of the invention provides controlled delivery of the compound of formula (V), or a pharmaceutically acceptable salt thereof, to the body. In some embodiments, ophthalmic formulations, eye ointments, powders, solutions and the like, are also included within the scope of the present invention.

In certain embodiments, the pharmaceutical compositions described herein may be administered in a unit dosage form and may be prepared by any method well known in the art of pharmacy. The amount of the compound of formula (V), or a pharmaceutically acceptable salt thereof, present in a single dosage form may vary depending upon the patient being treated and/or the particular mode of administration.

In certain embodiments, the amount of the compound of formula (V), or a pharmaceutically acceptable salt thereof, that can be combined with a pharmaceutically acceptable carrier to produce a single dosage form will generally be an amount of the compound of formula (V), or a pharmaceutically acceptable salt thereof, that produces a therapeutic effect.

In various embodiments, bempedoic acid, or a pharmaceutically acceptable salt thereof, or a pharmaceutical material of the present invention, can be prepared as a fixed dose formulation (see, e.g., U.S. Patent Application Publication No. 2018/0338922 and International Application No. WO 2018/218147).

VI. Methods of Treatment and Administration

In various embodiments, bempedoic acid, or a pharmaceutically acceptable salt thereof, as described and/or made herein, including a pharmaceutical material and/or a pharmaceutical composition, may be used for the treatment or prevention of a variety of diseases and disorders. The methods of treating a disease or disorder generally comprise administering to a patient, in need thereof, a therapeutically effective amount of a pharmaceutical material comprising a purified amount of the compound of formula (V), or a pharmaceutically acceptable salt thereof, to treat the disease or disorder.

Examples of diseases and disorders include, but are not limited to, cardiovascular disease, atrial fibrillation, blood clotting, coronary heart disease, hypercoagulable states, ischemia, myocardial infarction, myopathy, myositis, pulmonary embolism, stroke, peripheral vascular disease, dyslipidemia, dyslipoproteinemia, a disorder of glucose metabolism, Alzheimer's disease, Parkinson's disease, diabetic nephropathy, diabetic retinopathy, insulin resistance, metabolic syndrome disorders (e.g., Syndrome X), galactosemia, HIV infection, a peroxisome proliferator activated receptor-associated disorder, septicemia, a thrombotic disorder, obesity, pancreatitis, hypertension, renal disease, cancer, inflammation (e.g., liver inflammation), inflammatory muscle diseases (e.g., polymyalgia rheumatica, polymyositis, and fibrositis), impotence, gastrointestinal disease, irritable bowel syndrome, inflammatory bowel disease, inflammatory disorders (e.g., asthma, vasculitis, ulcerative colitis, Crohn's disease, Kawasaki disease, Wegener's granulomatosis, (RA), systemic lupus erythematosus (SLE), multiple sclerosis (MS), and autoimmune chronic hepatitis), arthritis (e.g., rheumatoid arthritis, juvenile rheumatoid arthritis, and osteoarthritis), osteoporosis, soft tissue rheumatism (e.g., tendonitis), bursitis, autoimmune disease (e.g., systemic lupus and erythematosus), scleroderma, ankylosing spondylitis, gout, pseudogout, non-insulin dependent diabetes mellitus, diabetes (e.g., type 2), polycystic ovarian disease, hyperlipidemias (e.g., primary hyperlipidemia, familial hypercholesterolemia (FH), Hypercholesterolemia Frederickson Type IIa, Hypercholesterolemia Frederickson Type Jib, familial combined hyperlipidemia (FCH)), lipoprotein lipase deficiencies (e.g., hypertriglyceridemia, hypoalphalipoproteinemia, and hypercholesterolemia), lipoprotein abnormalities associated with diabetes, lipoprotein abnormalities associated with obesity, and lipoprotein abnormalities associated with Alzheimer's disease. In particular embodiments, the methods include treating and/or preventing hyperlipidemia such as primary hyperlipidemia. In some embodiments, the methods include treating and/or preventing cardiovascular disease.

In certain embodiments, bempedoic acid, or a pharmaceutically acceptable salt thereof, as described and/or made herein, including a pharmaceutical material and/or a pharmaceutical composition, may be used for the treatment or prevention of one or more of high levels of low density lipoprotein cholesterol (LDL-C), high levels of apolipoprotein B (apoB), high levels of lipoprotein(a) (Lp(a)), high levels of very low density lipoprotein (VLDL), high levels of non-high density lipid cholesterol (non-HDL-C), high levels of total serum cholesterol (TC), high levels of high sensitivity c-reactive protein (hsCRP), high levels of fibrinogen, high levels of insulin, high levels of glucose, and low levels of high density lipoprotein cholesterol (HDL-C). In other words, methods of the invention can include lowering LDL-C, lowering apoB, lowering Lp(a), lowering VLDL, lowering non-HDL-C, lowering TC, and/or lowering hsCRP. Methods of the invention can include inhibiting adenosine triphosphate citrate lyase (ACL), inhibiting cholesterol synthesis, and/or suppressing fatty acid biosynthesis. In some embodiments, a purified amount of the compound of formula (V), or a pharmaceutically acceptable salt thereof, a pharmaceutical composition or a pharmaceutical material of the present invention may be used as an adjunct to diet and maximally tolerated statin therapy to lower LDL-C in adults with heterozygous familial hypercholesterolemia or established atherosclerotic cardiovascular disease. In some embodiments, a purified amount of the compound of formula (V), or a pharmaceutically acceptable salt thereof, a pharmaceutical composition or a pharmaceutical material of the present invention may be used for the treatment of non-insulin dependent diabetes mellitus without increasing weight gain.

In certain embodiments, bempedoic acid, or a pharmaceutically acceptable salt thereof, as described and/or made herein, including a pharmaceutical material and/or a pharmaceutical composition, may be used for the treatment or prevention of a variety of diseases and conditions, which include, but are not limited to aging, Alzheimer's disease, cancer, cardiovascular disease, diabetic nephropathy, diabetic retinopathy, a disorder of glucose metabolism, dyslipidemia, dyslipoproteinemia, enhancing bile production, hypertension, impotence, inflammation, insulin resistance, lipid elimination in bile, modulating C reactive protein, obesity, oxysterol elimination in bile, pancreatitis, pancreatitis, Parkinson's disease, a peroxisome proliferator activated receptor-associated disorder, phospholipid elimination in bile, renal disease, rhabdomyolysis, septicemia, sleep apnea, Syndrome X, and a thrombotic disorder.

In certain embodiments, provided herein is a method of treating a liver disorder selected from the group consisting of steatohepatitis, alcoholic liver disease, fatty liver, liver steatosis, liver cirrhosis, liver fibrosis, and acute fatty liver of pregnancy. In some embodiments, the disorder is steatohepatitis. In some embodiments, the steatohepatitis is non-alcoholic steatohepatitis. In some embodiments, the steatohepatitis is nonalcoholic fatty liver disease. In some embodiments, the disorder is alcoholic liver disease. In some embodiments, the disorder is fatty liver. In some embodiments, the disorder is liver steatosis, liver cirrhosis, or liver fibrosis. In some embodiments, the disorder is acute fatty liver of pregnancy. In some embodiments, the patient is an adult human.

In certain embodiments, the present invention provides a method for treating or preventing aging, Alzheimer's disease, cancer, cardiovascular disease, diabetic nephropathy, diabetic retinopathy, a disorder of glucose metabolism, dyslipidemia, dyslipoproteinemia, enhancing bile production, enhancing reverse lipid transport, hypertension, impotence, inflammation, insulin resistance, lipid elimination in bile, modulating C reactive protein, obesity, oxysterol elimination in bile, pancreatitis, pancreatitis, Parkinson's disease, a peroxisome proliferator activated receptor-associated disorder, phospholipid elimination in bile, renal disease, septicemia, metabolic syndrome disorders (e.g., Syndrome X), or a thrombotic disorder.

In certain embodiments, the disorder is selected from the group consisting of lipodystrophy, lysosomal acid lipase deficiency, and a glycogen storage disease. In some embodiments, the patient is an adult human.

In certain embodiments, the disorder is selected from the group consisting of hepatitis C, an infection by human immunodeficiency virus, an alpha 1-antitrypsin deficiency, Bassen-Kornzweig syndrome, hypobetalipoproteinemia, Celiac disease, Wilson's disease, and Weber-Christian syndrome. In some embodiments, the disorder is hepatitis B. In some embodiments, the disorder is hepatitis C. In some embodiments, the disorder is an infection by human immunodeficiency virus. In some embodiments, the disorder is an alpha 1-antitrypsin deficiency. In some embodiments, the disorder is Bassen-Kornzweig syndrome. In some embodiments, the disorder is hypobetalipoproteinemia. In some embodiments, the disorder is Celiac disease or Wilson's disease. In some embodiments, the disorder is Weber-Christian syndrome. In some embodiments, the patient is an adult human.

In certain embodiments, the condition is selected from the group consisting of toxic liver injury, total parenteral nutrition, severe surgical weight loss, environmental toxicity, malnutrition, and starvation. In some embodiments, the condition is toxic liver injury. In some embodiments, the condition is total parenteral nutrition or severe surgical weight loss. In some embodiments, the condition is environmental toxicity. In some embodiments, the condition is malnutrition or starvation. In some embodiments, the patient is an adult human.

In certain embodiments, in order to prolong the effect of a drug, the compound of formula (V), or a pharmaceutically acceptable salt thereof, is administered by subcutaneous or intramuscular injection, or by dissolving or suspending the drug in an oil vehicle.

In certain embodiments, the actual dosage level of the compound of formula (V), or a pharmaceutically acceptable salt thereof, in the pharmaceutical compositions of the present invention may be varied so as to obtain an amount of the compound of formula (V), or a pharmaceutically acceptable salt thereof, which is effective to achieve the desired therapeutic response for a particular patient, composition, and mode of administration, without being toxic to the patient.

In certain embodiments, the selected dosage level is dependent upon a variety of factors including the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts. In certain embodiments, a physician or veterinarian having ordinary skill in the art can readily determine and prescribe the effective amount of the pharmaceutical composition as required.

In certain embodiments, a suitable daily dose of the compound of formula (V) or a pharmaceutically acceptable salt thereof, will be an amount that corresponds to the lowest dose effective to produce a therapeutic effect. In certain embodiments, the compound of formula (V), or a pharmaceutically acceptable salt thereof, is administered at about 0.01 mg/kg to about 200 mg/kg. In certain embodiments, when compound of formula (V), or a pharmaceutically acceptable salt thereof, is co-administered with another therapeutic agent, the effective amount may be less than when the compound of formula (V), or a pharmaceutically acceptable salt thereof, is used in isolation.

In certain embodiments, the effective daily dose of the compound of formula (V), or a pharmaceutically acceptable salt thereof, may be administered as two, three, four, five, six or more sub-doses. In certain embodiments, the two, three, four, five, six or more sub-doses are administered separately at appropriate intervals throughout the day, optionally, in unit dosage forms. In some embodiments, dosing is one administration per day. In some embodiments, the compound of formula (V), or a pharmaceutically acceptable salt thereof, is administered to a patient for 1 day, 5 days, 10 days, 20 days, 30 days, 1 week, 2 weeks, 3 weeks, 3 weeks, 1 month, 2 months, 3 months, 4 months, 5 months, 6 months, 7 months, 8 months, 9 months, 10 months, 11 months, 12 months, 1 year, 2 years, 3 years, 4 years, or 5 years. In some embodiments, the compound of formula (V), or a pharmaceutically acceptable salt thereof, is administered to a patient for the duration of the patient's life span.

VII. Combination Therapy

In various embodiments, bempedoic acid, or a pharmaceutically acceptable salt thereof, as described and/or made herein, including pharmaceutical materials and pharmaceutical compositions of the present invention, can be part of a combination therapy. In certain embodiments, the combination therapy comprises the compound of formula (V), or a pharmaceutically acceptable salt thereof; and a second therapeutic agent. In certain embodiments, the combination therapy comprises a pharmaceutical material comprising a purified amount of the compound of formula (V), or a pharmaceutically acceptable salt thereof; and a second therapeutic agent.

In some embodiments, the second therapeutic agent is selected from the group comprising a lovastatin, a thiazolidinedione or fibrate, a bile-acid-binding-resin, a niacin, an anti-obesity drug, a hormone, an antiviral agent (e.g., to treat an underlying hepatitis C infection causing liver disease in the patient), anticancer agents (e.g., to treat hepatocellular carcinoma or other cancer causing liver disease or fatty liver), antioxidants, medications that decrease insulin resistance, or medications that improve lipid metabolism (e.g., treatments for hyperlipidemia), a tyrophostine, a sulfonylurea-based drug, a biguanide, an α-glucosidase inhibitor, an apolipoprotein A-I agonist, apolipoprotein E, a cardiovascular drug, an HDL-raising drug, an HDL enhancer, or a regulator of the apolipoprotein A-I, apolipoprotein A-IV and/or apolipoprotein genes. In some embodiments, the purified amount of the compound of formula (V), or a pharmaceutically acceptable salt thereof, is greater than 99.0% by weight of the total weight of the pharmaceutical material.

In various embodiments, the second therapeutic agent can be a statin and/or ezetimibe. See, e.g., U.S. Patent Application Publication Nos. 2018/0078518 (combination of bempedoic acid with a statin), 2018/0064671 and 2018/0338922 (combination of bempedoic acid with ezetimibe); International Publication No. WO 2018/218147 (combination of bempedoic acid with ezetimibe); and International Publication No. WO 2018/148417 (combination of bempedoic acid with ezetimibe and a statin).

In certain embodiments, administering a pharmaceutical material or a pharmaceutical composition of the present invention comprising the compound of formula (V), or a pharmaceutically acceptable salt thereof, and a second therapeutic agent is intended to provide a beneficial effect from the co-action of the compound of formula (V), or a pharmaceutically acceptable salt thereof, and a second therapeutic agent. In some embodiments, the beneficial effect of the combination therapy may include pharmacokinetic or pharmacodynamic co-action resulting from the combination of the compound of formula (V), or a pharmaceutically acceptable salt thereof, and a second therapeutic agent.

VIII. Kits

In various embodiments, the invention provides kits for treating a condition, disease or disorder described herein. In some embodiments, a kit comprises: i) instructions for treating a condition, disease or disorder, for example, as described herein, and ii) the compound of formula (V), or a pharmaceutically acceptable salt thereof (e.g., a pharmaceutical material comprising a purified amount of the compound of formula (V), or a pharmaceutically acceptable salt thereof). In some embodiments, the kit may comprise one or more unit dosage forms containing an amount of the compound of formula (V), or a pharmaceutically acceptable salt thereof, that is effective for treating the condition, disease or disorder.

The description herein includes multiple aspects and embodiments of the present invention, including methods of making the compound of formula (V), or a pharmaceutically acceptable salt thereof; methods of using a compound of formula (V), or pharmaceutically acceptable salt thereof, for example, a purified amount of the compound of formula (V), or a pharmaceutically acceptable salt thereof; compositions comprising a purified amount of the compound of formula (V), or pharmaceutically acceptable salt thereof; and kits. The patent application specifically includes all combinations and permutations of the aspects and embodiments as described herein. In particular, it should be understood that the pharmaceutical materials, pharmaceutical compositions, methods of treating a disorder or a condition, and kits can include and/or use bempedoic acid, or a pharmaceutically acceptable salt thereof, as made by the methods described herein.

EXAMPLES

In order that the invention described herein may be more fully understood, the following example is set forth. The synthetic and analytical protocols described in this application are offered to illustrate the compounds, pharmaceutical compositions, and methods provided herein and are not to be construed in any way as limiting their scope.

Example 1: Manufacturing Process for Preparing a Pharmaceutical Material Comprising a Purified Amount of the Compound of Formula (V)

In this example, the synthesis of purified bempedoic acid refers to FIG. 1.

Step 1—Preparation of Compound of Formula (I)

Lithium Diisopropylamide (LDA) Preparation

A reaction vessel was charged with diisopropylamine (317±3 kg, 1.1 eq.) and tetrahydrofuran (THF, 2,102±105 L) and the mixture then cooled to ≤−10° C. n-Butyllithium (n-BuLi, 757±8 kg, 1.2 eq.) was then dosed over ≥1 hour while the temperature was maintained at ≤−10° C. The charge line was rinsed with THF. The addition was highly exothermic. Finally, the batch was then cooled back to ≤−10° C. while being stirred.

Alkylation Reaction

Ethyl isobutyrate (317±3 kg, 1.1 eq.) was added to the reactor over ≥1 hour at ≤−10° C. (FIG. 1). The batch was stirred while maintaining the temperature at ≤−10° C. 1-Bromo-5-chloropentane (460±5 kg, 1.00 eq.) was dosed over ≥1 hour at ≤−10° C. The line was rinsed with THF. The addition was highly exothermic. The reaction mixture was then stirred for ≥10 hours at ≤−10° C. This stage of the reaction was confirmed to be complete using gas chromatography (1-bromo-5-chloropentane: ≤3% area). The reaction mixture was then warmed to 0±5° C. and this temperature maintained until the conversion was complete. The reaction was confirmed to be complete using gas chromatography (1-bromo-5-chloropentane: ≤0.5% area).

Quench and Phase Separation

A solution of 9% hydrochloric acid (HCl, 1337±50 kg) was added to the reaction mixture over ≥1 hour while the temperature was maintained at ≤30° C. to quench the reaction. After dosing, the reaction mixture was stirred at ≤30° C. for ≥15 minutes. The pH of the aqueous layer was measured (range: pH 6 to 10). The agitator was stopped and the layers were allowed to settle for ≤30 minutes. The lower aqueous phase was removed for disposal.

Distillation and Removal of THF

The solvent was removed by distillation under vacuum at ≤40° C. to the desired volume of approximately 950 L.

The concentration of the compound of formula (I) was measured using gas chromatography (GC) (target compound of formula (I) concentration range: 57-62% wt). If necessary, to adjust the concentration of the compound of formula (I) to be within the target range, THF was added or further removed via distillation.

The batch was then cooled to ≤30° C. and the crude compound of formula (I) concentrate was drummed. The process for obtaining the compound of formula (I) was repeated in an identical manner to obtain a second batch.

Step 2—Preparation of Compound of Formula (II)

Additional Aqueous Wash

Two individual batches of the compound of formula (I) (57-62% w/w solution in THF) were charged to a vessel. While stirring, 5% HCl (1,767±79 kg) was charged at ≤25° C. The addition was exothermic. The mixture was agitated for ≥15 minutes. Agitation was stopped and the phases were allowed to settle for ≥30 minutes. The lower aqueous phase was removed, leaving compound of formula (I)/THF in the reactor.

Iodide Exchange Reaction

Methyl-ethyl-ketone (MEK, 4,384±227 L) and sodium iodide (NaI, 831±9 kg, 1.16 eq.) were charged while stirring (FIG. 1). The batch was heated to reflux (75-80° C.). After approximately 30 hours, GC was used to measure reaction completion (compound of formula (I)≤1.0% area). If the reaction had not completed, additional time was allowed (expected reaction time: 25 to 35 hours) and NaI was recharged as needed. The mixture was then cooled to approximately 20° C.

Solvent Exchange and Aqueous Work-up

The batch was concentrated via vacuum distillation at ≤60° C. until no more distillate was collected. The mixture was then cooled to 20±5° C. and n-heptane (3,624±187 L) was charged. Then, 5% aqueous sodium bisulfite (NaHSO$_3$, 2,121±104 kg) was added and the mixture stirred for ≥60 minutes. Agitation was stopped and the phases allowed to settle for ≥60 minutes. The lower aqueous phase was removed for disposal. Water (1980±102 L) was added and the mixture agitated for ≥60 minutes. The phases were allowed to settle for ≥60 minutes and the lower aqueous phase removed for disposal. An optional second water wash was performed if required.

Final Concentration

The batch was concentrated using vacuum distillation at ≤50° C. until no more distillate was collected. The batch was then cooled to 20° C. and the compound of formula (II) was drummed and sampled for assay analysis. The expected yield range was 80-120% (w/w %).

Step 3—Preparation of Compound of Formula (IV)

Sodium t-Pentoxide DMAc Preparation

The following intermediate/compound of formula (IV) sequence was based on a charge of 700 kg of compound of formula (II)/n-heptane with assay of 94.9% wt/wt, which represented a contained charge of 665 kg of compound of formula (II).

A solution of N,N-dimethylacetamide (DMAc, 1,476±37 kg) and sodium t-pentoxide (271±3 kg, 2.10 eq.) was prepared in a vessel and the mixture was agitated for approximately 30 minutes until nearly all of the solids were dissolved.

Preparation of the First Intermediate

Compound of formula (II) (700 kg, 1 eq.), DMAc (1,272±27 kg), and TosMIC (219±1 kg) were charged to a vessel (see FIG. 1). The mixture was cooled to ≤−5° C. and well agitated. To this solution, the sodium t-pentoxide/DMAc mixture was added over approximately 1 hour at ≤−5° C. The transfer line was rinsed with DMAc (181±9 kg). The reaction was strongly exothermic. The reaction mixture was agitated for ≥30 minutes at ≤−5° C. The conversion was confirmed to be complete using high-performance liquid chromatography with ultraviolet detection (HPLC-UV) (monoalkylated TosMIC ≤1% area and compound of formula (II)≤1.4% area). Optional kicker charges of compound of formula (II), TosMIC and sodium t-pentoxide were employed as required, to ensure completion of the reaction, based on the following instructions (Table 18):

TABLE 18

Instructions for Determining Kicker Charge Action

| IPC Test Result Criteria | Kicker Charge Action |
|---|---|
| ≤1% Monoalkylated TosMIC and >1.4% compound of formula (II) | Charge additional TosMIC and sodium t-pentoxide |
| >1% Monoalkylated TosMIC and ≤1.4% compound of formula (II) | Charge additional compound of formula (II) |
| >1% Monoalkylated TosMIC and >1.4% compound of formula (II) | Charge additional sodium t-pentoxide |

Quench and Phase Separation n-Heptane (2,407±120 L) and water (3,061±153 L) were charged to another reactor. The first intermediate reaction mixture was transferred to the n-heptane/water mixture under temperature control between 0° C. and 40° C. (target 20° C.). The reaction was slightly exothermic. The transfer line was rinsed with n-heptane (470±24 L). The mixture was then agitated for ≥1 hour. Agitation was stopped and the mixture allowed to settle for ≥1 hour. The lower aqueous phase was removed for disposal. A solution of 5% aqueous sodium chloride (NaCl, 3,106±147 kg) was charged and the mixture agitated for ≥1 hour at approximately 20° C. (range: 0° C. to 40° C.). The agitator was stopped and the mixture allowed to settle for ≥60 minutes. The lower aqueous phase was removed for disposal. The remaining solution of the first intermediate in n-heptane was transferred to another vessel.

Compound of Formula (IV) Reaction

Isopropyl acetate (IPAc, 451±23 L) was added to the solution of the first intermediate in n-heptane and the mixture cooled to −10±10° C. Concentrated HCl (115±2 kg) was added while maintaining the temperature at ≤25° C. The reaction was exothermic and the reaction mixture allowed to warm, if needed, to 20±5° C. The mixture was agitated for ≥30 minutes during the warming period. The reaction conversion was measured using HPLC-UV (intermediate≤2% area).

Quench and Phase Separation

In a separate vessel, a sodium hydroxide (NaOH) solution (50% wt/wt, 175±2 kg) was combined with water (1927±96 L). The resulting aqueous NaOH solution was added to the reaction mixture at approximately 20° C. (range: 10° C. to 40° C.). The line was rinsed with water. The mixture was stirred for ≥3 hours. The neutralization endpoint is pH 9 to 12. Agitation was stopped and the phases allowed to settle for ≥60 minutes. The lower aqueous phase was removed for disposal. A dilute aqueous solution, containing NaCl (55±3 kg), water (1,572±79 L) and 50% sodium hydroxide (4.6±0.2 kg), was prepared in a separate vessel and charged to the compound of formula (IV) product mixture. A water rinse (128±6 L) was applied and the mixture was agitated for ≥60 minutes. Agitation was stopped and the phases were allowed to settle for ≥60 minutes. The lower aqueous phase was removed for disposal.

Concentration

The mixture was concentrated under vacuum at ≤80° C. until no more distillate was collected. The distillation was monitored using GC (compound of formula (IV) 75% area). The batch was cooled to approximately 20° C. and the compound of formula (IV) concentrate was held until the second batch was prepared. The process for preparing the compound of formula (IV) was repeated in an identical manner to provide a second batch of the compound of formula (IV) in n-heptane. The second batch (in n-heptane) was then combined with the first batch for final distillation and packaging. The product was weighed and sampled for assay. The expected yield range is 80-120% w/w.

Step 4—Preparation of Compound of Formula (V) (Crude Bempedoic Acid)

Reaction 1 (Ketone Reduction)

Compound of formula (IV) (545±5 kg) and ethanol (EtOH, 1090±55 kg) were charged to a vessel. While maintaining the batch at ≤35° C., sodium borohydride ($NaBH_4$, 12 wt % in 40% NaOH, 155±2 kg, 0.35 eq.) was charged over approximately 2-3 hours (FIG. 1). The addition was exothermic. The charging line was rinsed with water (155±8 kg). After holding at 25±10° C. for 1 hour the conversion was measured using HPLC-UV (compound of formula (IV) 0.5% area).

Reaction 2 (Saponification)

An aqueous solution of NaOH (50% wt/wt, 435±4 kg) was charged to the vessel at 50° C. The addition was exothermic. The charging line was rinsed with water (155±8 kg) and the reaction mixture was warmed to 50±5° C. for 6 hours. The saponification was measured using HPLC-UV (compound of formula (V) monoester 0.5% area). Water (1873±94 kg) was charged to the reaction mixture. EtOH and water were distilled under vacuum and at ≤50° C. until the batch volume reached the target level (approximately 2184 L). The mixture was transferred to another reactor and the transfer line was rinsed with water (273±14 kg).

pH Adjustment, Phase Separation, and Extraction

Methyl tert-butyl ether (MTBE, 1628±81 kg) was added and the batch cooled to 10-15° C. Concentrated HCl (647±6 kg) was added slowly at 10-20° C. (the addition was exothermic) and the batch stirred≥1 hour. A sample was taken for pH analysis and the pH was adjusted with HCl or NaOH as needed (target pH range: 5 to 6). The formation of hydrogen gas was observed. Agitation was stopped and the phases were allowed to settle for ≥60 minutes at 10-20° C. The lower aqueous phase was removed for disposal. The batch was transferred to another vessel and rinsed forward with MTBE. The concentration of compound of formula (V) in MTBE was measured using HPLC-UV (compound of formula (V): 17% to 20% weight).

Step 5—Purification of Compound of Formula (V)/Preparation of Crystalline Form of Compound of Formula (V)

Silica Gel Preparations

The diameter×height ratio for the silica gel plug varied from 1×1 to 1×3. Silica gel (60±2 kg) was charged to a filter and wetted with ethyl acetate (EtOAc) that was charged into the reactor and then drained to the filter. The silica gel bed was preheated by recirculating EtOAc (1,173±59 kg) at 50±5° C. Excess EtOAc was removed immediately prior to filtration of the compound of formula (V) batch.

Solvent Exchange to Ethyl Acetate

The compound of formula (V) in MTBE was charged to a reactor. The batch was concentrated under vacuum at ≤50° C. to 30% to 35% of the initial volume. EtOAc (2,002±100 kg) was charged and the batch was concentrated again to 30% to 35% of the initial volume. EtOAc (1601±80 kg) was charged and distillation is repeated. EtOAc (1601±80 kg) was charged and the batch was sampled. The solvent exchange was measured by GC (MTBE≤0.1% weight). Additional EtOAc charges and distillations were performed as required.

Silica Gel Filtration

When the solvent exchange was complete, the batch was warmed to 50±5° C. Then the batch was filtered through the preheated silica gel plug into another reactor. To rinse the line and the silica gel, EtOAc (964±20 kg) was charged to the reactor, warmed to 50° C., and then a portion of the warm EtOAc was transferred through the silica gel plug. Loss of product due to retention on the silica gel filter was measured using HPLC (compound of formula (V)≤0.5% weight in the eluate). Additional flushes with EtOAc were performed as required. Purified compound of formula (V) in EtOAc was partially concentrated by distillation under vacuum, at ≤50° C., to a final volume of approximately 1700 L.

Crystallization

The temperature of the concentrated compound of formula (V) in EtOAc was adjusted to approximately 50±5° C. Water (24±1 kg) was charged, the line was rinsed with EtOAc (74±10 kg) and the solution was maintained at 50±5° C. for ≥1 hour. The solution was then cooled to 22±5° C. using a cooling rate of 14° C./hour, with slow agitation, and then held at this temperature for ≥2 hours to initiate crystallization. Once slurry formation was confirmed, the solution was stirred at approximately 20-25° C. for ≥6 hours. The batch was then cooled to 0±5° C. using a cooling rate of 11° C./hour and then stirred at this temperature for ≥6 hours.

Isolation and Drying

The crude crystalline form of the compound of formula (V) was isolated by centrifugation at 0±5° C. and then washed with chilled EtOAc at 0±5° C. The wet cake was dried under vacuum at 45° C. Drying was monitored by loss-on drying (LOD) (LOD≤0.5%).

Optional In Situ Filtration

For vessels designed with in-reactor (in situ) filtration, the slurry was allowed to settle for ≥1 hour at 0±5° C. The batch was filtered and the wet cake was left in the reactor. EtOAc (1,064±53 kg) was charged to another vessel, chilled to 0±5° C. and transferred, backwards through the decant filters, to the reactor containing the wet cake. The batch was agitated for ≥1 hour and then allowed to settle for ≥1 hour. Filtration was repeated. The slurry wash and filtration process was repeated three times in an identical manner.

Step 6—Preparation of Pharmaceutical Material Including Purified Amount of Compound of Formula (V)

Recrystallization (Ethyl Acetate Water)

Following in situ filtration, the amount of the crystalline form of the compound of formula (V) produced in Step 5 was estimated based on the assumption that there was 100% conversion of the compound of formula (IV) (charge amount—545 kg) into the compound of formula (V) in Step 4 (FIG. 1).

In a reactor, EtOAc was charged to the crystalline form of the compound of formula (V) wetcake until the volume reaches the 1433 L mark (approximately 619 kg of EtOAc) and the suspension was then heated to 55-60° C. until all solids dissolved. To the clear solution, water (16±1 kg) was added and the batch agitated at 55-70° C. for ≥1 hour. The temperature was adjusted to 55±5° C. and the batch was then transferred to another reactor via polish filtration. The reactor, filter and line were rinsed with EtOAc (162±12 kg). The temperature was adjusted to 55±5° C. The hot solution was then cooled over ≥1 hour to 30±5° C. and agitated for ≥2 hours. The batch was then heated over ≥1 hour to 40±5° C. and then maintained at 40±5° C. for ≥1 hour. The batch was then cooled over ≥1 hour to 35±5° C. and then maintained at 35±5° C. for ≥2 hours. The batch was then cooled over ≥5 hours to 5±5° C. and then maintained at 5±5° C. for ≥4 hours. The resulting solids were isolated by centrifugation. The wash solvent was acetonitrile (ACN), stored for use at 20±10° C.

Isolation, Drying, Compound Identification of the Compound of Formula (V) and IPC Testing The purified compound of formula (V) solids were collected by centrifugation and then washed with acetonitrile (2×2 kg/kg of the compound of formula (V)) at 20±10° C. to remove all residual mother liquor. The wet cake was dried in vacuum at ≤45° C. Yield: 324.2 kg (84.9%) of a pharmaceutical material comprising a purified amount of the compound of formula (V).

Figure 2:
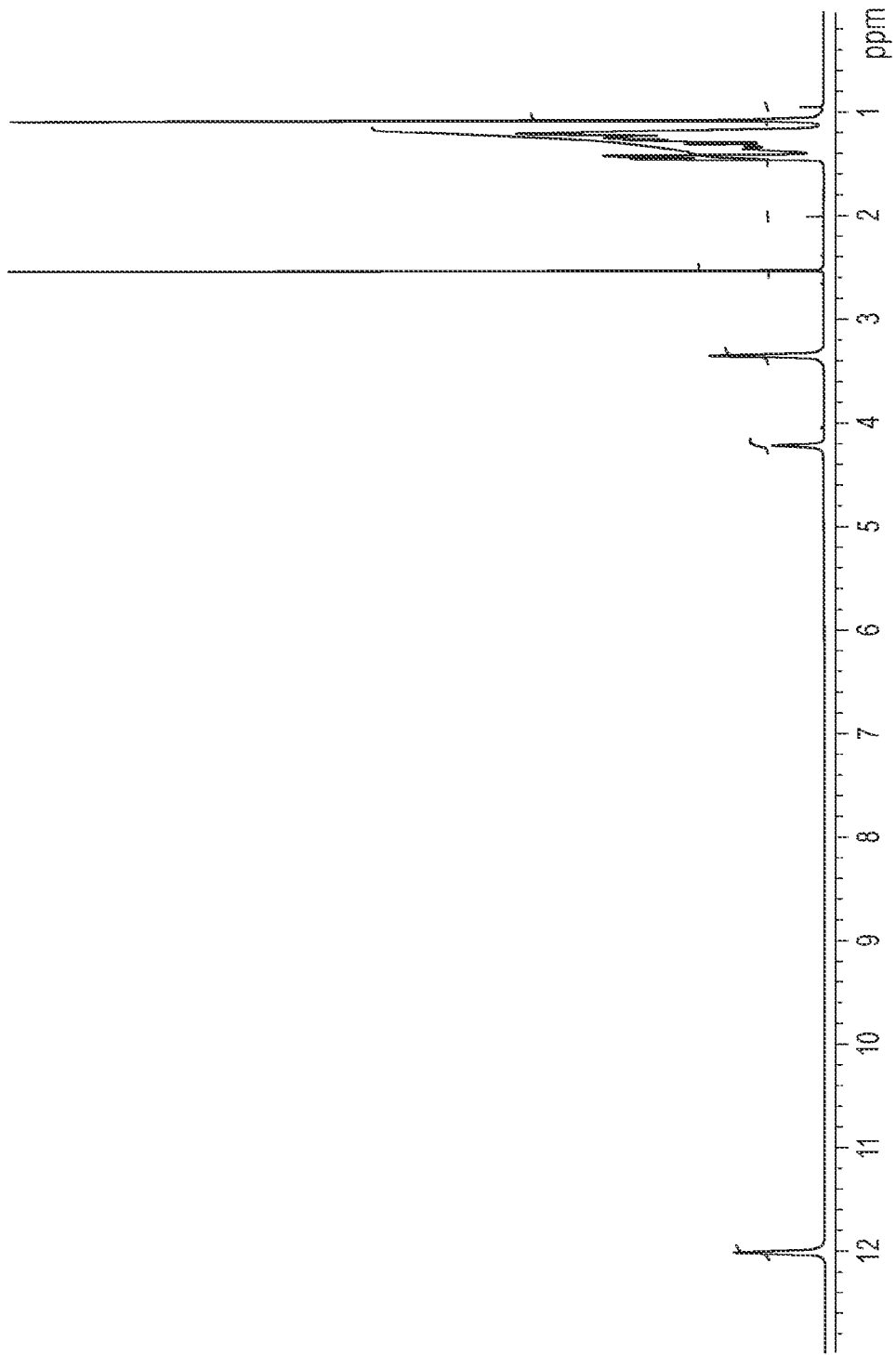
FIG. 2 is an exemplary $^1$H-NMR spectrum of the compound of formula (V).
Figure 3:
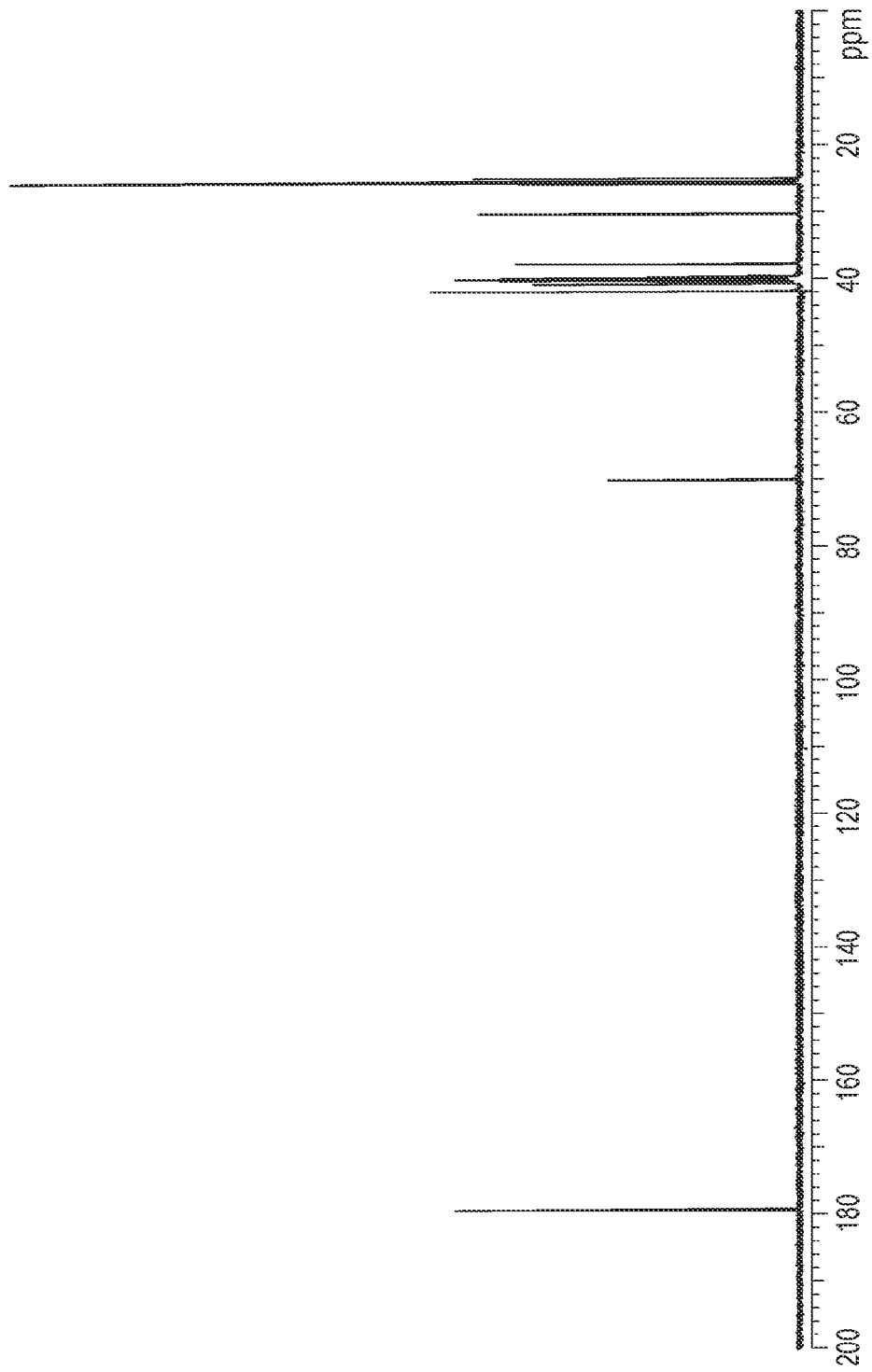
FIG. 3 is an exemplary $^{13}$C-NMR spectrum of the compound of formula (V).

The purified compound of formula (V) was prepared for $^1$H- and $^{13}$C-NMR analysis by preparing 10 mg/mL and 50 mg/mL solutions of the purified compound of formula (V) in CDCl$_3$. $^1$H- and $^{13}$C-NMR spectra were obtained using an Inova 500 MHz NMR spectrometer. To ensure better relative quantitation of the integrals and that all signals were captured the window was expanded from 5000 to 8000 Hz and the wait time extended between acquisitions from 1 to 25 sec. The resulting $^1$H- and $^{13}$C-NMR spectra of the compound of formula (V) (FIGS. 2(*a*) and 2(*b*), respectively) are consistent with known $^1$H- and $^{13}$C-NMR spectra of bempedoic acid (Table 19).

TABLE 19

| Bempedoic acid $^1$H— and $^{13}$C—NMR assignments | | |
|---|---|---|
| Signal Assignment | Signal Location (ppm) | |
| Nucleus | Proton (mult) | Carbon |
| CO$_2$H | 11.99 (singlet) | 179.05 |
| C2 | N/A | 41.43 |
| (CH$_3$)$_2$ | 1.05 (singlet) | 25.23 |
| C3/H3 | 1.41 (multiplet) | 40.46 |
| C4/H4 | 1.15-1.34 (multiplet) | 24.78 |
| C5/H5 | 1.15-1.34 (multiplet) | 29.99 |
| C6/H6 | 1.15-1.34 (multiplet) | 25.42 |
| C7/H7 | 1.41 (multiplet) | 37.39 |
| C8/H8 | 3.32 (singlet) | 69.69 |
| OH | 4.19 (singlet) | N/A |

A sample of the purified compound of formula (V) was run on an Agilent 1100 HPLC coupled to a Thermo LTQ-XL Mass Spectrometer electrospray running in positive electrospray mode. The capillary temperature was 200° C. The column was a Waters X-Bridge C18, 4.6×75 mm, 2.5 μm. Mobile phase A was 0.05% formic acid and mobile phase B was 0.04% formic acid in acetonitrile. The experimental mass of the compound of formula (V) was found to be 344.38 Da, which is in good agreement with the calculated mass for bempedoic acid of 344.49 Da.

The expected yield range was 66-91%. The residual solvent was measured using GC (ACN≤350 ppm) to determine completion of drying. When drying was complete, impurities were measured using HPLC with charged aerosol detection (CAD) (unknown impurities≤0.08% by weight and known impurities≤0.13% by weight). If the impurity profile criterion was met, the product was treated as the final Active Pharmaceutical Ingredient (API). If the impurity profile criterion was not met, another recrystallization was performed as described above.

Using the HPLC assay described in Example 3, the purity of the purified compound of formula (V) was determined to be 99.6% (w/w).

X-ray powder diffraction (XRPD) data for the crystalline form of the compound of formula (V) were collected using a Panalytical X'Pert³ Powder diffractometer (Cu, Kα radiation; X-ray tube setting—45 kV, 40 mA; divergence slit—fixed ⅛°; scan mode—continuous; scan range—3 to 40° (2θ); scan step time—18.87 seconds; step size—0.0131° (2θ)). Samples of the crystalline form of the compound of formula (V) were placed on a Si zero-background holder. The 2 theta position was calibrated against a Panalytical Si reference standard disc. An XRPD pattern of the crystalline form of the compound of formula (V) is provided in FIG. 4. Tabulated characteristics of the XRPD pattern in FIG. 4 are provided below in Table 20, which lists diffraction angle 2θ and relative intensity (expressed as a percentage with respect to the most intense peak).

Differential Scanning Calorimetry (DSC) data for the crystalline form of the compound of formula (V) were collected using a TA Q2000 DSC instrument. The DSC instrument was calibrated using an indium reference standard. Samples of the crystalline form of the compound of formula (V) were placed inside crimped aluminum sample pans and heated at a rate of 10° C./minute from ambient temperature (~25° C.) to 300° C. A DSC curve for the crystalline form of the compound of formula (V) is provided in FIG. 5. The DSC curve displayed an endothermic event with an onset value of about 92.4° C.

Thermogravimetric analysis (TGA) data for the crystalline form of the compound of formula (V) were collected using a TA Discovery 550 TGA instrument. The TGA instrument was calibrated using a nickel reference standard. Samples of the crystalline form of the compound of formula (V) were placed in open platinum sample pans and heated at a rate of 10° C./minute from about ambient temperature (~25° C.) to about 315° C. A TGA curve for the crystalline form of the compound of formula (V) is provided in FIG. 6. The TGA curve displayed negligible weight loss prior to decomposition occurring.

TABLE 20

X-ray Powder Diffraction Pattern Data of the
Crystalline Form of the Compound of Formula (V)

| Angle [2θ] | Relative Intensity [%] |
| --- | --- |
| 5.2 | 2.33 |
| 10.3 | 70.75 |
| 10.4 | 78.65 |
| 11.8 | 2.88 |
| 13.7 | 2.72 |
| 15.5 | 8.08 |
| 15.6 | 7.16 |
| 17.3 | 8.20 |
| 17.6 | 18.72 |
| 17.9 | 100.00 |
| 18.8 | 42.30 |
| 19.5 | 21.42 |
| 19.7 | 15.07 |
| 20.4 | 16.93 |
| 20.7 | 23.95 |
| 21.1 | 5.78 |
| 22.0 | 13.87 |
| 22.6 | 17.54 |
| 23.1 | 7.78 |
| 23.6 | 4.97 |
| 23.9 | 6.19 |
| 24.7 | 1.98 |
| 25.8 | 3.04 |
| 26.3 | 2.10 |
| 27.5 | 13.36 |
| 29.2 | 3.86 |
| 30.2 | 1.27 |
| 30.8 | 5.34 |
| 31.3 | 1.40 |
| 31.9 | 2.95 |
| 32.9 | 1.27 |
| 34.4 | 5.98 |
| 35.1 | 2.07 |
| 36.2 | 3.16 |
| 37.2 | 2.37 |
| 37.9 | 1.79 |

In addition, single crystals of the crystalline form of the compound of formula (V) were analyzed by single crystal X-ray diffraction. The unit cell parameters of the crystalline form of the compound of formula (V) and the data collection and structure refinement methods are shown in Tables 21 and 22, respectively.

TABLE 21

Unit Cell Parameters of the Crystalline
Form of the Compound of Formula (V)

| | |
| --- | --- |
| Empirical formula | $C_{19}H_{36}O_5$ |
| Formula weight | 344.48 |
| Temperature | 297(2) K |
| Wavelength | 0.71073 Å |
| Crystal size | 0.400 × 0.140 × 0.090 mm |
| Crystal system | Monoclinic |
| Space group | $P2_1/c$ |
| Unit cell dimensions | a = 17.9209(8) Å   α = 90° |
| | b = 9.8547(5) Å    β = 106.8340(10)° |
| | c = 12.2775(6) Å   γ = 90° |
| Volume | 2075.35(17) Å³ |
| Z | 4 |
| Density (calculated) | 1.102 Mg/m³ |
| Absorption coefficient | 0.078 mm⁻¹ |
| F(000) | 760 |

TABLE 22

Data Collection and Structure Refinement Methods for the Crystalline Form of the Compound of Formula (V)

| | |
|---|---|
| Diffractometer | Bruker D8 Quest PHOTON 100 CMOS |
| Radiation source | Incoatec Microfocus Source (IμS) monochromated MoKα |
| Data collection method | omega/phi scans |
| Theta range for data collection | 2.384° to 25.243° |
| Limiting indices | −21<=h<=21, −11<=k<=11, −14<=l<=14 |
| Reflections collected/unique | 51013/3745 [R(int) = 0.0514] |
| Completeness to theta = 25.242 | 99.8% |
| Absorption correction | Semi-empirical from equivalents |
| Max. and min. transmission | 0.7454 and 0.6534 |
| Refinement method | Full-matrix least-squares on $F^2$ |
| Data/restraints/parameters | 3745/3/228 |
| Goodness-of-fit on $F^2$ | 1.027 |
| Final R indices [I > 2 sigma(I)] | R1 = 0.0684, wR2 = 0.1658 |
| R indices (all data) | R1 = 0.0858, wR2 = 0.1780 |
| Extinction coefficient | n/a |
| Largest diff. peak and hole | 0.956 and −0.379 e · A$^{-3}$ |

Atomic coordinates (×10$^4$) and equivalent isotropic displacement parameters (Å$^2$×10$^3$) are shown in Table 23, below. U(eq) is defined as one third of the trace of the orthogonalized U$^{ij}$ tensor.

TABLE 23

Atomic Coordinates and Equivalent Isotropic Atomic Displacement Parameters for the Crystalline Form of the Compound of Formula (V)

| Atom | x | y | z | U(eq) |
|---|---|---|---|---|
| O1 | 8702(1) | 759(2) | 9437(2) | 54(1) |
| O2 | 7773(1) | 838(2) | 10289(2) | 61(1) |
| O3 | 7792(1) | 9467(2) | 7690(2) | 64(1) |
| O4 | 3323(1) | 6206(2) | 3606(2) | 61(1) |
| O5 | 3141(1) | 8412(2) | 3400(2) | 58(1) |
| C1 | 8438(2) | 1070(2) | 10303(2) | 39(1) |
| C2 | 9051(1) | 1748(3) | 11258(2) | 40(1) |
| C3 | 8742(2) | 1960(4) | 12278(3) | 65(1) |
| C4 | 9778(2) | 833(3) | 11597(3) | 62(1) |
| C5 | 9260(2) | 3111(3) | 10806(2) | 43(1) |
| C6 | 8566(2) | 4011(3) | 10253(3) | 50(1) |
| C7 | 8782(2) | 5364(3) | 9841(2) | 53(1) |
| C8 | 8072(2) | 6113(3) | 9111(3) | 55(1) |
| C9 | 8256(2) | 7413(3) | 8618(3) | 65(1) |
| C10 | 7539(2) | 8176(3) | 7903(3) | 57(1) |
| C11 | 7131(2) | 7409(3) | 6807(2) | 51(1) |
| C12 | 6389(2) | 8053(3) | 6074(2) | 52(1) |
| C13 | 5964(2) | 7180(3) | 5081(3) | 53(1) |
| C14 | 5205(2) | 7760(3) | 4343(2) | 49(1) |
| C15 | 4828(1) | 6862(3) | 3332(2) | 44(1) |
| C16 | 4040(1) | 7331(3) | 2540(2) | 42(1) |
| C17 | 3762(2) | 6284(3) | 1581(3) | 61(1) |
| C18 | 4109(2) | 8719(3) | 2026(3) | 60(1) |
| C19 | 3454(1) | 7401(3) | 3216(2) | 41(1) |

Bond lengths (Å) are shown in Table 24, below.

TABLE 24

Selected Bond Lengths (Å) for the Crystalline Form of the Compound of Formula (V)

| Bond | Bond length (Å) |
|---|---|
| O(1)—H(1) | 0.862(18) |
| O(1)—C(1) | 1.318(3) |
| O(2)—C(1) | 1.209(3) |
| O(3)—H(3) | 0.910(18) |
| O(3)—C(10) | 1.400(3) |
| O(4)—H(4) | 0.859(18) |
| O(4)—C(19) | 1.318(3) |
| O(5)—C(19) | 1.197(3) |

TABLE 24-continued

Selected Bond Lengths (Å) for the Crystalline Form of the Compound of Formula (V)

| Bond | Bond length (Å) |
|---|---|
| C(1)—C(2) | 1.511(4) |
| C(2)—C(4) | 1.540(4) |
| C(2)—C(3) | 1.523(4) |
| C(2)—C(5) | 1.540(4) |
| C(5)—C(6) | 1.519(4) |
| C(6)—C(7) | 1.514(4) |
| C(7)—C(8) | 1.519(4) |
| C(8)—C(9) | 1.494(4) |
| C(9)—C(10) | 1.528(4) |
| C(10)—C(11) | 1.532(4) |
| C(11)—C(12) | 1.512(4) |
| C(12)—C(13) | 1.507(4) |
| C(13)—C(14) | 1.511(4) |
| C(14)—C(15) | 1.515(4) |
| C(15)—C(16) | 1.535(4) |
| C(16)—C(19) | 1.516(4) |
| C(16)—C(17) | 1.536(4) |
| C(16)—C(18) | 1.527(4) |

Bond angles (°) are shown in Table 25, below.

TABLE 25

Selected Bond Angles (°) for the Crystalline Form of the Compound of Formula (V)

| Bond | Bond angle (°) | Bond | Bond angle (°) |
|---|---|---|---|
| H(1)—O(1)—C(1) | 109(2) | O(3)—C(10)—C(9) | 106.9(2) |
| H(3)—O(3)—C(10) | 107(2) | O(3)—C(10)—C(11) | 112.5(2) |
| H(4)—O(4)—C(19) | 114(3) | C(9)—C(10)—C(11) | 111.7(3) |
| O(2)—C(1)—O(1) | 121.8(2) | C(12)—C(11)—C(10) | 115.4(2) |
| O(2)—C(1)—C(2) | 125.9(2) | C(11)—C(12)—C(13) | 113.1(2) |
| O(1)—C(1)—C(2) | 112.2(2) | C(12)—C(13)—C(14) | 115.2(2) |
| C(1)—C(2)—C(4) | 108.6(2) | C(15)—C(14)—C(13) | 112.4(2) |
| C(1)—C(2)—C(3) | 110.1(2) | C(14)—C(15)—C(16) | 117.0(2) |
| C(4)—C(2)—C(3) | 109.8(2) | C(19)—C(16)—C(15) | 108.8(2) |
| C(1)—C(2)—C(5) | 107.70(19) | C(19)—C(16)—C(17) | 109.1(2) |
| C(4)—C(2)—C(5) | 109.4(2) | C(15)—C(16)—C(17) | 108.6(2) |
| C(3)—C(2)—C(5) | 111.2(2) | C(19)—C(16)—C(18) | 109.7(2) |
| C(6)—C(5)—C(2) | 114.7(2) | C(15)—C(16)—C(18) | 111.2(2) |
| C(7)—C(6)—C(5) | 114.1(2) | C(17)—C(16)—C(18) | 109.4(2) |
| C(6)—C(7)—C(8) | 112.0(2) | O(5)—C(19)—O(4) | 122.2(2) |
| C(7)—C(8)—C(9) | 114.3(2) | O(5)—C(19)—C(16) | 125.3(2) |
| C(8)—C(9)—C(10) | 114.0(3) | O(4)—C(19)—C(16) | 112.5(2) |

Torsion angles (°) are shown in Table 26, below.

TABLE 26

Selected Torsion Angles (°) for the Crystalline Form of the Compound of Formula (V)

| | Torsion angle (°) | | Torsion angle (°) |
|---|---|---|---|
| H(1)—O(1)—C(1)—O(2) | −3(3) | C(8)—C(9)—C(10)—C(11) | −67.6(4) |
| H(1)—O(1)—C(1)—C(2) | 178(3) | O(3)—C(10)—C(11)—C(12) | −62.9(4) |
| O(2)—C(1)—C(2)—C(4) | 126.7(3) | C(9)—C(10)—C(11)—C(12) | 176.9(3) |
| O(1)—C(1)—C(2)—C(4) | −54.3(3) | C(10)—C(11)—C(12)—C(13) | −173.4(3) |
| O(2)—C(1)—C(2)—C(3) | 6.5(4) | C(11)—C(12)—C(13)—C(14) | 178.2(3) |
| O(1)—C(1)—C(2)—C(3) | −174.5(2) | C(12)—C(13)—C(14)—C(15) | 177.3(3) |
| O(2)—C(1)—C(2)—C(5) | −114.9(3) | C(13)—C(14)—C(15)—C(16) | 178.3(2) |
| O(1)—C(1)—C(2)—C(5) | 64.2(3) | C(14)—C(15)—C(16)—C(19) | −61.2(3) |
| C(1)—C(2)—C(5)—C(6) | 52.0(3) | C(14)—C(15)—C(16)—C(17) | −179.8(2) |
| C(4)—C(2)—C(5)—C(6) | 169.9(2) | C(14)—C(15)—C(16)—C(18) | 59.7(3) |
| C(3)—C(2)—C(5)—C(6) | −68.7(3) | H(4)—O(4)—C(19)—O(5) | 4(3) |
| C(2)—C(5)—C(6)—C(7) | 178.4(2) | H(4)—O(4)—C(19)—C(16) | −176(3) |
| C(5)—C(6)—C(7)—C(8) | 169.7(2) | C(15)—C(16)—C(19)—O(5) | 116.1(3) |
| C(6)—C(7)—C(8)—C(9) | −176.1(3) | C(17)—C(16)—C(19)—O(5) | −125.6(3) |
| C(7)—C(8)—C(9)—C(10) | −178.9(3) | C(18)—C(16)—C(19)—O(5) | −5.8(4) |
| H(3)—O(3)—C(10)—C(9) | −174(2) | C(15)—C(16)—C(19)—O(4) | −63.2(3) |
| H(3)—O(3)—C(10)—C(11) | 63(2) | C(17)—C(16)—C(19)—O(4) | 55.1(3) |
| C(8)—C(9)—C(10)—O(3) | 168.9(3) | C(18)—C(16)—C(19)—O(4) | 174.9(2) |

Anisotropic Displacement Parameters ($Å^2$) are shown in Table 27, below. The anisotropic displacement factor exponent may be expressed in the form: $-2\pi^2[h^2a^{*2}U^{11}+\ldots+2hka^*b^*U^{12}]$.

TABLE 27

Anisotropic Displacement Parameters ($Å^2$) for the Crystalline Form of the Compound of Formula (V)

| Atom | U11 | U22 | U33 | U23 | U13 | U12 |
|---|---|---|---|---|---|---|
| O1 | 52(1) | 60(1) | 48(1) | −18(1) | 13(1) | −4(1) |
| O2 | 48(1) | 70(1) | 70(1) | −12(1) | 23(1) | −12(1) |
| O3 | 70(1) | 38(1) | 67(1) | −1(1) | −7(1) | 3(1) |
| O4 | 67(1) | 40(1) | 92(2) | 12(1) | 47(1) | 7(1) |
| O5 | 57(1) | 39(1) | 83(2) | 0(1) | 26(1) | 10(1) |
| C1 | 44(1) | 31(1) | 42(1) | 4(1) | 12(1) | 5(1) |
| C2 | 44(1) | 42(1) | 32(1) | 3(1) | 6(1) | 4(1) |
| C3 | 76(2) | 80(2) | 39(2) | 3(2) | 17(2) | 0(2) |
| C4 | 56(2) | 60(2) | 61(2) | 14(2) | 1(1) | 15(2) |
| C5 | 43(1) | 40(1) | 39(1) | −2(1) | 1(1) | −3(1) |
| C6 | 52(2) | 44(2) | 55(2) | 6(1) | 15(1) | 6(1) |
| C7 | 61(2) | 37(2) | 50(2) | −1(1) | −4(1) | −2(1) |
| C8 | 61(2) | 40(2) | 59(2) | 4(1) | 10(1) | 5(1) |
| C9 | 63(2) | 36(2) | 74(2) | 8(1) | −14(2) | −9(1) |
| C10 | 54(2) | 44(2) | 60(2) | 8(1) | −3(1) | −6(1) |
| C11 | 49(2) | 36(1) | 59(2) | 0(1) | 1(1) | 0(1) |
| C12 | 48(2) | 44(2) | 57(2) | −4(1) | 3(1) | 1(1) |
| C13 | 45(2) | 47(2) | 59(2) | −8(1) | 5(1) | 3(1) |
| C14 | 44(2) | 44(2) | 55(2) | −6(1) | 8(1) | 2(1) |
| C15 | 40(1) | 40(1) | 54(2) | −7(1) | 15(1) | 0(1) |
| C16 | 39(1) | 40(1) | 45(1) | −2(1) | 11(1) | −4(1) |
| C17 | 60(2) | 67(2) | 55(2) | −16(2) | 16(1) | −13(2) |
| C18 | 62(2) | 55(2) | 63(2) | 14(2) | 16(2) | −6(2) |
| C19 | 35(1) | 36(1) | 48(2) | −1(1) | 7(1) | 2(1) |

Hydrogen atom coordinates and isotropic atomic displacement parameters ($Å^2$) are shown in Table 28, below.

TABLE 28

Hydrogen Atom Coordinates and Isotropic Displacement Parameters ($Å^2$) for the Crystalline Form of the Compound of Formula (V)

| Atom | x | y | z | U |
|---|---|---|---|---|
| H(1) | 8339(16) | 350(30) | 8930(20) | 81(12) |
| H(3) | 7357(15) | 9950(30) | 7330(30) | 85 |
| H(4) | 2972(18) | 6210(40) | 3960(30) | 90(13) |
| H(3B) | 9136 | 2391 | 12880 | 97 |
| H(3C) | 8287 | 2525 | 12061 | 97 |
| H(3D) | 8610 | 1098 | 12537 | 97 |
| H(4A) | 10173 | 1252 | 12205 | 93 |
| H(4B) | 9642 | −32 | 11845 | 93 |
| H(4C) | 9973 | 708 | 10953 | 93 |
| H(5A) | 9609 | 3604 | 11434 | 52 |
| H(5B) | 9541 | 2928 | 10255 | 52 |
| H(6A) | 8224 | 3531 | 9611 | 60 |
| H(6B) | 8277 | 4176 | 10797 | 60 |
| H(7A) | 9146 | 5214 | 9403 | 64 |
| H(7B) | 9039 | 5921 | 10493 | 64 |
| H(8A) | 7725 | 6306 | 9569 | 66 |
| H(8B) | 7795 | 5522 | 8494 | 66 |
| H(9A) | 8594 | 7218 | 8147 | 78 |
| H(9B) | 8541 | 7997 | 9234 | 78 |
| H(10A) | 7171 | 8278 | 8352 | 68 |
| H(11A) | 7493 | 7322 | 6357 | 62 |
| H(11B) | 7010 | 6500 | 7009 | 62 |
| H(12A) | 6516 | 8915 | 5790 | 63 |
| H(12B) | 6046 | 8235 | 6540 | 63 |
| H(13A) | 5858 | 6307 | 5370 | 63 |
| H(13B) | 6305 | 7021 | 4609 | 63 |
| H(14A) | 4848 | 7873 | 4799 | 59 |
| H(14B) | 5302 | 8648 | 4073 | 59 |
| H(15A) | 4758 | 5967 | 3616 | 53 |
| H(15B) | 5189 | 6770 | 2881 | 53 |
| H(17A) | 4131 | 6235 | 1151 | 91 |
| H(17B) | 3718 | 5410 | 1904 | 91 |
| H(17C) | 3262 | 6552 | 1090 | 91 |
| H(18A) | 4480 | 8671 | 1599 | 90 |
| H(18B) | 3610 | 8983 | 1531 | 90 |
| H(18C) | 4279 | 9376 | 2624 | 90 |

Selected hydrogen bond information (Å and °) shown in Table 29, below.

TABLE 29

Selected Hydrogen Bond Formation (Å and °) for the Crystalline Form of the Compound of Formula (V)

| D—H...A | d(D—H) | d(H...A) | d(D...A) | <(DHA) |
|---|---|---|---|---|
| O(1)—H(1)...O(3) #1 | 0.862(18) | 1.78(2) | 2.618(3) | 165(3) |
| O(3)—H(3)...O(5) #2 | 0.910(18) | 1.94(3) | 2.768(3) | 151(3) |
| O(4)—H(4)...O(2) #3 | 0.859(18) | 1.87(2) | 2.716(3) | 168(4) |

Symmetry transformations used to generate equivalent atoms: #1 x,y−1,z #2−x+1, −y+2, −z+1 #3−x+1,y+1/2, −z+3/2

Example 2: Alternative Manufacturing Process for Preparing a Pharmaceutical Material Comprising a Purified Amount of the Compound of Formula (V)

Step 1—Preparation of Compound of Formula (I)

Lithium Diisopropylamide (LDA) Preparation

A reaction vessel was charged with approximately 321 kg of diisopropylamine and approximately 1870 L of tetrahydrofuran (THF) and the mixture was then cooled to −18° C. to −5° C. Approximately 794 kg of n-butyllithium (n-BuLi, solution in heptane) was slowly dosed while maintaining the temperature at −18° C. to −5° C. The batch was held to −18° C. to −5° C. with stirring.

Alkylation Reaction

Approximately 317 kg of ethyl isobutyrate was added to the reactor containing the LDA over a target≥1 hour with the temperature controlled at −18° C. to −5° C. The line was then rinsed with approximately 100 L THF. The batch was stirred while maintaining the temperature at −18° C. to −5° C. Approximately 460 kg of 1-bromo-5-chloropentane was dosed over a target≥1 hour at −18° C. to −5° C. The line was then rinsed with approximately 100 L THF. The reaction mixture was stirred at −18° C. to −5° C. and then warmed to 0° C.: 5° C. The reaction was confirmed to be complete using gas chromatography (GC) (1-bromo-5-chloropentane: ≤0.4% area).

Quench and Phase Separation

Approximately 1337 kg of a solution of 9% aqueous hydrochloric acid (HCl) was added to the reaction mixture while maintaining the temperature at ≤30° C. to quench the reaction. After dosing, the reaction mixture was stirred at 20° C.: 5° C. for ≥15 minutes. The layers are allowed to settle. The pH of the aqueous layer was then measured (range: pH 6 to 10). If the pH range is not met, additional sodium hydroxide (NaOH) or HCl may be added. The lower aqueous phase was removed for disposal.

Distillation and Removal of THF

The solvent was removed by distillation under vacuum at ≤40° C. to the desired volume of approximately 950 L.

The crude compound of formula (I) concentrate was temporarily stored in a reaction vessel or drummed until processing continues to make the compound of formula (II). The compound of formula (I) process was repeated in an identical manner to obtain a second batch.

Step 2—Preparation of Compound of Formula (II)

Additional Aqueous Wash

Two individual batches of the compound of formula (I) in THF are charged to a vessel. While stirring, approximately 1767 kg of a 5% aqueous HCl solution was then charged at 20° C.±5° C. The mixture was agitated for ≥15 minutes. Agitation was stopped, and the phases were allowed to settle. The lower aqueous phase was removed, leaving the compound of formula (I)/THF in the reactor.

Iodide Exchange Reaction

Approximately 4386 L of methyl-ethyl-ketone (MEK) and approximately 824 kg of sodium iodide (NaI) were charged while stirring. The batch was heated to reflux. After approximately 30 hours, GC was used to measure reaction completion (the compound of formula (I)≤3.0% area). If the reaction has not completed, additional time is allowed and additional NaI may be charged if needed. The mixture was then cooled to approximately 20° C.±10° C.

Solvent Exchange and Aqueous Work-up

The batch was concentrated via vacuum distillation at ≤60° C. until no more distillate was collected. Approximately 3000 L of n-heptane was then charged. Approximately 2115 kg of 5% aqueous sodium bisulfite (NaHSO$_3$) was prepared and the compound of formula (II) reaction mixture was added. An n-heptane rinse of approximately 612 L was charged. The mixture was stirred at 20° C.±5° C. Agitation was stopped, and the phases were allowed to settle. The lower aqueous phase was removed for disposal. About 1976 L of water was added, the mixture was agitated, the phases were allowed to settle, and the lower aqueous phase was then removed for disposal. The water wash was repeated one more time.

Final Concentration

The batch was concentrated using vacuum distillation at ≤50° C. until no more distillate was collected. The compound of formula (II) was then drummed and sampled for intermediate testing. The expected yield range is 80% to 100%.

Step 3—Preparation of Compound of Formula (IV)

Sodium t-Pentoxide DMAc Preparation

The following first intermediate/compound of formula (IV) sequence is based on a charge of approximately 722 kg of compound of formula (II)/heptane with assay of 90.0% wt/wt, which represents a contained charge of 650 kg of compound of formula (II).

A solution of approximately 1450 kg of N, N-Dimethylacetamide (DMAc) and approximately 267.3 kg of sodium t-pentoxide was prepared in a vessel and the mixture agitated at ≤30° C.

Preparation of First Intermediate

The compound of formula (II) in heptane (approximately 722 kg), DMAc (approximately 1259 kg), and TosMIC (approximately 213.8 kg) were charged to a vessel. The mixture was then cooled to −15° C. to 0° C. and the mixture well agitated. To this solution, the sodium t-pentoxide/DMAc mixture was added while at −15° C. to 0° C. The transfer line was rinsed with approximately 178 kg DMAc. The reaction mixture was agitated at −15° C. to 0° C. The conversion was confirmed to be complete using high-performance liquid chromatography (HPLC) with ultraviolet detection (HPLC-UV) (monoalkylated TosMIC≤3.0% area and compound of formula (II)≤3.0% area). Optional kicker (additional) charges of the compound of formula (II), TosMIC, and sodium t-pentoxide can be employed as required, to ensure completion of the reaction, based on the information presented in Table 30.

TABLE 30

Optional Kicker Charges for Preparation of Intermediate

| IPC Test Result Criteria | Kicker Charge Action |
| --- | --- |
| ≤3.0% Monoalkylated TosMIC and >3.0% compound of formula (II) | Charge additional TosMIC and sodium t-pentoxide |
| >3.0% Monoalkylated TosMIC and ≤3.0% compound of formula (II) | Charge additional compound of formula (II) |
| >3.0% Monoalkylated TosMIC and >3.0% compound of formula (II) | Charge additional sodium t-pentoxide |

IPC = In-process control;
TosMIC = p-Toluenesulfonylmethyl isocyanide.

Quench and Phase Separation

Approximately 2344 L of n-heptane and approximately 2993 L of water were charged to another reactor. The first intermediate reaction mixture was transferred to the heptane/water mixture under temperature control between 0° C. and 40° C. (target 20° C.). The transfer line was then rinsed with approximately 456 L n-heptane. The mixture was agitated for 1 to 3 hours while between 0° C. and 40° C. Agitation was then stopped, and the mixture allowed to settle. The lower aqueous phase was removed for disposal. Approximately 3036 kg of a solution of about 5% aqueous sodium chloride (NaCl) was charged and the mixture agitated. The agitator was then stopped, and the mixture allowed to settle. The lower aqueous phase was removed for disposal.

Compound of Formula (IV) Reaction

Approximately 440 L of isopropyl acetate (IPAc) was added to the solution of the first intermediate in heptane and the mixture cooled to −15° C. to 0° C. Concentrated HCl (approximately 112 kg) was then added while maintaining the temperature at −15° C. to 25° C. The reaction mixture was allowed to warm, if needed, to 10° C. to 25° C. The mixture was agitated for 30 to 60 minutes once 10° C. to 25° C. was reached. The reaction conversion was measured using HPLC-UV (the first intermediate≤20% area).

Quench and Phase Separation

In a separate vessel, approximately 177 kg of NaOH (50% wt/wt,) was combined with about 1884 L of water. The resulting aqueous NaOH solution was then added to the reaction mixture at approximately 20° C. (range: 10° C. to 40° C.). The line was rinsed with approximately 124 L water. The mixture was stirred. The neutralization endpoint is pH 9 to 12. Agitation was stopped, and the phases allowed to settle. The lower aqueous phase was removed for disposal. A dilute aqueous solution, containing about 54 kg of NaCl, about 1535 L of water, and about 4.5 kg of 50% NaOH, was prepared in a separate vessel and charged to the compound of formula (IV) product mixture. A water rinse of approximately 126 L was then applied. The mixture was agitated, the phases were settled, and the lower aqueous phase removed for disposal.

Concentration

The mixture was concentrated under vacuum at ≤80° C. to a reduced volume. The batch was then cooled to approximately 20° C. and the compound of formula (IV) concentrate held until the second batch was prepared. The compound of formula (IV) process was repeated in an identical manner to provide a second batch of compound of formula (IV) in heptane. The second batch (in heptane) was then combined with the first batch for final distillation. The distillation was monitored using GC (compound of formula (IV) ≥75% weight). The packaging of product was performed. The product was weighed and sampled for intermediate testing. The expected yield range is 85% to 105%.

Step 4—Preparation of Compound of Formula (V) (Crude Bempedoic Acid)

Reaction 1 (Ketone Reduction)

Approximately 710 kg the compound of formula (IV) and approximately 1420 kg ethanol (EtOH) were charged to a vessel. While maintaining the batch at 25° C.±10° C., approximately 202 kg sodium borohydride (NaBH$_4$, 12 wt % in 40% NaOH, approximately 0.35 eq.) was charged. The charging line was then rinsed with approximately 202 kg water. After holding at 25° C.±5° C. for ≥1 hour the conversion was measured using HPLC-UV (compound of formula (IV)≤0.9% area).

Reaction 2 (Saponification)

Approximately 567 kg of a solution of NaOH (50% wt/wt) is charged at 15° C. to 50° C. The charging line is rinsed with approximately 202 kg water, and the reaction mixture is warmed at 50° C.±5° C. for ≥6 hours. The saponification is measured using HPLC-UV (compound of formula (V) monoethyl ester≤1.3% area). Approximately 2440 kg water is charged to the reaction mixture. EtOH and water are distilled under vacuum and at ≤50° C. until the batch volume reaches the target level (approximately 2845 L).

pH Adjustment, Phase Separation, and Extraction

The mixture was diluted with approximately 356L of water and 2121 kg methyl tert-butyl ether (MTBE) was then added while maintaining the batch at 15° C. to 50° C. The batch was cooled to 10° C. to 20° C. Concentrated HCl (approximately 912 kg) was added slowly at 10° C. to 20° C. A sample was taken for pH analysis and the pH was adjusted with HCl or NaOH as needed (target pH range: 5.0 to 6.0). Agitation was stopped, and the phases allowed to settle. The lower aqueous phase was removed for disposal. The concentration of the compound of formula (V) in MTBE was measured using HPLC-UV. The batch was then transferred to another vessel and rinsed forward with approximately 629 kg of MTBE.

Step 5—Purification of Compound of Formula (V)/Preparation of Crystalline Form of Compound of Formula (V)

Silica Gel Preparations

The diameter×height ratio for the silica gel plug can vary from 1×0.8 to 1×3. Approximately 78 kg of silica gel was charged to a filter. The silica gel bed was prepared by recirculating approximately 1173 kg of EtOAc at 50° C.±5° C. Excess EtOAc was removed immediately prior to filtration of the compound of formula (V) batch.

Solvent Exchange to Ethyl Acetate

The compound of formula (V) in MTBE was concentrated under vacuum at ≤50° C. to approximately 1148 L. Approximately 2608 kg of EtOAc was charged and the batch was then concentrated again to approximately 1148 L. Approximately 2086 kg of EtOAc was charged and distillation repeated. EtOAc (approximately 2086 kg) was charged and the batch was then sampled. The solvent exchange was measured with GC (MTBE≤0.1% weight). Additional EtOAc charges and distillations may be performed if necessary.

Silica Gel Filtration

When the solvent exchange was complete, the batch was warmed to 45° C. to 55° C. Then the batch was filtered through the preheated silica gel plug into another reactor. To rinse the line and the silica gel, approximately 521 kg of EtOAc was charged to the reactor, warmed to 50° C.±5° C., and then warm EtOAc was transferred through the silica gel plug. The purified compound of formula (V) in EtOAc mixture was then partially concentrated by distillation under vacuum, at ≤50° C., to a final volume of approximately 2321 L.

Crystallization

The concentrated compound of formula (V) in EtOAc was adjusted to approximately 50° C.±5° C. Approximately 31.3 kg of water was charged, and the solution was maintained at 50° C.±5° C. for ≥1 hour. The solution was then slowly cooled to 22° C.±5° C., with agitation, over ≥2 hours to start the crystallization of the compound of formula (V). The mixture was stirred at approximately 22° C.±5° C. for ≥6 hours and then slurry formation confirmed. If a slurry is not present, additional stirring at 20° C. to 25° C. and seeding may be performed if necessary. The batch was then slowly cooled to 0° C.±5° C. over ≥2 hours and stirred for ≥6 hours at 0° C.±5° C.

Optional In Situ Filtration

For vessels designed with in-reactor (in situ) filtration, the slurry was allowed to settle at approximately 0° C. The batch was then filtered, and the wet cake left in the reactor. Approximately 1386 kg of EtOAc was charged to another vessel, chilled to 0° C.±5° C. and transferred to the reactor containing wet cake. The batch was agitated at 0° C.±5° C. and then allowed to settle. The solids were filtered. The slurry wash and filtration processes were repeated 3 times in an identical manner.

Step 6—Preparation of Pharmaceutical Material Including Purified Amount of Compound of Formula (V)

Recrystallization (Ethyl Acetate Water)

Following in situ filtration, the amount of the compound of formula (V) is assumed to be approximately 488 kg, based on 100% conversion of the compound of formula (IV) charge amount (710 kg) used to prepare the compound of formula (V).

In a reactor, EtOAc was charged to the compound of formula (V) solids until the volume reaches the 1867 L mark and the suspension was then heated to 55° C. to 60° C. with stirring. To the mixture, approximately 20.5 kg of water was added, and the batch agitated at 55° C. to 70° C. for ≥1 hour. A check for the formation of a solution was performed. The batch was then transferred to another reactor via polish filtration. The reactor, filter, and line were rinsed with EtOAc. The temperature was then adjusted to 55° C.±5° C. The hot solution was then cooled over ≥2 hours to 30° C.±5° C. and then agitated at 30° C.±5° C. for ≥2 hours. If a slurry was not present, additional stirring at 30° C.±5° C. and seeding may be performed as required. The batch was then heated to 40° C. 5° C., over ≥1 hour and held at 40° C.±5° C. for ≥1 hour. The batch was then cooled to 35° C.±5° C. for over ≥1 hour and held at 35° C.±5° C. for ≥2 hours. The batch was then cooled slowly over ≥5 hours to 5° C.±5° C. and held at 5° C.±5° C. for ≥4 hours.

Isolation, Drying, and IPC Testing

The resulting solids were isolated by centrifugation and washed with ≤2000 kg acetonitrile. The wet cake was then dried under vacuum at ≤45° C. (jacket). The residual solvent was measured using GC (ACN≤410 ppm and EtOAc≤5000 ppm) to determine completion of drying. The expected yield range is 66% to 91%. If the pharmaceutical material release specification criteria were met, the product was treated as the final pharmaceutical material. If the pharmaceutical material release specifications were not met, a second recrystallization was conducted.

Optional Second Recrystallization (Ethyl Acetate Water)

The following procedure describes the second recrystallization of the compound of formula (V) for a batch size of approximately 430 kg.

Compound of formula (V) solids (approximately 430 kg) were charged to a vessel, followed by EtOAc (approximately 1238 kg). The suspension was then heated to 55° C. to 60° C. with stirring. To the mixture, approximately 18 kg of water was added, and the mixture was then agitated at 55° C. to 70° C. for ≥1 hour. A check for the formation of a solution was performed. The temperature was then adjusted to 55° C.±5° C. and the batch transferred to another reactor via polish filtration. The reactor, filter, and line were rinsed with EtOAc and the temperature then adjusted to 55° C.: 5° C. The hot solution was then cooled over ≥2 hour to 30° C.±5° C. and then agitated at 30° C.: 5° C. for ≥2 hours. If a slurry was not present, additional stirring at 30° C.±5° C. and seeding may be performed as required. The batch was then heated to 40° C.±5° C., over ≥1 hour and held at 40° C.±5° C. for ≥1 hour. The batch was then cooled to 35° C.: 5° C. for over ≥1 hour and held at 35° C.: 5° C. for ≥2 hours. The batch was then cooled slowly over ≥5 hours to 5° C.±5° C. and held at 5° C.±5° C. for ≥4 hours.

Optional Isolation, Drying, and IPC Testing

The resulting solids were isolated by centrifugation and washed with ≤2000 kg acetonitrile. The wet cake was dried under vacuum at ≤45° C. (jacket). The residual solvent was then measured using GC (ACN≤410 ppm and EtOAc≤5000 ppm) to determine completion of drying. The expected yield range is 75% to 100%. If the impurity profile criteria were met, the product is treated as the final pharmaceutical material.

Example 3: Analytical Method for Determining the Purity of the Compound of Formula (V)

Determining the Amount of Impurities

The amount of impurities present in the purified form of the compound of formula (V) was determined using a high performance liquid chromatograph equipped with gradient capability, a thermostatic column compartment and a charged aerosol detection (CAD) detector.

The amount of impurities within the purified form of the compound of formula (V) was determined to be in the range of 0.05-0.50% w/w.

Column: Waters XBridge BEH C18 (4.6 mm i.d.×150 mm, 2.5 μm)

Mobile Phase: A: 0.05% Formic acid (HCOOH) in water ($H_2O$)

Mobile Phase: B: 0.05% HCOOH in acetonitrile (ACN)

Sample temperature: Ambient

Column temperature: 40° C.

Gradient (time: A:B): (0 min: 90:10; 8.5 min., 56:44; 20 min, 45:55; 32 min., 5:95; 36 min., 5:95).

Flow rate: 1.2 mL/min

Retention time: ~15.2 min (purified form of bempedoic acid)

Determining the Purity of the Compound of Formula (V) (Bempedoic Acid)

The level of purity of the purified form of the compound of formula (V) was determined using a high performance liquid chromatograph equipped with a UV detector.

The assay for the purified form of the compound of formula (V) was determined to be in the range of 98-102% (anhydrous, solvent-free basis).

Column: Waters XBridge BEH C18 (4.6 mm i.d.×150 mm, 2.5 μm)
Mobile Phase: A: 0.05% Phosphoric acid ($H_3PO_4$) in $H_2O$:ACN (50:50)
Sample temperature: Ambient
Column temperature: 40° C.
Detection: 215 nm
Flow rate: 1.2 mL/min
Analysis time: 16 min.
Gradient: Isocratic
Retention time: ~4.6 min (purified form of bempedoic acid)

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

We claim:

1. A pharmaceutical material comprising a crystalline form of the compound of formula (V):

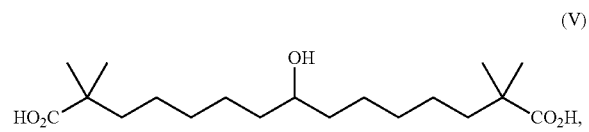

(V)

or a pharmaceutically acceptable salt thereof;
wherein the pharmaceutical material comprises the compound of formula (V), or a pharmaceutically acceptable salt thereof, in an amount greater than 99.0% by weight based on the total weight of the pharmaceutical material; and the pharmaceutical material comprises 0.0001% to 0.15%

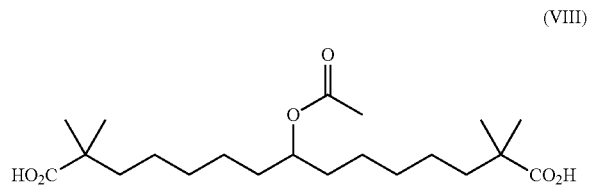 [SMILES: CC(=O)OC(CCCCCC(C)(C)C(=O)O)CCCCCC(C)(C)C(=O)O]

(VIII)

or a pharmaceutically acceptable salt thereof, based on the total weight of the pharmaceutical material.

2. The pharmaceutical material of claim 1, wherein the crystalline form of the compound of formula (V) exhibits an X-ray powder diffraction pattern comprising peaks at the following diffraction angles (2θ):10.4±0.2, 17.91±0.2, 18.8±0.2, 19.5±0.2, and 20.7±0.2.

3. The pharmaceutical material of claim 1, wherein the crystalline form of the compound of formula (V) is characterized by an X-ray powder diffraction pattern substantially the same as shown in FIG. 4.

4. The pharmaceutical material claim 1, wherein the crystalline form of the compound of formula (V) has a melting point onset as determined by differential scanning calorimetry in the range of from about 90° C. to about 94° C.

5. The pharmaceutical material of claim 1, wherein the pharmaceutical material comprises the compound of formula (V) in an amount greater than 99.5% by weight based on the total weight of the pharmaceutical material.

6. A pharmaceutical material comprising a crystalline form of the compound of formula (V):

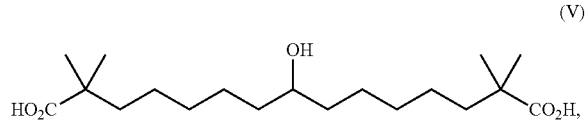 [SMILES: CC(C)(CCCCCC(O)CCCCCC(C)(C)C(=O)O)C(=O)O]

(V)

wherein the pharmaceutical material comprises the compound of formula (V) in an amount of from about 98% to about 102% by weight based on the total weight of the pharmaceutical material, as determined by a high performance liquid chromatography (HPLC) assay; and the pharmaceutical material comprises 0.0001% to 0.15% of a compound of formula (VIII):

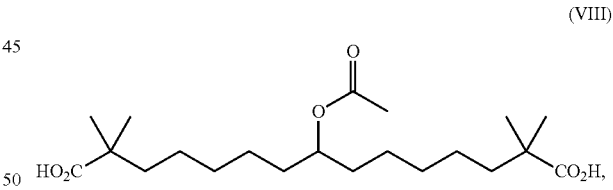

(VIII)

or a pharmaceutically acceptable salt thereof, based on the total weight of the pharmaceutical material.

7. The pharmaceutical material of claim 6, wherein the HPLC assay uses a C18 column (4.6 mm i.d.×150 mm, 2.5 μm) at a temperature of about 40° C., with isocratic elution of a mobile phase comprising about 0.05% phosphoric acid in water/acetonitrile (about 50:50) at a flow rate of about 1.2 mL/minute, and detection at 215 nm, wherein the retention time of the compound of formula (V) is about 4.6 minutes.

8. A method of treating primary hyperlipidemia in a patient in need thereof, the method comprising administering to a patient a therapeutically-effective amount of the pharmaceutical material of claim 1.

9. A pharmaceutical material comprising a crystalline form of the compound of formula (V):

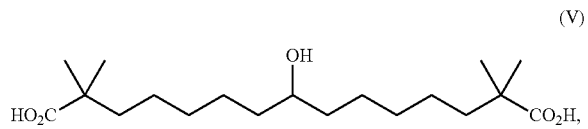
(V)

or a pharmaceutically acceptable salt thereof;
wherein the pharmaceutical material comprises the compound of formula (V), or a pharmaceutically acceptable salt thereof, in an amount greater than 85% by weight based on the total weight of the pharmaceutical material, and the pharmaceutical material comprises 0.0001% to 0.15% of a compound of formula (VIII):

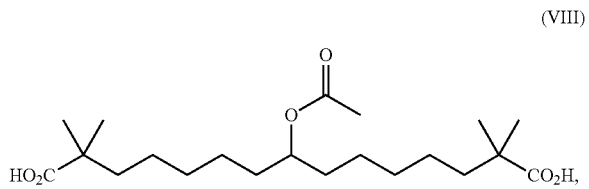 [SMILES: CC(=O)OC(CCCCCC(C)(C)C(=O)O)CCCCCC(C)(C)C(=O)O]
(VIII)

or a pharmaceutically acceptable salt thereof, based on the total weight of the pharmaceutical material.

10. The pharmaceutical material of claim 9 wherein the crystalline form of the compound of formula (V) exhibits an X-ray powder diffraction pattern comprising peaks at the following diffraction angles (2θ):10.4±0.2, 17.9±0.2, 18.8±0.2, 19.5±0.2, and 20.7±0.2.

11. The pharmaceutical material of claim 9, wherein the pharmaceutical material has a melting point onset as determined by differential scanning calorimetry in a range from 90° C. to 94° C.

12. The pharmaceutical material of claim 9 wherein the pharmaceutical material comprises the compound of formula (V), or a pharmaceutically acceptable salt thereof, in an amount greater than 90% by weight based on the total weight of the pharmaceutical material.

13. The pharmaceutical material of claim 9, wherein the pharmaceutical material comprises the compound of formula (V) or a pharmaceutically acceptable salt thereof, in an amount greater than 95% by weight based on the total weight of the pharmaceutical material.

14. The pharmaceutical material of claim 9, wherein the pharmaceutical material comprises the compound of formula (V) or a pharmaceutically acceptable salt thereof, in an amount greater than 96% by weight based on the total weight of the pharmaceutical material.

15. The pharmaceutical material of claim 9, wherein the pharmaceutical material comprises the compound of formula (V) or a pharmaceutically acceptable salt thereof, in an amount greater than 97% by weight based on the total weight of the pharmaceutical material.

16. The pharmaceutical material of claim 9, wherein the pharmaceutical material comprises the compound of formula (V) or a pharmaceutically acceptable salt thereof, in an amount greater than 98% by weight based on the total weight of the pharmaceutical material.

17. The pharmaceutical material of claim 9, further comprising a compound of formula (VI):

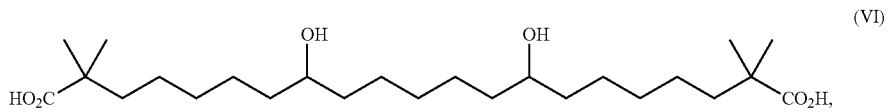 [SMILES: CC(C)(CCCCCC(O)CCCCCC(O)CCCCCC(C)(C)C(=O)O)C(=O)O]
(VI)

or a pharmaceutically acceptable salt thereof.

18. The pharmaceutical material of claim 17, wherein the pharmaceutical material comprises 0.0001% to 0.15% of a compound of formula (VI), based on the total weight of the pharmaceutical material.

19. The pharmaceutical material of claim 1, further comprising a compound of formula (VI):

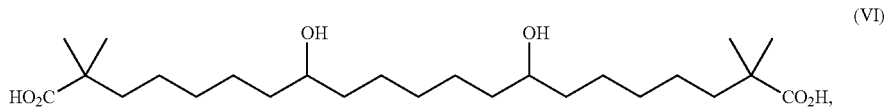
(VI)

or a pharmaceutically acceptable salt thereof.

20. The pharmaceutical material of claim 19, wherein the pharmaceutical material comprises 0.0001% to 0.15% of a compound of formula (VI), based on the total weight of the pharmaceutical material.

* * * * *